(12) United States Patent
Alster et al.

(10) Patent No.: US 10,596,038 B2
(45) Date of Patent: Mar. 24, 2020

(54) CORNEAL DENERVATION FOR TREATMENT OF OCULAR PAIN

(71) Applicant: Journey1, Inc., Brisbane, CA (US)

(72) Inventors: Yair Alster, Tel-Aviv (IL); Hanson S. Gifford, Woodside, CA (US); Cary J. Reich, Los Gatos, CA (US); Eugene De Juan, Jr., San Francisco, CA (US); John A. Scholl, San Ramon, CA (US); Jose D. Alejandro, Sunnyvale, CA (US); Douglas Sutton, Pacifica, CA (US); Omer Refaeli, Tel-Aviv (IL)

(73) Assignee: JOURNEY1, INC., Brisbane, CA (US)

( * ) Notice: Subject to any disclaimer, the term of this patent is extended or adjusted under 35 U.S.C. 154(b) by 260 days.

(21) Appl. No.: 15/684,010

(22) Filed: Aug. 23, 2017

(65) Prior Publication Data

US 2018/0000639 A1    Jan. 4, 2018

Related U.S. Application Data

(63) Continuation of application No. 13/503,841, filed as application No. PCT/US2010/053854 on Oct. 22, 2010, now abandoned.
(Continued)

(51) Int. Cl.
*A61F 9/008*    (2006.01)
*A61B 18/02*    (2006.01)
(Continued)

(52) U.S. Cl.
CPC ......... *A61F 9/008* (2013.01); *A61F 9/00804* (2013.01); *A61B 18/02* (2013.01);
(Continued)

(58) Field of Classification Search
CPC ...... A61F 9/008; A61F 9/00804; A61F 9/009; A61F 2009/00872; A61B 18/02; A61N 1/36021; A61N 1/36064
See application file for complete search history.

(56) References Cited

U.S. PATENT DOCUMENTS 2,641,161 A    6/1953    Silverstein
2,714,721 A    8/1955    Stone, Jr. et al.
(Continued)

FOREIGN PATENT DOCUMENTS

CA    993401    7/1976
CA    2174967    5/1995
(Continued)

OTHER PUBLICATIONS

Alio, Jorge L. et al. "Contact lens fitting to correct irregular astigmatism after corneal refractive surgery," Journal of Cataract & Refractive Surgery, vol. 28, No. 10, pp. 1750-1757, Oct. 2002.
(Continued)

*Primary Examiner* — Christopher A Flory
(74) *Attorney, Agent, or Firm* — Wilson Sonsini Goodrich & Rosati

(57) ABSTRACT

Methods and apparatus for the treatment of the eye to reduce pain can treat at least an outer region of the tissue so as to denervate nerves extending into the inner region and reduce the pain. For example, the cornea of the eye may comprise an inner region having an epithelial defect, and an outer portion of the cornea can be treated to reduce pain of the epithelial defect. The outer portion of the cornea can be treated to denervate nerves extending from the outer portion to the inner portion. The outer portion can be treated in many ways to denervate the nerve, for example with one or more of heat, cold or a denervating noxious substance such as
(Continued)

capsaicin. The denervation of the nerve can be reversible, such that corneal innervation can return following treatment.

17 Claims, 33 Drawing Sheets

Related U.S. Application Data

(60) Provisional application No. 61/279,612, filed on Oct. 23, 2009.

(51) Int. Cl.
*A61F 9/007* (2006.01)
*A61F 9/009* (2006.01)
*A61N 7/02* (2006.01)
*A61N 1/40* (2006.01)
*A61N 1/36* (2006.01)

(52) U.S. Cl.
CPC ............ *A61F 9/009* (2013.01); *A61F 9/0079* (2013.01); *A61F 2009/00872* (2013.01); *A61F 2009/00893* (2013.01); *A61N 1/36021* (2013.01); *A61N 1/36046* (2013.01); *A61N 1/40* (2013.01); *A61N 7/02* (2013.01)

(56) References Cited

U.S. PATENT DOCUMENTS

| | | |
|---|---|---|
| 2,952,023 A | 9/1960 | Hyman et al. |
| 3,246,941 A | 4/1966 | Moss |
| 3,431,046 A | 3/1969 | Conrad et al. |
| 3,488,111 A | 1/1970 | Isen |
| 3,489,491 A | 1/1970 | Creighton |
| 3,495,899 A | 2/1970 | Biri |
| 3,594,074 A | 7/1971 | Rosen |
| 3,619,044 A | 11/1971 | Kamath |
| 3,688,386 A | 9/1972 | Pereira |
| 3,833,786 A | 9/1974 | Brucker |
| 3,915,609 A | 10/1975 | Robinson |
| 3,944,347 A | 3/1976 | Barkdoll et al. |
| 3,973,837 A | 8/1976 | Page |
| 3,973,838 A | 8/1976 | Page |
| 4,037,866 A | 7/1977 | Price |
| 4,053,442 A | 10/1977 | Jungr et al. |
| 4,068,933 A | 1/1978 | Seiderman |
| 4,071,272 A | 1/1978 | Drdlik |
| 4,121,885 A | 10/1978 | Erickson et al. |
| 4,126,904 A | 11/1978 | Shepard et al. |
| 4,166,255 A | 8/1979 | Graham |
| 4,171,878 A | 10/1979 | Kivaev et al. |
| 4,194,815 A | 3/1980 | Trombley |
| 4,198,132 A | 4/1980 | Jacobson et al. |
| 4,200,320 A | 4/1980 | Durham |
| 4,208,362 A | 6/1980 | Deichert et al. |
| 4,211,476 A | 7/1980 | Brummel et al. |
| 4,268,131 A | 5/1981 | Miyata et al. |
| 4,268,133 A | 5/1981 | Fischer et al. |
| 4,312,575 A | 1/1982 | Peyman et al. |
| 4,346,482 A | 8/1982 | Tennant et al. |
| 4,381,007 A | 4/1983 | Doss |
| 4,407,766 A | 10/1983 | Haardt et al. |
| 4,452,776 A | 6/1984 | Refojo et al. |
| 4,452,925 A | 6/1984 | Kuzma et al. |
| 4,487,905 A | 12/1984 | Mitchell |
| 4,563,779 A | 1/1986 | Kelman et al. |
| 4,581,030 A | 4/1986 | Bruns et al. |
| 4,593,981 A | 6/1986 | Scilipoti |
| 4,621,912 A | 11/1986 | Meyer |
| 4,624,669 A | 11/1986 | Grendahl et al. |
| 4,640,594 A | 2/1987 | Berger |
| 4,666,249 A | 5/1987 | Bauman et al. |
| 4,666,267 A | 5/1987 | Wichterle |
| 4,676,790 A | 6/1987 | Kern et al. |
| 4,693,715 A | 9/1987 | Abel, Jr. et al. |
| 4,701,288 A | 10/1987 | Cook et al. |
| 4,715,858 A | 12/1987 | Lindstrom et al. |
| 4,772,283 A | 9/1988 | White |
| 4,799,931 A | 1/1989 | Lindstrom et al. |
| 4,806,382 A | 2/1989 | Goldberg et al. |
| 4,810,082 A | 3/1989 | Abel, Jr. |
| 4,834,748 A | 5/1989 | Mcdonald et al. |
| 4,851,003 A | 7/1989 | Lindstrom et al. |
| 4,886,350 A | 12/1989 | Wichterle |
| 4,890,911 A | 1/1990 | Sulc et al. |
| 4,909,896 A | 3/1990 | Ikushima et al. |
| 4,923,467 A | 5/1990 | Thompson et al. |
| 4,940,751 A | 7/1990 | Frances et al. |
| 4,943,150 A | 7/1990 | Diechert et al. |
| 4,952,045 A | 8/1990 | Stoyan |
| 4,969,912 A | 11/1990 | Kelman et al. |
| 4,973,493 A | 11/1990 | Guire et al. |
| 4,978,481 A | 12/1990 | Janssen et al. |
| 4,979,959 A | 12/1990 | Guire et al. |
| 4,981,841 A | 1/1991 | Gibson |
| 4,983,181 A | 1/1991 | Civerchia et al. |
| 4,994,081 A | 2/1991 | Civerchia et al. |
| 4,997,583 A | 3/1991 | Itzhak |
| 5,008,289 A | 4/1991 | Bernstein |
| 5,019,097 A | 5/1991 | Knight et al. |
| 5,030,230 A | 7/1991 | White et al. |
| 5,073,021 A | 12/1991 | Marron |
| 5,104,213 A | 4/1992 | Wolfson |
| 5,108,428 A | 4/1992 | Capecchi et al. |
| 5,112,350 A | 5/1992 | Civerchia et al. |
| 5,114,627 A | 5/1992 | Civerchia et al. |
| 5,143,660 A | 9/1992 | Hamilton et al. |
| 5,152,786 A | 10/1992 | Hanna |
| 5,156,622 A | 10/1992 | Thompson et al. |
| 5,159,360 A | 10/1992 | Stoy et al. |
| 5,163,596 A | 11/1992 | Ravoo et al. |
| 5,163,934 A | 11/1992 | Munnerlyn et al. |
| 5,166,710 A | 11/1992 | Hofer et al. |
| 5,171,318 A | 12/1992 | Gibson et al. |
| 5,191,365 A | 3/1993 | Stoyan |
| 5,192,316 A | 3/1993 | Ting et al. |
| 5,196,027 A | 3/1993 | Thompson et al. |
| 5,213,720 A | 5/1993 | Civerchia |
| 5,236,236 A | 8/1993 | Girimont |
| 5,244,799 A | 9/1993 | Anderson et al. |
| 5,245,367 A | 9/1993 | Miller et al. |
| 5,246,259 A | 9/1993 | Hellenkamp et al. |
| 5,178,879 A | 11/1993 | Adekunle et al. |
| 5,263,992 A | 11/1993 | Guire et al. |
| 5,292,514 A | 3/1994 | Capecchi et al. |
| 5,293,186 A | 3/1994 | Seden et al. |
| 5,312,320 A * | 5/1994 | L'Esperance, Jr. ........................ A61F 9/00804 606/5 |
| 5,346,491 A | 9/1994 | Oertli |
| 5,347,326 A | 9/1994 | Volk |
| 5,349,395 A | 9/1994 | Stoyan |
| 5,397,848 A | 3/1995 | Yang et al. |
| 5,401,508 A | 3/1995 | Manesis et al. |
| 5,428,412 A | 6/1995 | Stoyan |
| 5,433,714 A | 7/1995 | Bloomberg |
| 5,433,898 A | 7/1995 | Thakrar et al. |
| 5,434,630 A | 7/1995 | Bransome |
| 5,472,436 A | 12/1995 | Fremstad |
| 5,489,300 A | 2/1996 | Capecchi et al. |
| 5,496,084 A | 3/1996 | Medan |
| 5,517,260 A | 5/1996 | Glady et al. |
| 5,522,888 A | 6/1996 | Civerchia et al. |
| 5,538,301 A | 7/1996 | Yavitz et al. |
| 5,552,452 A | 9/1996 | Khadem et al. |
| 5,570,144 A | 10/1996 | Lofgren-Nisser |
| 5,578,332 A | 11/1996 | Hamilton et al. |
| 5,598,233 A | 1/1997 | Haralambopoulos et al. |
| 5,612,432 A | 3/1997 | Taniguchi et al. |
| 5,628,794 A | 5/1997 | Lindstrom |
| 5,632,733 A | 5/1997 | Shaw et al. |
| 5,632,773 A | 5/1997 | Graham et al. |
| 5,649,922 A | 7/1997 | Yavitz |

(56) References Cited

U.S. PATENT DOCUMENTS

| | | |
|---|---|---|
| 5,662,706 A | 9/1997 | Legerton et al. |
| 5,671,038 A | 9/1997 | Porat |
| 5,712,721 A | 1/1998 | Large |
| 5,713,957 A | 2/1998 | Steele et al. |
| 5,716,633 A | 2/1998 | Civerchia et al. |
| 5,732,990 A | 3/1998 | Yavitz et al. |
| 5,757,458 A | 5/1998 | Miller et al. |
| 5,760,100 A | 6/1998 | Nicolson et al. |
| 5,760,870 A | 6/1998 | Payor et al. |
| 5,804,263 A | 9/1998 | Goldberg et al. |
| 5,814,329 A | 9/1998 | Shah et al. |
| 5,820,624 A | 10/1998 | Yavitz |
| 5,836,313 A | 11/1998 | Perez et al. |
| 5,854,291 A | 12/1998 | Laughlin et al. |
| 5,869,533 A | 2/1999 | Holt |
| 5,885,597 A | 3/1999 | Botknecht et al. |
| 5,905,561 A | 5/1999 | Lee et al. |
| 5,910,512 A | 6/1999 | Conant |
| 5,923,397 A | 7/1999 | Bonafini, Jr. |
| 5,929,968 A | 7/1999 | Cotie et al. |
| 5,932,205 A | 8/1999 | Wang et al. |
| 5,942,243 A | 8/1999 | Shah et al. |
| 5,953,098 A | 9/1999 | Lieberman et al. |
| 5,957,921 A | 9/1999 | Mirhashemi et al. |
| 5,962,532 A | 10/1999 | Campbell et al. |
| 5,971,541 A | 10/1999 | Danker et al. |
| 5,980,040 A | 11/1999 | Xu et al. |
| 5,986,001 A | 11/1999 | Ingenito et al. |
| 6,010,219 A | 1/2000 | Stoyan |
| 6,030,974 A | 2/2000 | Schwartz et al. |
| 6,036,314 A | 3/2000 | Wolfson et al. |
| 6,036,688 A | 3/2000 | Edwards |
| 6,048,855 A | 4/2000 | De Lacharriere et al. |
| 6,055,990 A | 5/2000 | Thompson et al. |
| 6,075,066 A | 6/2000 | Matsuda et al. |
| 6,090,995 A | 7/2000 | Reich et al. |
| 6,092,898 A | 7/2000 | De Juan, Jr. |
| 6,099,121 A | 8/2000 | Chapman et al. |
| 6,143,315 A | 11/2000 | Wang et al. |
| 6,217,171 B1 | 4/2001 | Auten et al. |
| 6,244,709 B1 | 6/2001 | Vayntraub et al. |
| 6,248,788 B1 | 6/2001 | Robbins et al. |
| 6,325,509 B1 | 12/2001 | Hodur et al. |
| 6,340,229 B1 | 1/2002 | Lieberman et al. |
| 6,361,169 B1 | 3/2002 | Tung |
| 6,364,482 B1 | 4/2002 | Roffman et al. |
| 6,406,145 B1 | 6/2002 | Jubin |
| 6,454,800 B2 | 9/2002 | Dalton et al. |
| 6,474,814 B1 | 11/2002 | Griffin |
| 6,520,637 B2 | 2/2003 | Hodur et al. |
| 6,541,028 B1 | 4/2003 | Kuri-Harcuch et al. |
| 6,544,286 B1 | 4/2003 | Perez et al. |
| 6,551,307 B2 | 4/2003 | Peyman |
| 6,568,808 B2 | 5/2003 | Campin |
| 6,579,918 B1 | 6/2003 | Auten et al. |
| 6,593,370 B2 | 7/2003 | Tamura et al. |
| 6,607,522 B1 | 8/2003 | Hamblin et al. |
| 6,645,715 B1 | 11/2003 | Griffith et al. |
| 6,652,095 B2 | 11/2003 | Tung |
| 6,659,607 B2 | 12/2003 | Miyamura et al. |
| 6,689,165 B2 | 2/2004 | Jacob et al. |
| 6,702,807 B2 | 3/2004 | Peyman et al. |
| 6,726,322 B2 | 4/2004 | Andino et al. |
| 6,726,684 B1 | 4/2004 | Woloszko et al. |
| 6,779,888 B2 | 8/2004 | Marmo |
| 6,843,563 B2 | 1/2005 | Richardson |
| 6,849,671 B2 | 2/2005 | Steffen et al. |
| 6,880,558 B2 | 4/2005 | Perez |
| 6,918,904 B1 | 7/2005 | Peyman et al. |
| 6,951,894 B1 | 10/2005 | Nicolson et al. |
| 6,958,148 B1 | 10/2005 | Green et al. |
| 6,958,158 B2 | 10/2005 | Tenhuisen et al. |
| 7,004,953 B2 | 2/2006 | Pallikaris et al. |
| 7,018,039 B2 | 3/2006 | Legerton et al. |
| 7,025,455 B2 | 4/2006 | Roffman |
| 7,077,839 B2 | 7/2006 | Hamblin et al. |
| 7,080,905 B2 | 7/2006 | Marmo et al. |
| 7,097,301 B2 | 8/2006 | Legerton et al. |
| 7,104,648 B2 | 9/2006 | Dahi et al. |
| 7,150,529 B2 | 12/2006 | Legerton et al. |
| 7,163,292 B2 | 1/2007 | Dahi et al. |
| 7,193,124 B2 | 3/2007 | Coffee |
| 7,216,974 B2 | 5/2007 | Meyers et al. |
| 7,229,685 B2 | 6/2007 | Full et al. |
| 7,249,849 B2 | 7/2007 | Marmo et al. |
| 7,270,412 B2 | 9/2007 | Legerton et al. |
| 7,322,694 B2 | 1/2008 | Dahi et al. |
| 7,329,001 B2 | 2/2008 | Benrashid et al. |
| 7,338,160 B2 | 3/2008 | Lieberman et al. |
| 7,360,890 B2 | 4/2008 | Back |
| 7,377,637 B2 | 5/2008 | Legerton et al. |
| 7,401,922 B2 | 7/2008 | Legerton |
| 7,401,992 B1 | 7/2008 | Lin et al. |
| 7,404,638 B2 | 7/2008 | Miller et al. |
| 7,461,937 B2 | 12/2008 | Steffen et al. |
| 7,491,350 B2 | 2/2009 | Silvestrini |
| 7,530,689 B2 | 5/2009 | Berke |
| 7,537,339 B2 | 5/2009 | Legerton et al. |
| 7,543,936 B2 | 6/2009 | Legerton et al. |
| 7,559,649 B2 | 7/2009 | Cotie et al. |
| 7,585,074 B2 | 9/2009 | Dahi et al. |
| 7,594,725 B2 | 9/2009 | Legerton et al. |
| 7,628,810 B2 | 12/2009 | Christie et al. |
| 7,682,020 B2 | 3/2010 | Berke |
| 7,695,135 B1 | 4/2010 | Rosenthal |
| 7,699,465 B2 | 4/2010 | Dootjes et al. |
| 7,717,555 B2 | 5/2010 | Legerton et al. |
| 7,735,997 B2 | 6/2010 | Muckenhirn |
| 7,748,844 B2 | 7/2010 | Lai |
| 7,762,668 B2 | 7/2010 | Dai et al. |
| 7,828,432 B2 | 11/2010 | Meyers et al. |
| 7,859,769 B2 | 12/2010 | Zalevsky |
| 7,976,577 B2 | 7/2011 | Silvestrini |
| 7,984,988 B2 | 7/2011 | Berke |
| 8,137,344 B2 | 3/2012 | Jia et al. |
| 8,201,941 B2 | 6/2012 | Choo et al. |
| 8,459,793 B2 | 6/2013 | De Juan, Jr. et al. |
| 8,485,662 B2 | 7/2013 | Collins et al. |
| 8,591,025 B1 | 11/2013 | de Juan, Jr. |
| 8,678,584 B2 | 3/2014 | de Juan |
| 8,864,306 B2 | 10/2014 | De Juan et al. |
| 8,882,757 B2 * | 11/2014 | Muller .................. A61B 18/18 606/33 |
| 8,926,096 B2 | 1/2015 | De Juan et al. |
| 9,107,773 B2 | 8/2015 | de Juan, Jr. |
| 9,125,735 B2 | 9/2015 | De Juan et al. |
| 9,241,837 B2 | 1/2016 | De Juan et al. |
| 9,341,864 B2 | 5/2016 | De Juan et al. |
| 9,395,558 B2 | 7/2016 | de Juan, Jr. |
| 9,423,632 B2 | 8/2016 | De Juan et al. |
| 9,465,233 B2 | 10/2016 | De Juan et al. |
| 9,498,385 B2 | 11/2016 | De Juan et al. |
| 9,740,025 B2 | 8/2017 | De Juan et al. |
| 9,740,026 B2 | 8/2017 | De Juan et al. |
| 9,810,921 B2 | 11/2017 | De Juan et al. |
| 9,851,586 B2 | 12/2017 | De Juan et al. |
| 9,943,401 B2 | 4/2018 | De Juan et al. |
| 10,036,900 B2 | 7/2018 | De Juan et al. |
| 10,039,671 B2 | 8/2018 | De Juan et al. |
| 10,191,303 B2 | 1/2019 | De Juan et al. |
| 2001/0047203 A1 | 11/2001 | Dalton et al. |
| 2002/0095199 A1 | 7/2002 | West, Jr. et al. |
| 2002/0107567 A1 | 8/2002 | Terwee et al. |
| 2002/0151972 A1 | 10/2002 | Hughes et al. |
| 2002/0164484 A1 | 11/2002 | Jiang et al. |
| 2003/0144650 A1 | 7/2003 | Smith |
| 2003/0187515 A1 | 10/2003 | Hariri et al. |
| 2004/0015163 A1 | 1/2004 | Buysse |
| 2004/0037866 A1 | 2/2004 | Semertzides et al. |
| 2004/0048796 A1 | 3/2004 | Hariri et al. |
| 2004/0053442 A1 | 3/2004 | Akram et al. |
| 2004/0068933 A1 | 4/2004 | Nakamura et al. |
| 2004/0071272 A1 | 4/2004 | Mizuguchi et al. |
| 2004/0088050 A1 | 5/2004 | Norrby et al. |

(56) References Cited

U.S. PATENT DOCUMENTS

| | | |
|---|---|---|
| 2004/0121885 A1 | 6/2004 | Garcia-Rill et al. |
| 2004/0141150 A1 | 7/2004 | Roffman et al. |
| 2004/0143026 A1 | 7/2004 | Shah et al. |
| 2004/0166255 A1 | 8/2004 | Pierce et al. |
| 2004/0170666 A1 | 9/2004 | Keats et al. |
| 2004/0171878 A1 | 9/2004 | Kok et al. |
| 2004/0184158 A1 | 9/2004 | Shadduck |
| 2004/0194815 A1 | 10/2004 | Deiss et al. |
| 2004/0200320 A1 | 10/2004 | Knopp et al. |
| 2004/0208362 A1 | 10/2004 | Suzuki et al. |
| 2004/0211476 A1 | 10/2004 | Hager et al. |
| 2004/0212779 A1 | 10/2004 | Dahi et al. |
| 2005/0018130 A1 | 1/2005 | Dahi et al. |
| 2005/0028723 A1 | 2/2005 | Ancel et al. |
| 2005/0033420 A1 | 2/2005 | Christie et al. |
| 2005/0107775 A1 | 5/2005 | Huang et al. |
| 2005/0191365 A1 | 9/2005 | Creasey et al. |
| 2005/0213030 A1 | 9/2005 | Meyers et al. |
| 2005/0236236 A1 | 10/2005 | Farooq et al. |
| 2005/0238692 A1 | 10/2005 | Hughes et al. |
| 2005/0245367 A1 | 11/2005 | Horvath et al. |
| 2005/0246259 A1 | 11/2005 | Lavoie et al. |
| 2005/0259221 A1 | 11/2005 | Marmo |
| 2005/0288196 A1 | 12/2005 | Horn |
| 2006/0010219 A1 | 1/2006 | Saito et al. |
| 2006/0013050 A1 | 1/2006 | Fukuzumi et al. |
| 2006/0030974 A1 | 2/2006 | Tsukasaki et al. |
| 2006/0034807 A1 | 2/2006 | Griffith et al. |
| 2006/0036314 A1 | 2/2006 | Perez et al. |
| 2006/0048855 A1 | 3/2006 | Honkura et al. |
| 2006/0075066 A1 | 4/2006 | Farchmin et al. |
| 2006/0077581 A1 | 4/2006 | Schwiegerling |
| 2006/0083773 A1 | 4/2006 | Myung |
| 2006/0099121 A1 | 5/2006 | Doona et al. |
| 2006/0100617 A1 | 5/2006 | Boukhny |
| 2006/0132707 A1 | 6/2006 | Tung |
| 2006/0134170 A1 | 6/2006 | Griffith et al. |
| 2006/0152673 A1 | 7/2006 | Cotie et al. |
| 2006/0197909 A1 | 9/2006 | Legerton |
| 2006/0197910 A1 | 9/2006 | Legerton |
| 2006/0217171 A1 | 9/2006 | Roireau et al. |
| 2006/0235514 A1 | 10/2006 | Silvestrini |
| 2006/0238712 A1 | 10/2006 | Dahi |
| 2006/0241751 A1 | 10/2006 | Marmo |
| 2006/0244709 A1 | 11/2006 | Lin et al. |
| 2006/0246113 A1 | 11/2006 | Griffith et al. |
| 2006/0248788 A1 | 11/2006 | Harris et al. |
| 2006/0250576 A1 | 11/2006 | Legerton et al. |
| 2006/0256283 A1 | 11/2006 | Legerton |
| 2006/0256284 A1 | 11/2006 | Dahi |
| 2006/0285071 A1 | 12/2006 | Erickson et al. |
| 2006/0285072 A1 | 12/2006 | Dahi et al. |
| 2006/0290882 A1 | 12/2006 | Meyers et al. |
| 2007/0002046 A1 | 1/2007 | Tanacs et al. |
| 2007/0013869 A1 | 1/2007 | Dahi |
| 2007/0014760 A1 | 1/2007 | Peyman |
| 2007/0018039 A1 | 1/2007 | Hillen et al. |
| 2007/0025455 A1 | 2/2007 | Greenwood et al. |
| 2007/0037898 A1 | 2/2007 | Phelan et al. |
| 2007/0046894 A1 | 3/2007 | Muckenhirn |
| 2007/0055222 A1* | 3/2007 | Hohla ............... A61F 9/00804 606/12 |
| 2007/0080905 A1 | 4/2007 | Takahara et al. |
| 2007/0097301 A1 | 5/2007 | Yang et al. |
| 2007/0104648 A1 | 5/2007 | Shull et al. |
| 2007/0106394 A1 | 5/2007 | Chen |
| 2007/0129720 A1 | 6/2007 | Demarias et al. |
| 2007/0132948 A1 | 6/2007 | Evans |
| 2007/0135915 A1 | 6/2007 | Klima |
| 2007/0150529 A1 | 6/2007 | Mccall et al. |
| 2007/0163292 A1 | 7/2007 | Weng et al. |
| 2007/0182920 A1 | 8/2007 | Back et al. |
| 2007/0193124 A1 | 8/2007 | Thompson et al. |
| 2007/0196454 A1 | 8/2007 | Stockman et al. |
| 2007/0216974 A1 | 9/2007 | Silverbrook et al. |
| 2007/0232755 A1 | 10/2007 | Matsushita et al. |
| 2007/0242216 A1 | 10/2007 | Dootjes et al. |
| 2007/0244559 A1 | 10/2007 | Shiuey |
| 2007/0249849 A1 | 10/2007 | Wiebe et al. |
| 2007/0270412 A1 | 11/2007 | Bell et al. |
| 2007/0273834 A1 | 11/2007 | Legerton |
| 2008/0039832 A1 | 2/2008 | Palanker et al. |
| 2008/0074611 A1 | 3/2008 | Meyers et al. |
| 2008/0100796 A1 | 5/2008 | Pruitt et al. |
| 2008/0201941 A1 | 8/2008 | Montena et al. |
| 2008/0243156 A1 | 10/2008 | John |
| 2008/0287915 A1 | 11/2008 | Rosenthal et al. |
| 2008/0291391 A1 | 11/2008 | Meyers et al. |
| 2009/0033864 A1 | 2/2009 | Shone et al. |
| 2009/0096987 A1 | 4/2009 | Lai et al. |
| 2009/0161826 A1* | 6/2009 | Gertner ............... A61N 5/1017 378/65 |
| 2009/0161827 A1* | 6/2009 | Gertner ............... A61F 9/008 378/65 |
| 2009/0182312 A1* | 7/2009 | Gertner ............... A61F 9/008 606/4 |
| 2009/0209954 A1* | 8/2009 | Muller ............... A61B 18/14 606/33 |
| 2009/0216217 A1* | 8/2009 | Odrich ............... A61F 9/008 606/5 |
| 2009/0237612 A1 | 9/2009 | Cotie et al. |
| 2009/0244477 A1 | 10/2009 | Pugh et al. |
| 2009/0303434 A1 | 12/2009 | Tung |
| 2009/0303442 A1 | 12/2009 | Choo et al. |
| 2010/0036488 A1 | 2/2010 | De Juan, Jr. et al. |
| 2010/0060849 A1 | 3/2010 | Hibino |
| 2010/0128224 A1 | 5/2010 | Legerton |
| 2010/0145447 A1 | 6/2010 | Jia et al. |
| 2010/0157250 A1 | 6/2010 | Berke |
| 2010/0185192 A1* | 7/2010 | Muller ............... A61B 18/18 606/33 |
| 2010/0191178 A1* | 7/2010 | Ross ............... A61F 9/00736 604/22 |
| 2010/0208196 A1 | 8/2010 | Benrashid et al. |
| 2010/0271589 A1 | 10/2010 | Legerton et al. |
| 2011/0034854 A1 | 2/2011 | Neuberger et al. |
| 2011/0071631 A1 | 3/2011 | Rosenthal |
| 2011/0081000 A1* | 4/2011 | Gertner ............... A61F 9/008 378/65 |
| 2011/0081001 A1* | 4/2011 | Gertner ............... A61N 5/1017 378/65 |
| 2011/0190742 A1* | 8/2011 | Anisinnov ............ A61F 9/0079 606/5 |
| 2011/0208300 A1 | 8/2011 | De Juan, Jr. et al. |
| 2012/0105804 A1 | 5/2012 | Legerton |
| 2012/0113386 A1 | 5/2012 | Back |
| 2012/0169994 A1 | 7/2012 | Matsushita et al. |
| 2012/0310133 A1 | 12/2012 | De Juan, Jr. et al. |
| 2012/0327362 A1 | 12/2012 | Doraiswamy et al. |
| 2013/0025606 A1 | 1/2013 | De Juan, Jr. et al. |
| 2013/0066283 A1 | 3/2013 | De Juan, Jr. et al. |
| 2013/0070200 A1 | 3/2013 | De Juan, Jr. et al. |
| 2013/0077044 A1 | 3/2013 | De Juan, Jr. et al. |
| 2013/0201442 A1 | 8/2013 | Back |
| 2013/0201443 A1 | 8/2013 | Back et al. |
| 2013/0201454 A1 | 8/2013 | Back |
| 2013/0208236 A1 | 8/2013 | McCabe et al. |
| 2013/0208237 A1 | 8/2013 | Hawke et al. |
| 2013/0222761 A1 | 8/2013 | Hansen et al. |
| 2013/0242255 A1 | 9/2013 | Caldarise et al. |
| 2013/0258276 A1 | 10/2013 | Hansen et al. |
| 2013/0278890 A1 | 10/2013 | de Juan et al. |
| 2013/0293832 A1 | 11/2013 | de Juan et al. |
| 2014/0028979 A1 | 1/2014 | de Juan et al. |
| 2014/0043588 A1 | 2/2014 | Grant et al. |
| 2014/0069438 A1 | 3/2014 | de Juan et al. |
| 2014/0069439 A1 | 3/2014 | de Juan et al. |
| 2014/0155800 A1 | 6/2014 | de Juan et al. |
| 2014/0251347 A1 | 9/2014 | de Juan et al. |
| 2014/0362338 A1 | 12/2014 | de Juan et al. |
| 2015/0055081 A1 | 2/2015 | de Juan et al. |
| 2015/0077701 A1 | 3/2015 | de Juan et al. |
| 2016/0067109 A1 | 3/2016 | de Juan et al. |

(56) References Cited

U.S. PATENT DOCUMENTS

| | | | |
|---|---|---|---|
| 2016/0170233 A1 | 6/2016 | De Juan et al. | |
| 2016/0223835 A1 | 8/2016 | de Juan et al. | |
| 2016/0334640 A1 | 11/2016 | de Juan et al. | |
| 2016/0370603 A1 | 12/2016 | De Juan et al. | |
| 2017/0023800 A1 | 1/2017 | De Juan, Jr. et al. | |
| 2017/0038604 A1 | 2/2017 | De Juan et al. | |
| 2017/0131566 A1 | 5/2017 | De Juan, Jr. et al. | |
| 2017/0315380 A1 | 11/2017 | De Juan, Jr. et al. | |
| 2017/0315381 A1 | 11/2017 | De Juan, Jr. et al. | |
| 2017/0340481 A1* | 11/2017 | Daxer | A61F 9/0079 |
| 2018/0011341 A1 | 1/2018 | De Juan et al. | |
| 2018/0193133 A1 | 7/2018 | De Juan et al. | |
| 2018/0321511 A1 | 11/2018 | De Juan et al. | |
| 2018/0344521 A1* | 12/2018 | Daxer | A61F 9/0079 |
| 2019/0353930 A1 | 11/2019 | De Juan, Jr. et al. | |
| 2020/0004047 A1 | 1/2020 | De Juan, Jr. et al. | |

FOREIGN PATENT DOCUMENTS

| | | |
|---|---|---|
| DE | 3143839 | 5/1983 |
| EP | 0042679 | 12/1981 |
| EP | 0434205 | 6/1991 |
| EP | 0574352 | 12/1993 |
| EP | 0590772 | 4/1994 |
| EP | 0378512 | 2/1995 |
| EP | 0378512 B1 | 2/1995 |
| EP | 0638416 A1 | 2/1995 |
| EP | 0683416 | 11/1995 |
| EP | 0590772 B1 | 4/1998 |
| EP | 0985157 | 12/1998 |
| EP | 0985157 B1 | 10/2004 |
| EP | 1496388 | 1/2005 |
| EP | 1629317 A2 | 3/2006 |
| EP | 1664907 | 6/2006 |
| FR | 2330025 | 5/1977 |
| GB | 2107895 | 5/1983 |
| JP | 52-78453 | 7/1977 |
| JP | S55101125 | 7/1980 |
| JP | S5727456 | 6/1982 |
| JP | S5727457 | 6/1982 |
| JP | 59-43931 | 3/1984 |
| JP | 2661909 | 10/1997 |
| JP | H11151263 | 6/1999 |
| JP | H11249048 | 9/1999 |
| JP | 2003-107411 | 4/2003 |
| JP | 2004504105 | 2/2004 |
| JP | 2004510199 | 4/2004 |
| WO | 199014083 | 11/1990 |
| WO | 199207617 | 5/1992 |
| WO | 199307840 | 4/1993 |
| WO | 199405225 | 3/1994 |
| WO | 94/29756 | 12/1994 |
| WO | 199513764 | 5/1995 |
| WO | 199515134 | 6/1995 |
| WO | 199627816 | 9/1996 |
| WO | 199719381 | 5/1997 |
| WO | 199803267 | 1/1998 |
| WO | 199854603 | 12/1998 |
| WO | 199930560 | 6/1999 |
| WO | 199943354 | 9/1999 |
| WO | 199946631 | 9/1999 |
| WO | 200009042 | 2/2000 |
| WO | 200168082 | 9/2001 |
| WO | 200206883 | 1/2002 |
| WO | 200210841 | 2/2002 |
| WO | 2002068008 | 9/2002 |
| WO | 2003097759 | 11/2003 |
| WO | 2004068196 | 8/2004 |
| WO | 2004097502 | 11/2004 |
| WO | 2004109368 | 12/2004 |
| WO | 2005079290 | 9/2005 |
| WO | 2005116729 | 12/2005 |
| WO | 2006026666 | 3/2006 |
| WO | 2006121591 | 11/2006 |
| WO | 2006134649 | 12/2006 |
| WO | 2007002231 | 1/2007 |
| WO | 2007044513 | 4/2007 |
| WO | 2007053297 | 5/2007 |
| WO | 2009065061 | 5/2009 |
| WO | 2009073213 | 6/2009 |
| WO | 2006113149 | 10/2009 |
| WO | 2009145842 | 12/2009 |
| WO | WO-2009146151 A2 | 12/2009 |
| WO | 2010051172 | 5/2010 |
| WO | 2010144317 | 12/2010 |
| WO | 2011050327 | 4/2011 |
| WO | 2011050365 | 4/2011 |
| WO | 2012061160 | 5/2012 |
| WO | 2012149056 | 11/2012 |
| WO | 2011/004800 | 12/2012 |
| WO | 2013184239 | 12/2013 |
| WO | WO-2014043221 A1 | 3/2014 |
| WO | WO-2014210186 A2 | 12/2014 |
| WO | WO-2015069927 A1 | 5/2015 |
| WO | WO-2015073718 A1 | 5/2015 |
| WO | WO-2015116559 A1 | 8/2015 |

OTHER PUBLICATIONS

Bausch & Lomb Inc. Boston® Materials & Solutions: Product Guide, 2009.

Bissen-Miyajima, Hiroko et al., "Role of the endothelial pump in flap adhesion after laser in situ keratomileusis," Journal of Cataract & Refractive Surgery, vol. 30, No. 9, pp. 1989-1992, Sep. 2004.

Schimmelpfenning, B. et al., "A technique for controlled sensory denervation of the rabbit cornea," Database Accession No. NLM7129102, Graefe's Archive for Clinical and Experimental Opthalmology, vol. 218, No. 6, pp. 287-293, Jun. 1982 (abstract only).

SynergEyes, Inc., "SynergEyes® A Practitioner Training," Mar. 2011, retrieved from the Internet at <http://www.fitsynergeyes.com/syn_a/synergeyesA_presentation.pdf>.

SynergEyes, Inc., "SynergEyes® A," package insert, P/N. 70008 Rev. I, Oct. 2008.

SynergEyes®, Inc., Product Overview of CLEARKONE® and SYNERGEYES® PS, retrieved from the Internet at http://www.synergeyes.com/index.html on May 29, 2012.

European Patent Application No. 10825787.4, Examination Report dated Aug. 12, 2014.

European Patent Application No. 10825787.4, Search Report dated Jun. 18, 2013.

European Patent Application No. 98936282.7, Examination Report dated Mar. 26, 2004.

International Application No. PCT/US2009/002166, International Preliminary Report on Patentability dated Oct. 5, 2010.

International Application No. PCT/US2009/002166, International Search Report and Written Opinion dated Nov. 19, 2009.

International Application No. PCT/US2010/053854, International Preliminary Report on Patentability dated Apr. 24, 2012.

International Application No. PCT/US2010/053854, International Search Report and Written Opinion dated Mar. 1, 2011.

International Application No. PCT/US2010/053975, International Preliminary Report on Patentability dated Apr. 24, 2012.

International Application No. PCT/US2010/053975, International Search Report and Written Opinion dated Feb. 11, 2011.

International Application No. PCT/US2011/057755, International Search Report dated Feb. 7, 2012.

International Application No. PCT/US2012/035050, International Search Report and Written Opinion dated Oct. 3, 2012.

International Application No. PCT/US2013/037219, International Search Report and Written Opinion dated Sep. 30, 2013.

International Application No. PCT/US2013/059244, International Search Report and Written Opinion dated Nov. 26, 2013.

International Application No. PCT/US2014/044136, International Search Report and Written Opinion dated Jan. 16, 2015.

International Application No. PCT/US2014/064391, International Search Report and Written Opinion dated Jan. 26, 2015.

International Application No. PCT/US2014/065543, International Search Report and Written Opinion dated Feb. 25, 2015.

(56) References Cited

OTHER PUBLICATIONS

International Application No. PCT/US2014/065543, International Preliminary Report in Patentability dated May 17, 2016.
International Application No. PCT/US2015/013006, International Search Report and Written Opinion dated Apr. 2, 2015.
Japanese Patent Application No. 2011-502997, Office Action dated Jun. 14, 2013.
Japanese Patent Application No. 2011-502997, Office Action dated Mar. 3, 2014.
U.S. Appl. No. 12/384,659, Non-Final Office Action dated Jan. 21, 2016.
U.S. Appl. No. 13/456,168, Non-Final Office Action dated Sep. 12, 2013.
U.S. Appl. No. 13/456,168, Notice of Allowance dated May 30, 2014.
U.S. Appl. No. 13/503,841, Final Office Action dated Nov. 26, 2014.
U.S. Appl. No. 13/503,841, Non-Final Office Action dated Jun. 27, 2014.
U.S. Appl. No. 13/503,841, Non-Final Office Action dated Nov. 16, 2015.
U.S. Appl. No. 13/503,841, Final Office Action dated Jun. 9, 2016.
U.S. Appl. No. 13/503,841, Non-Final Office Action dated Mar. 1, 2017.
U.S. Appl. No. 13/503,842, Final Office Action dated Aug. 13, 2014.
U.S. Appl. No. 13/503,842, Non-Final Office Action dated Apr. 3, 2014.
U.S. Appl. No. 13/503,842, Non-Final Office Action dated Nov. 25, 2015.
U.S. Appl. No. 13/503,842, Notice of Allowance dated Jul. 11, 2016.
U.S. Appl. No. 13/555,056, Final Office Action dated Sep. 5, 2014.
U.S. Appl. No. 13/555,056, Non-Final Office Action dated Mar. 28, 2014.
U.S. Appl. No. 13/615,111, Notice of Allowance dated Apr. 23, 2013.
U.S. Appl. No. 13/715,917, Notice of Allowance dated Aug. 1, 2013.
U.S. Appl. No. 13/865,780, Notice of Allowance dated Mar. 28, 2016.
U.S. Appl. No. 13/885,135, Non-Final Office Action dated Nov. 18, 2014.
U.S. Appl. No. 13/885,135, Notice of Allowance dated Mar. 16, 2016.
U.S. Appl. No. 13/894,176, Non-Final Office Action dated Aug. 5, 2013.
U.S. Appl. No. 13/894,176, Notice of Allowance dated Feb. 26, 2014.
U.S. Appl. No. 13/928,077, Notice of Allowance dated Jan. 15, 2014.
U.S. Appl. No. 14/061,311, Non-Final Office Action dated Apr. 21, 2016.
U.S. Appl. No. 14/286,605, Non-Final Office Action dated Dec. 18, 2014.
U.S. Appl. No. 14/468,075, Final Office Action dated Apr. 1, 2016.
U.S. Appl. No. 14/532,707, Non-Final Office Action dated Feb. 25, 2016.
U.S. Appl. No. 14/532,707, Notice of Allowance dated Jun. 8, 2016.
U.S. Appl. No. 14/532,732, Non-Final Office Action dated Apr. 11, 2016.
U.S. Appl. No. 14/532,732, Final Office Action dated Oct. 3, 2016.
U.S. Appl. No. 14/539,698, Notice of Allowance dated Jan. 21, 2016.
U.S. Appl. No. 14/468,075, Non-Final Office Action dated Nov. 7, 2016.
U.S. Appl. No. 14/793,965, Non-Final Office Action dated Dec. 31, 2015.
U.S. Appl. No. 14/966,918, Non-Final Office Action dated Nov. 18, 2016.
Australian Examination Report for Application No. 2012249773, dated Jun. 23, 2016, 4 pages.
Canadian Examination Report for Application No. 2,816,031, dated Aug. 31, 2017, 3 pages.
Canadian Examination Report for Application No. 2,916,885, dated Jan. 24, 2017, 5 pages.
Examination Search Report for European Application No. 10825813.8, dated Feb. 20, 2017, 7 pages.
Non-Final Office Action for U.S. Appl. No. 15/096,442, dated Dec. 28, 2016, 16 pages.
Non-Final Office Action for U.S. Appl. No. 12/384,659, dated May 30, 2017, 5 pages.
Non-Final Office Action for U.S. Appl. No. 15/184,922, dated Jun. 2, 2017, 22 pages.
Final Office Action for U.S. Appl. No. 14/061,311, dated Mar. 9, 2017, 16 pages.
Non-Final Office Action for U.S. Appl. No. 14/173,516, dated Feb. 8, 2017, 11 pages.
Non-Final Office Action for U.S. Appl. No. 15/253,183, dated Nov. 3, 2017, 7 pages.
Extended European Search Report for EP Application No. 17183160.5, dated Sep. 12, 2017, 6 pages.
JP2011502997 English translation of Japanese Office Action dated Jun. 14, 2013.
Muller et al. Architecture of human corneal nerves. Invest Ophthalmol Vis Sci. 38:985-994 (1997).
PCT/US2013/033567 International Search Report dated Mar. 4, 2014.
Sorbara et al. Metrics of the normal cornea: anterior segment imaging with the Visante OCT. Clin Exp Optom 93(3):150-156 (2010).
U.S. Appl. No. 12/384,659 Office Action dated Nov. 4, 2016.
U.S. Appl. No. 12/897,131 Office Action dated Jan. 24, 2013.
U.S. Appl. No. 12/897,131 Office Action dated Jul. 5, 2012.
U.S. Appl. No. 12/897,131 Office Action dated Sep. 9, 2014.
U.S. Appl. No. 13/865,780 Office Action dated Nov. 6, 2015.
U.S. Appl. No. 13/885,135 Office Action dated Jun. 11, 2015.
U.S. Appl. No. 13/928,077 Office Action dated Oct. 22, 2013.
U.S. Appl. No. 14/173,516 Office Action dated Apr. 3, 2019.
U.S. Appl. No. 14/468,075 Office Action dated Nov. 5, 2015.
U.S. Appl. No. 14/539,698 Office Action dated Oct. 9, 2015.
U.S. Appl. No. 15/184,922 Office Action dated Mar. 30, 2018.
U.S. Appl. No. 15/209,511 Office Action dated Apr. 30, 2018.
U.S. Appl. No. 15/209,511 Office Action dated Jan. 3, 2019.
U.S. Appl. No. 15/221,942 Office Action dated Feb. 1, 2018.
U.S. Appl. No. 15/289,793 Office Action dated Jan. 22, 2019.
U.S. Appl. No. 15/652,855 Office Action dated Aug. 9, 2018.
U.S. Appl. No. 15/652,855 Office Action dated Mar. 1, 2019.
U.S. Appl. No. 15/654,344 Office Action dated Mar. 22, 2019.
U.S. Appl. No. 15/695,889 Office Action dated Sep. 18, 2018.
U.S. Appl. No. 15/807,985 Office Action dated Feb. 5, 2019.
U.S. Appl. No. 15/917,071 Office Action dated Sep. 7, 2018.
U.S. Appl. No. 15/209,511 Office Action dated Aug. 5, 2019.
U.S. Appl. No. 15/695,889 Office Action dated Jun. 13, 2019.

* cited by examiner

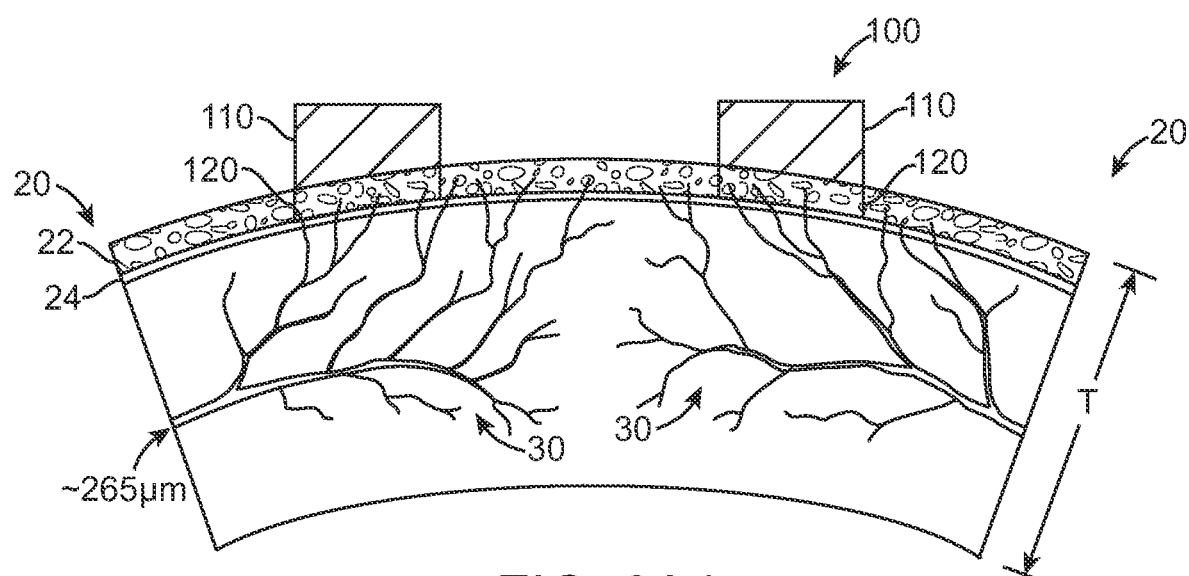
FIG. 2A1
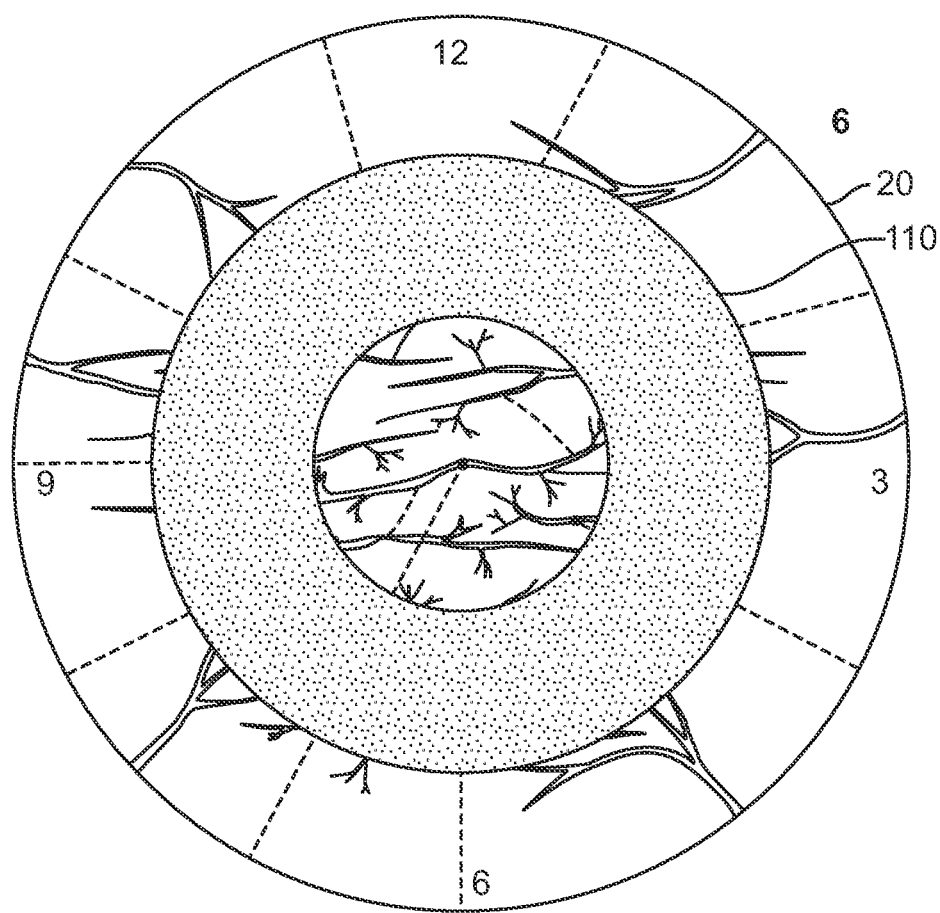
FIG. 2B1

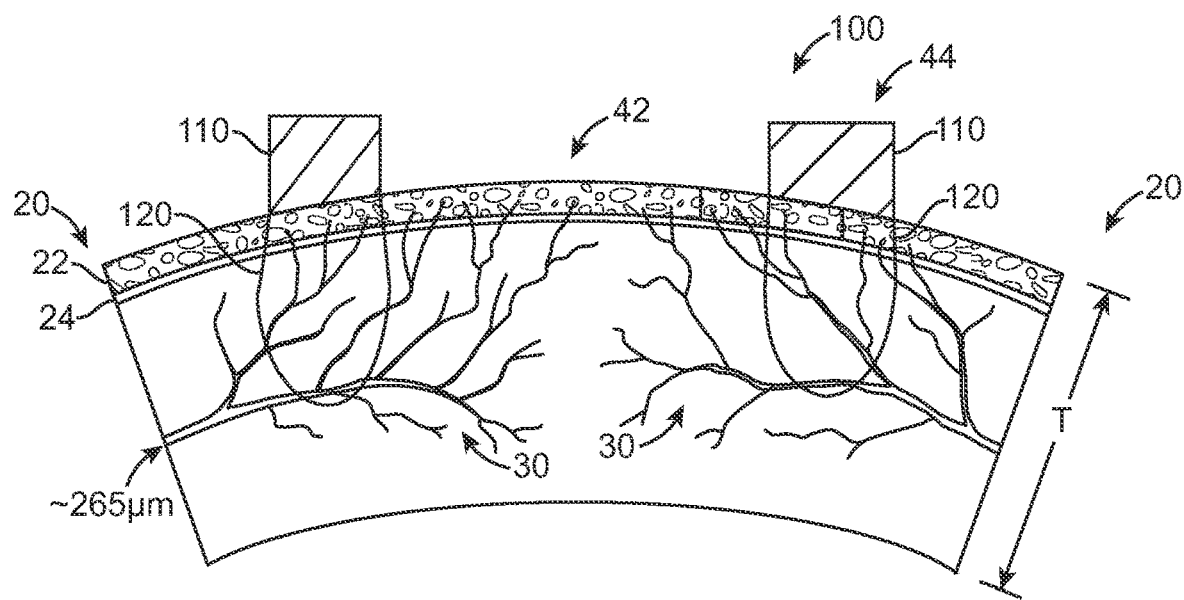
FIG. 2A2
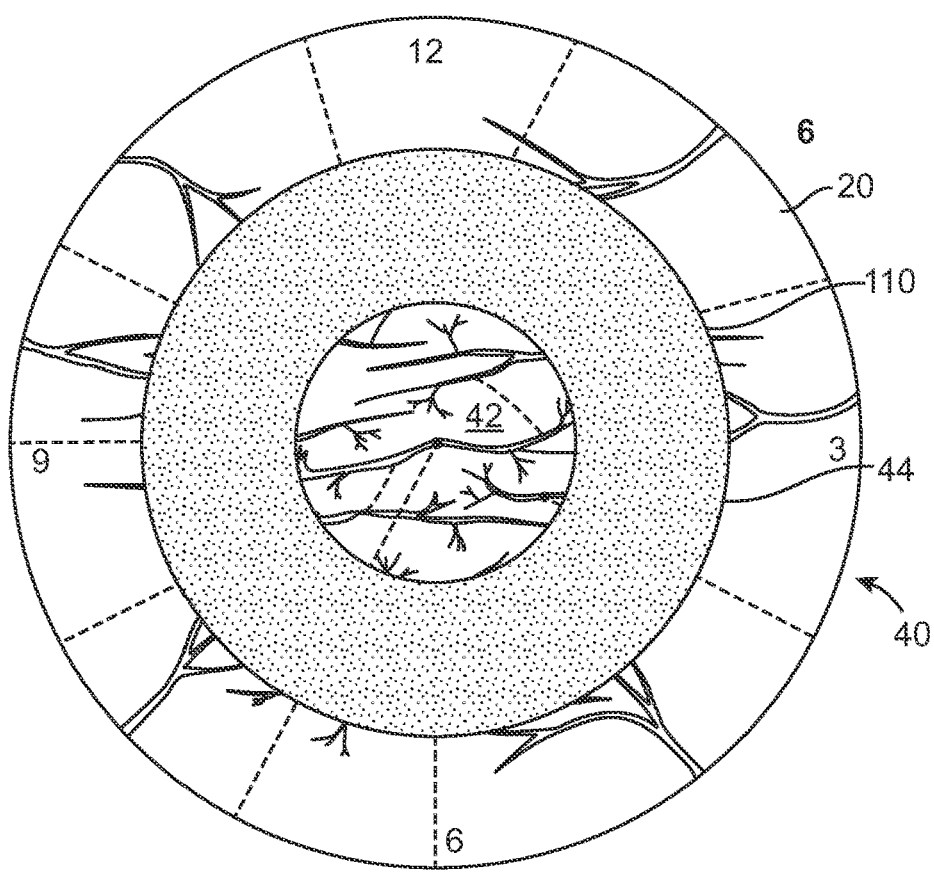
FIG. 2B2

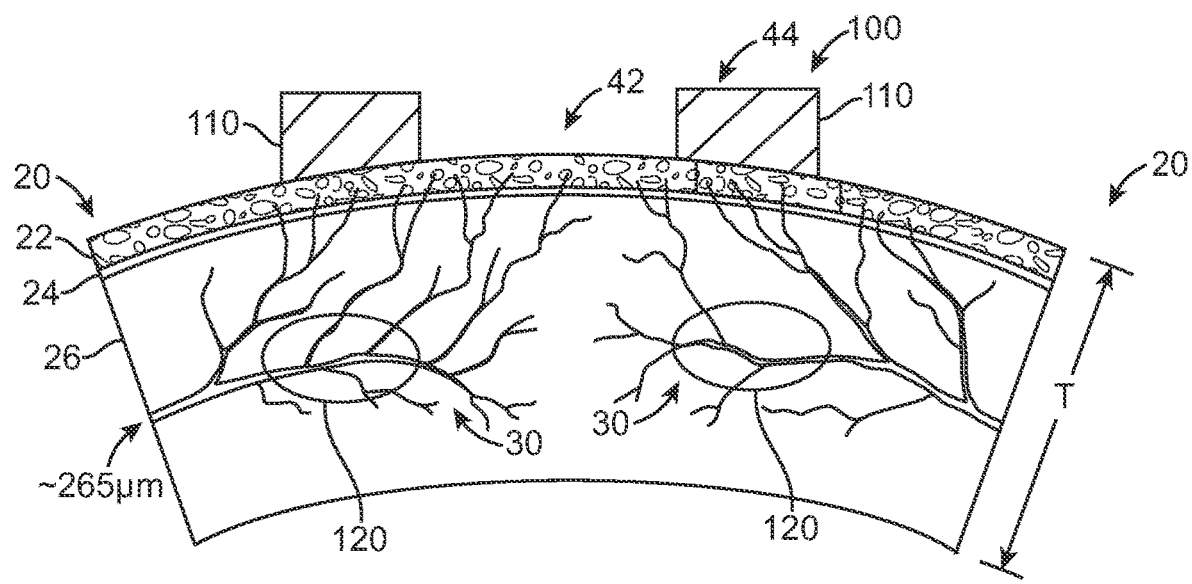
FIG. 2A3
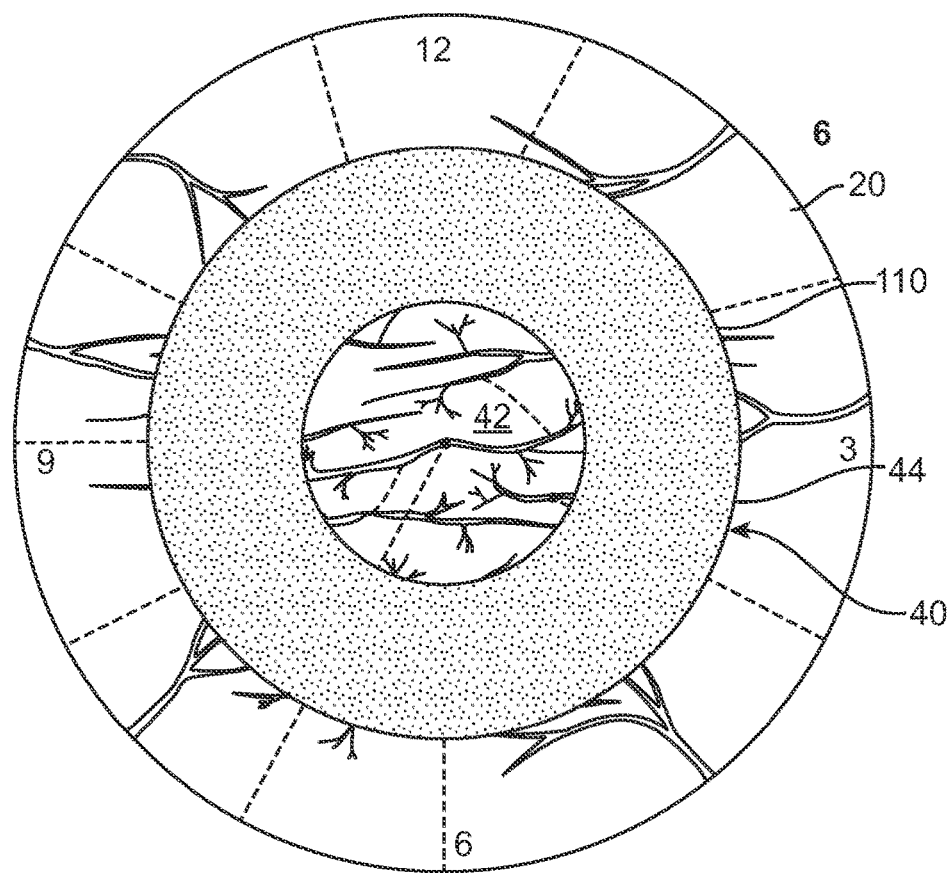
FIG. 2B3

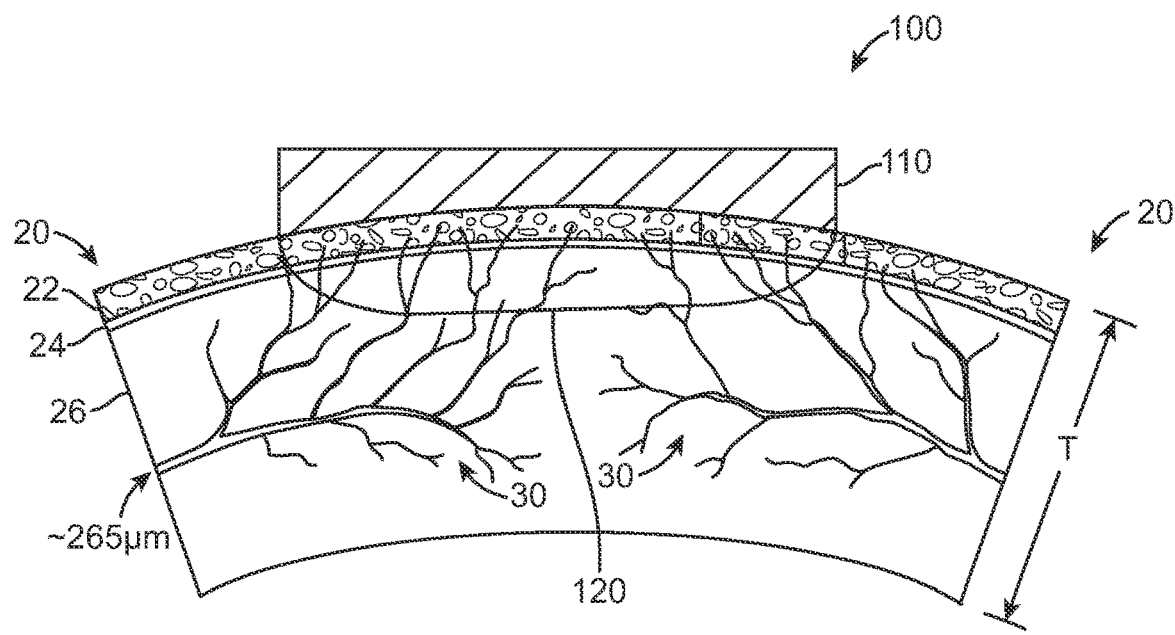
FIG. 2A4
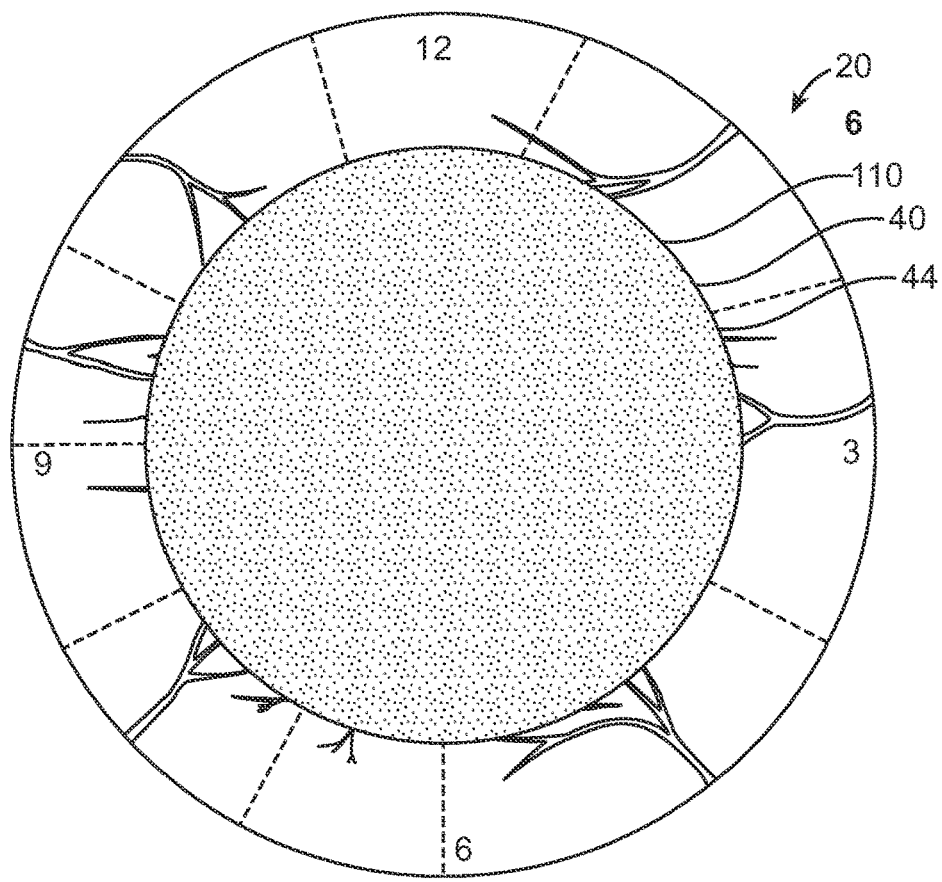
FIG. 2B4

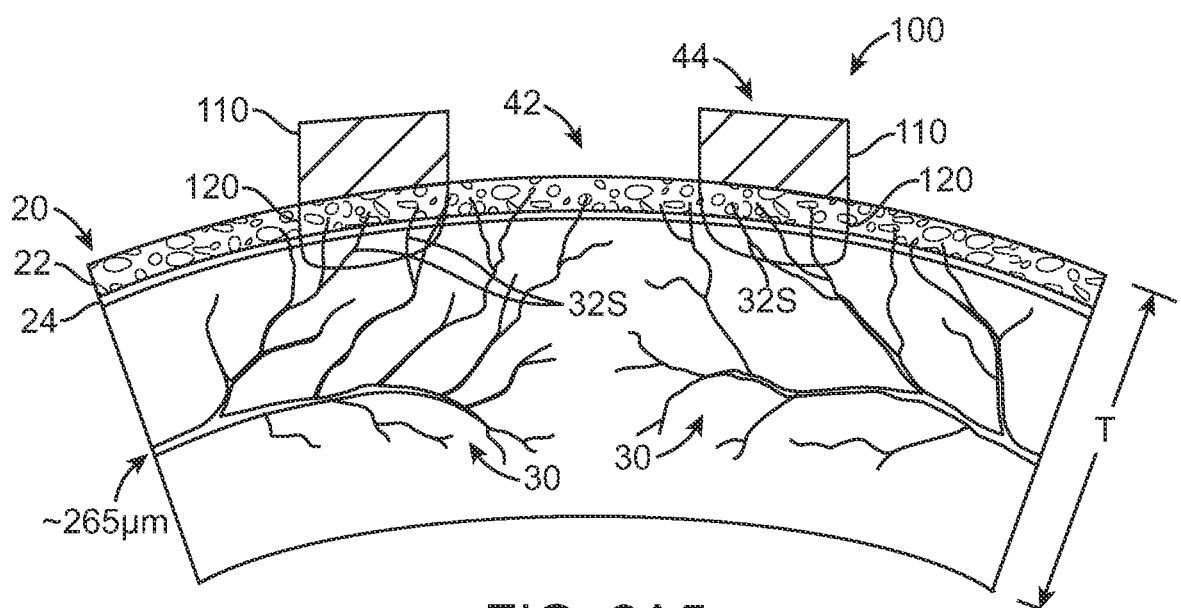
FIG. 2A5
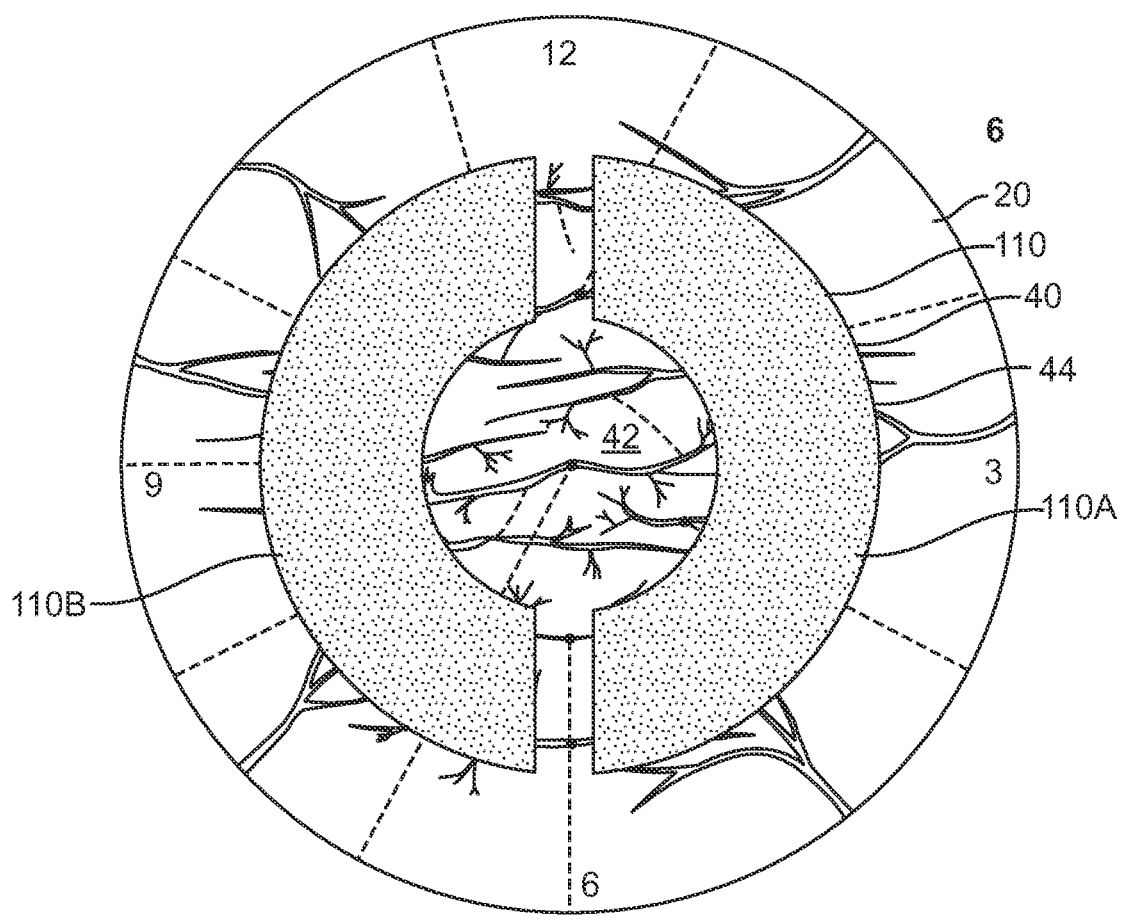
FIG. 2B5

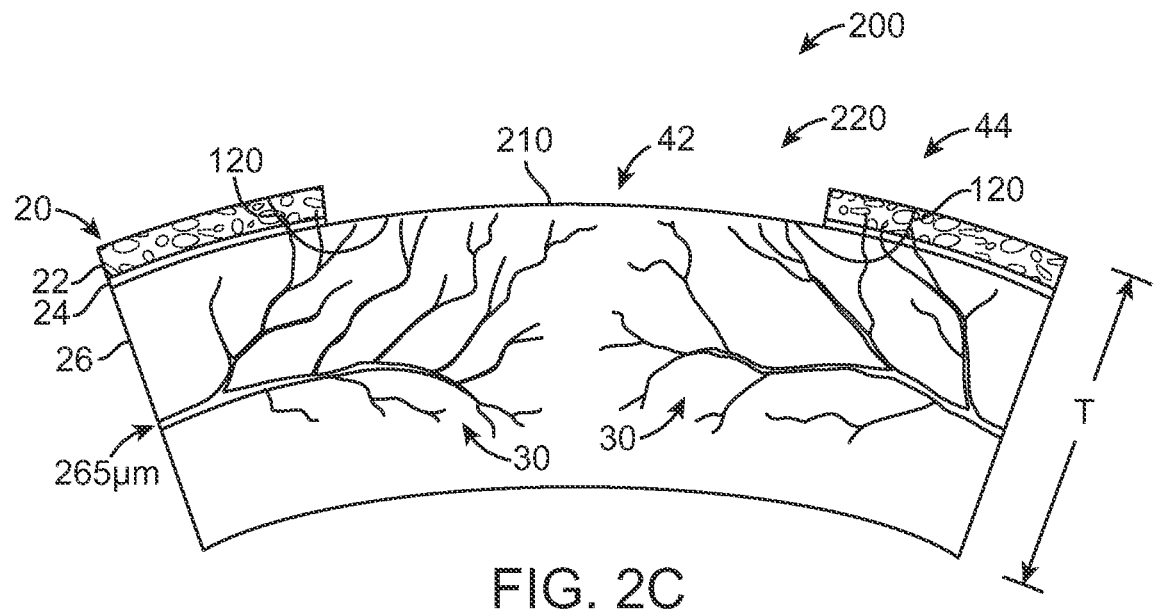
FIG. 2C
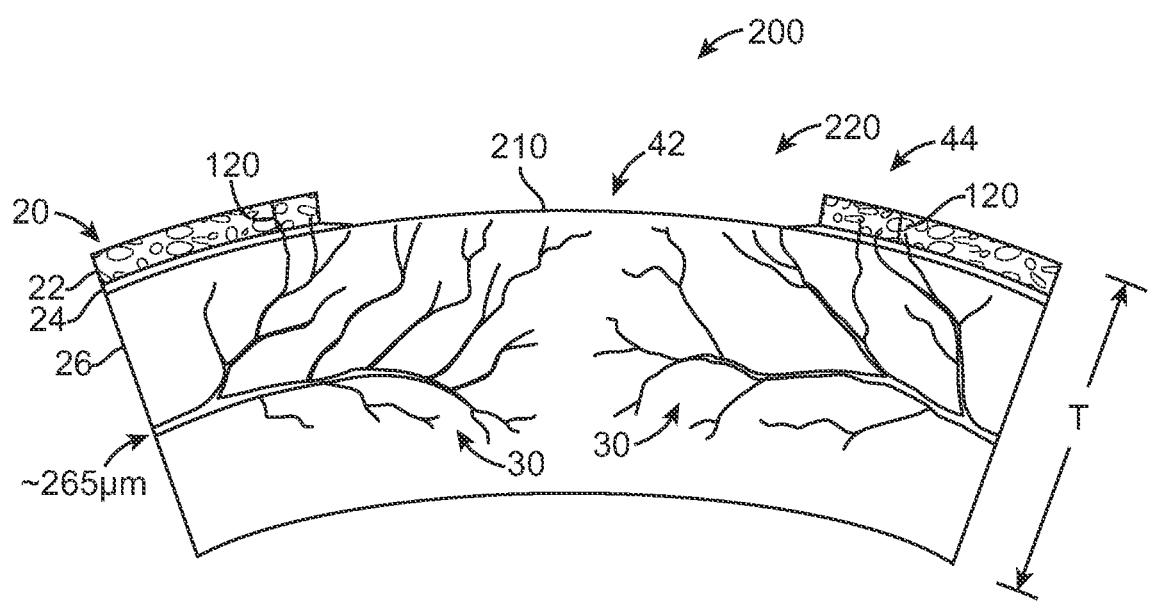
FIG. 2C1

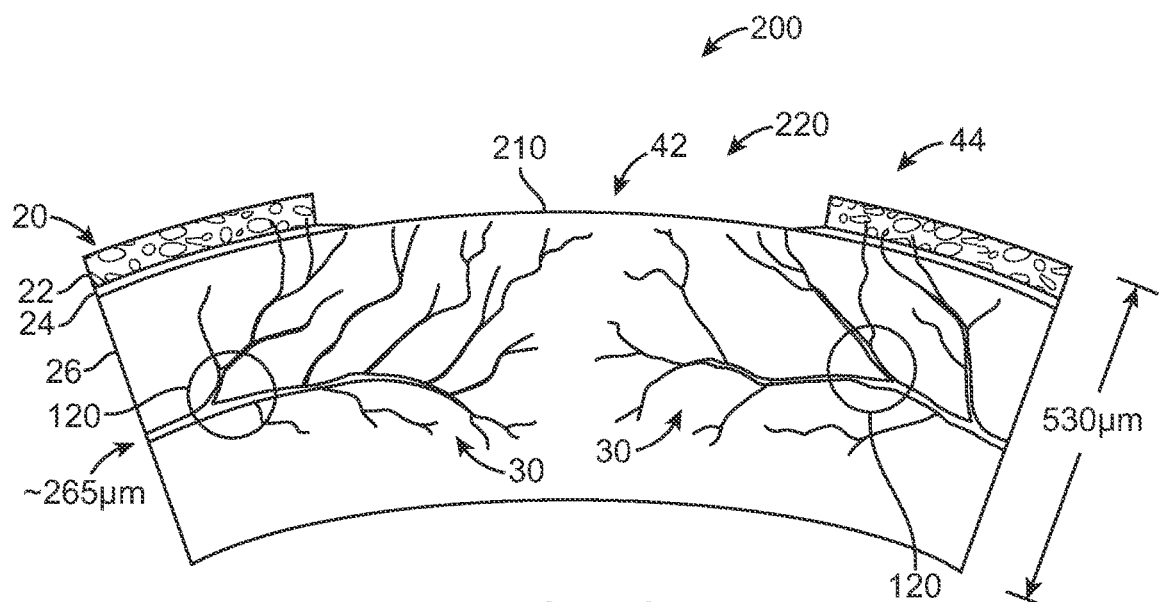
FIG. 2C2
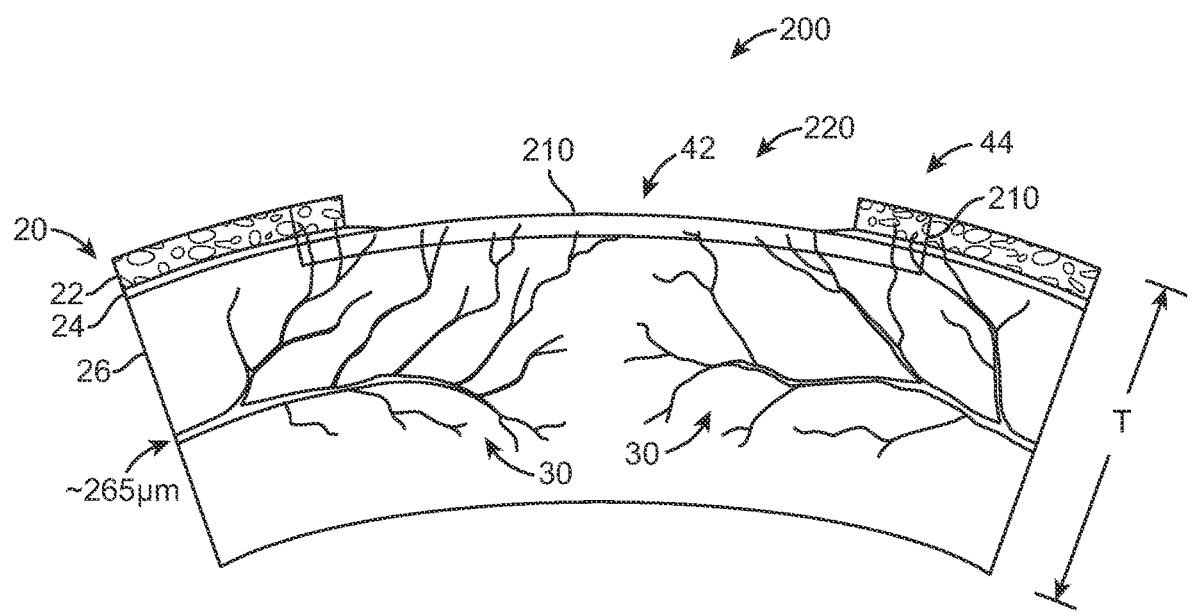
FIG. 2C3

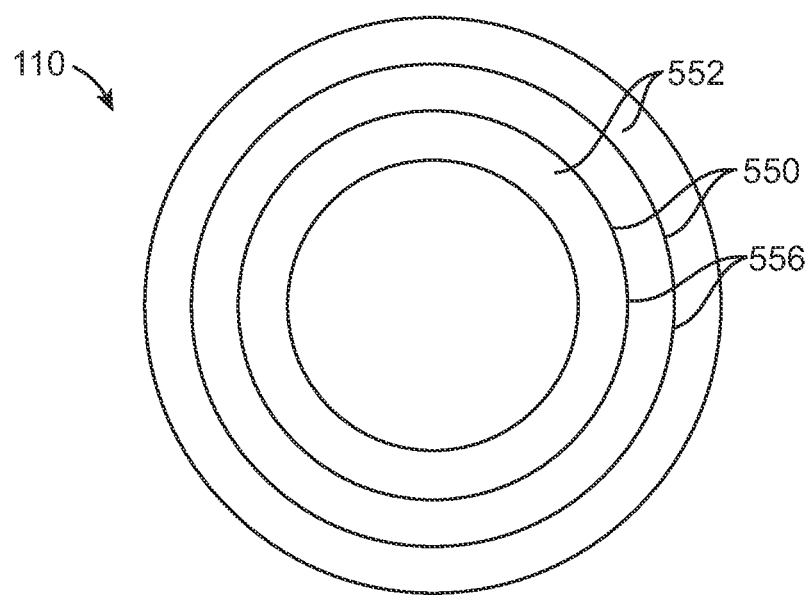
FIG. 5E1
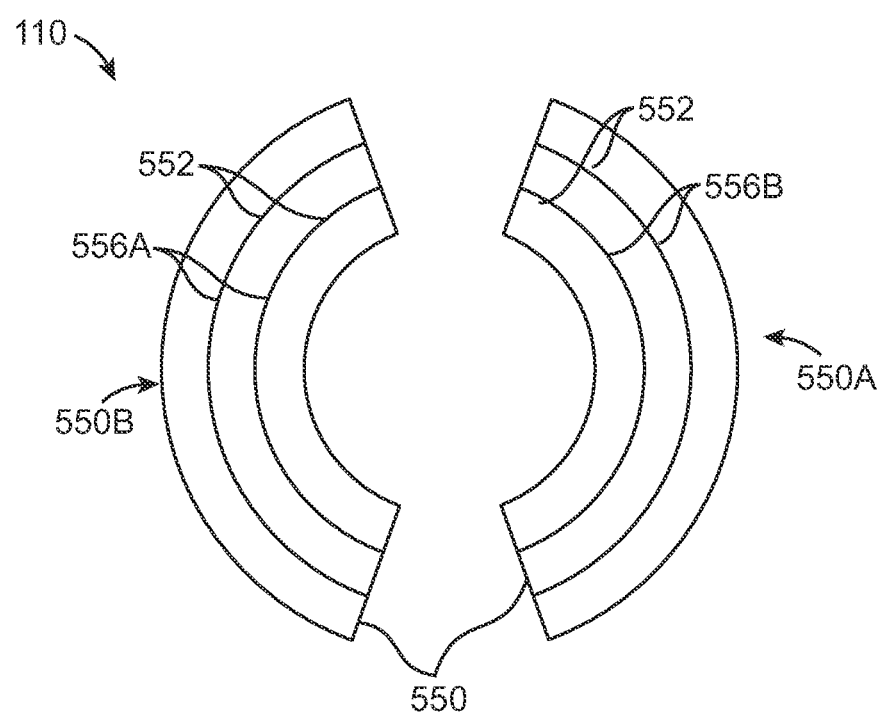
FIG. 5E2

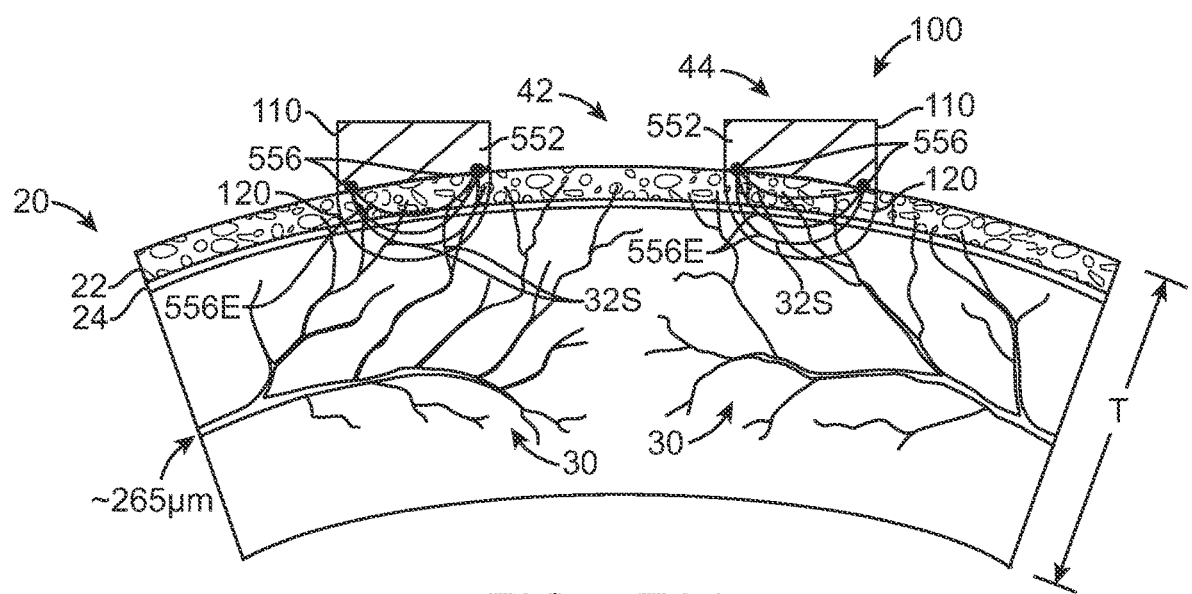
FIG. 5E3A
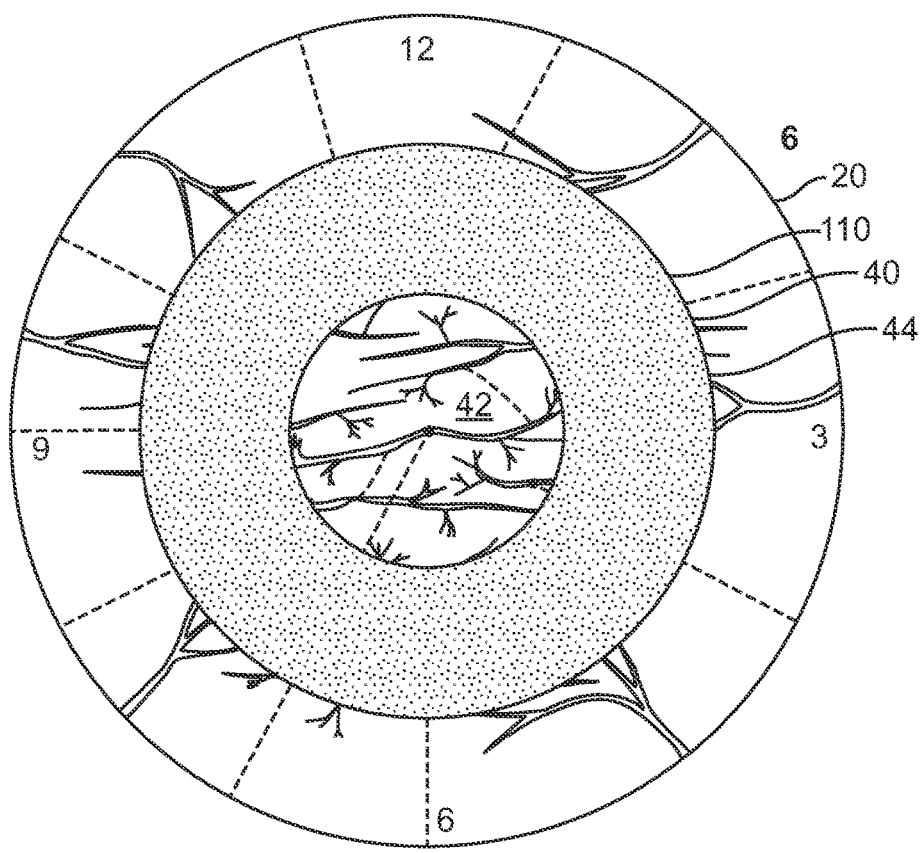
FIG. 5E3B

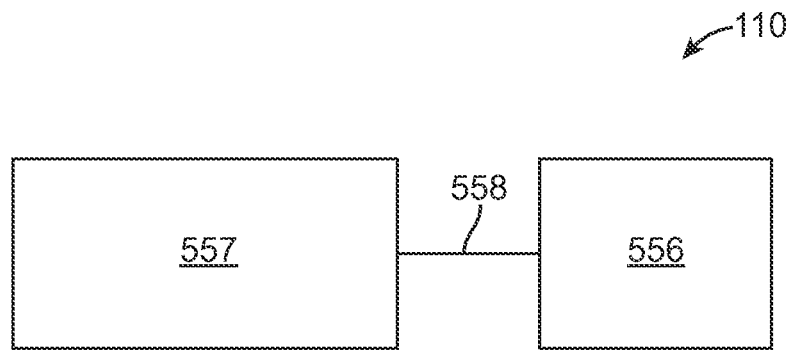
FIG. 5E4
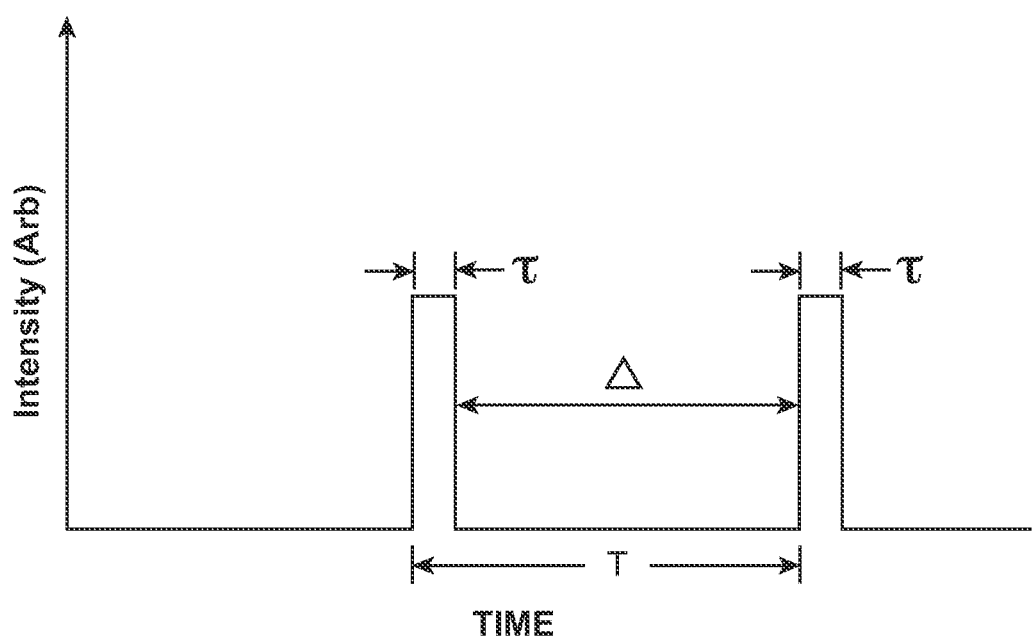
FIG. 5E5

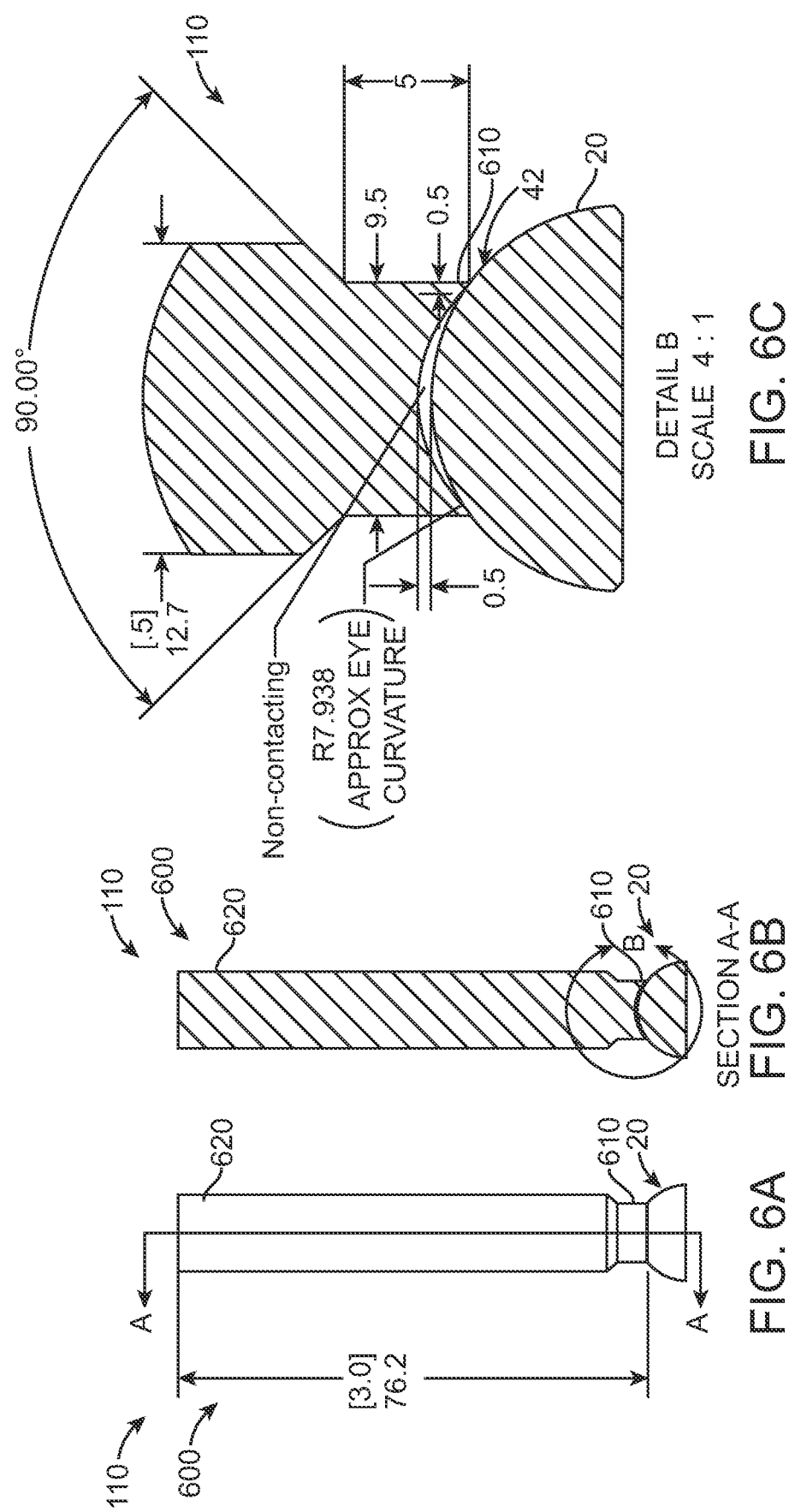

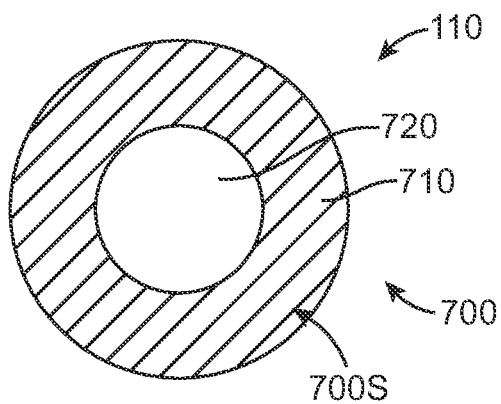
FIG. 7A
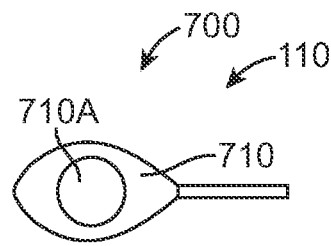
FIG. 7A1
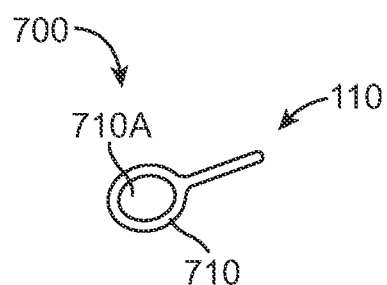
FIG. 7A2
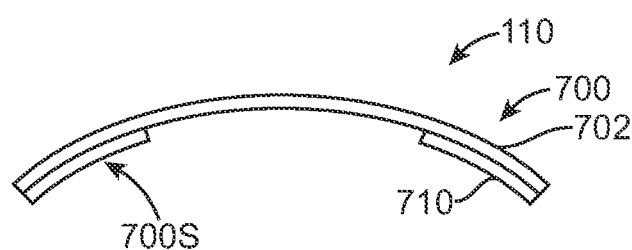
FIG. 7A3
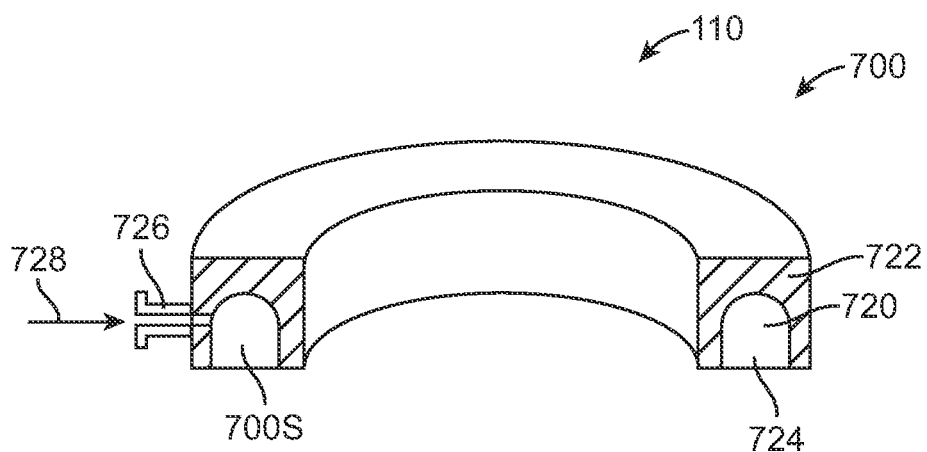
FIG. 7A4

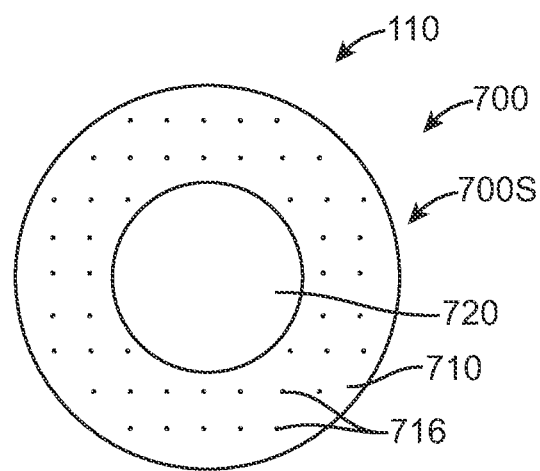
FIG. 7A5
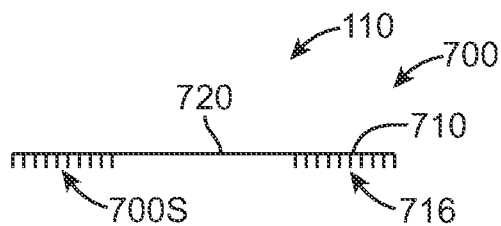
FIG. 7A6
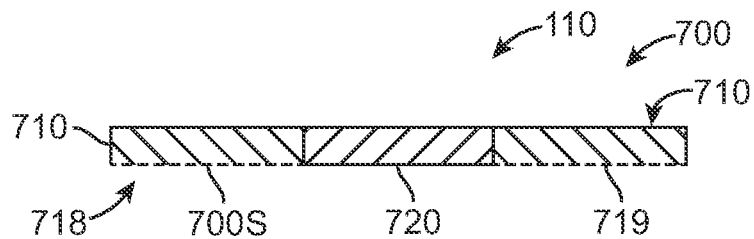
FIG. 7A7

CORNEAL DENERVATION FOR TREATMENT OF OCULAR PAIN

CROSS-REFERENCES TO RELATED APPLICATIONS

The present application is a continuation of U.S. application Ser. No. 13/503,841 filed on Aug. 20, 2012, which is the National Stage of International Application No. PCT/US2010/53854 filed on Oct. 22, 2010, which claims the benefit under 35 U.S.C. § 119(e) of U.S. Provisional Application No. 61/279,612, filed on Oct. 23, 2009. Each of the above-referenced applications is incorporated by reference in its entirety.

STATEMENT AS TO RIGHTS TO INVENTIONS MADE UNDER FEDERALLY SPONSORED RESEARCH AND DEVELOPMENT

NOT APPLICABLE

BACKGROUND OF THE INVENTION

People like to see. The eye comprises several tissues that allow a person to see, and these tissues include the cornea, the lens and the retina. The cornea and lens focus light rays on to the retina so as to form an image on the retina. The cornea comprises an outer tissue of the eye that is coupled to air with a tear film, such that a majority of the focusing power of the eye is achieved based on the shape of the cornea. The retina comprises photoreceptors that generate neural signals in response to the light image formed on the retina, and these neural signals are processed and transmitted to the occipital cortex of the brain such that the person perceives the image.

The cornea is a highly innervated tissue that comprises several layers including an epithelium disposed under the tear film and a stromal layer disposed under the epithelium. In humans and at least some animals a Bowman's membrane is disposed between the epithelium and corneal stroma. The innervation of the cornea can be useful and help the person to blink so as to replenish the tear film for vision and to maintain a healthy corneal epithelium. The innervation of the cornea can also help to protect the cornea and the persons sight with the sensation of pain, such that in at least some instances the person may be forced to protect the cornea and eye from further injury in response to a painful stimulus. However, this innervation of the cornea, may result in substantial pain following surgery in at least some instances.

Many surgeries and therapies of the eye are directed to the treatment of the cornea, and in at least some instances significant pain can occur. For example photorefractive keratectomy (hereinafter "PRK"), laser assisted in situ keratomileusis (hereinafter "LASIK"), and laser assisted epithelial keratomileusis (hereinafter "LASEK"), each reshape the cornea of the eye so as to improve the focus of images on the retina such that the patient can see better. Unfortunately, many of the corneal surgeries result in pain in at least some instances. For example, with PRK and LASEK, the epithelial layer of the cornea is removed so as to expose underlying tissue that is ablated, and in at least some instances patients experience pain when the epithelium regenerates over the ablation. With LASIK, a flap of tissue comprising the epithelium and stroma is cut with a laser or blade and opened with a hinge so as to expose the underlying stromal bed where the ablation is performed. As the LASIK flap can be positioned over the ablated stromal bed with stroma to stroma contact, LASIK can result in less pain for patients. However, in at least some instances LASIK can result in complications related to the cutting of the LASIK flap and the LASIK ablation of the exposed stromal bed that extends deeper into the cornea than PRK and LASEK ablations. Also, work in relation to embodiments of the present invention suggests that the cutting of corneal nerve fibers with the LASIK flap can result in decreased corneal sensitivity for an extended time in at least some instances. Although LASIK can result in complications in at least some instances, many patients prefer the risks of LASIK to the pain of PRK.

Although the control of pain with PRK and LASEK has been proposed and implemented, many patients who undergo PRK report pain and photophobia in at least some instances during the two to four day period when the epithelium regenerates over the ablation. For example, although the use of anesthetics such as lidocaine and propa-racaine have been proposed, use of these anesthetics in amounts that significantly reduce pain may delay reepithelialization, such that the safely prescribed dosage does not sufficiently reduce pain in at least some instances. Even with the use of safe amounts of analgesics with PRK and LASEK, patients can still report undesirable pain in at least some instances. Although the systemic use of opioids such as morphine can reduce pain, the patient may be subjected to side effects of the systemic opioid medication. Therefore, there is a significant unmet clinical need to reduce pain associated with removal of the corneal epithelium, for example following PRK, such that the patient is not subjected to significant side effects.

In light of the above, it would be desirable to provide improved methods and apparatus for pain control of the eye. Ideally such methods and apparatus would be compatible with refractive surgery, such that patients can receive a safe treatment to correct vision with full recovery of corneal tissue and neural function, and decreased pain.

BRIEF SUMMARY OF THE INVENTION

Although specific reference is made to treatment of the eye with PRK, embodiments of the present invention will have application to many patient treatments where the tissue such as epithelium regenerates, for example regenerates subsequent to removal after injury or treatment of an underlying tissue.

Embodiments of the present invention provide systems, methods and apparatus for the treatment of the eye to reduce pain. The pain may originate from an inner region of a tissue such as the cornea, and the treatment can be applied to an outer region of the tissue to denervate nerves extending into the inner region so as to reduce the pain. For example, the cornea of the eye may comprise an inner region having an epithelial defect, for example a central region of the cornea having the epithelial defect. An outer portion of the cornea can be treated so as to reduce pain of the epithelial defect, for example with treatment of an outer region of the cornea peripheral to the central region comprising the defect. The outer portion of the cornea can be treated to denervate nerves extending from the outer portion to the inner portion, and the denervation of the cornea can inhibit pain for a plurality of days such that epithelial healing is substantial and not inhibited. For example, pain can be inhibited for a plurality of days when the epithelium regenerates over a debridement, such that the regeneration of the epithelium over the debridement is substantially uninhibited. The debridement may comprise a debridement of a PRK and regeneration of the epithelium may occur over the PRK ablation without substantial inhibition when the cornea is denervated for a plurality of days. The outer portion can be treated in many ways to denervate the nerve, for example with one or more of heat, cold or a denervating substance such as capsaicin. The outer portion can be treated with a tissue treatment profile, so as to allow the use of an increased amount of treatment to achieve the desired denervation with decreased side effects. The denervation of the nerve can be reversible, such that corneal innervation can return following treatment. For example, the neurons of the nerves may be stunned or desensitized to inhibit pain, or axons of the neurons of the nerves can be cleaved to inhibit pain such that the neurons can regenerate along the nerve sheathes into the inner portion. The outer portion may extend around a perimeter of the inner portion, for example so as to enclose the inner portion with the outer portion, and the outer portion may comprise many shapes such as annular shape, an oval shape or a disc.

BRIEF DESCRIPTION OF THE DRAWINGS

FIGS. 2A1 and 2B1 show denervation as in FIGS. 2A and 2B, with the a treatment profile substantially applied and localized to the epithelial layer of tissue, in accordance with embodiments of the present invention;

FIGS. 2A2 and 2B2 show denervation as in FIGS. 2A and 2B, with the a treatment profile substantially comprising the epithelial layer and extending substantially into the stroma so as to encompass nerve bundles, in accordance with embodiments of the present invention;

FIGS. 2A3 and 2B3 shows denervation as in FIGS. 2A and 2B, with the a treatment profile localized substantially to the stroma so as to encompass nerve bundles, in accordance with embodiments of the present invention;

FIGS. 2A4 and 2B4 shows denervation as in FIGS. 2A and 2B, in which the an inner region is denervated with the outer region, in accordance with embodiments of the present invention;

FIGS. 2A5 and 2B5 shows denervation as in FIGS. 2A and 2B, in which the an inner region is denervated with the outer region comprising a first outer region and a second outer region, in accordance with embodiments of the present invention;

FIG. 2C shows an ablated cornea having an epithelial defect, in which the cornea has been denervated in accordance with embodiments of the present invention;

FIG. 2C1 shows denervation as in FIG. 2C with the denervation treatment profile comprising the epithelium extending to the debridement.

FIG. 2C2 shows denervation as in FIG. 2C with the denervation treatment profile extending to nerve bundles disposed within the stroma and peripheral to the ablation.

FIG. 2C3 shows denervation as in FIG. 2C with the denervation treatment profile extending across the ablation.

FIG. 5E1 shows an applicator as in FIG. 5A comprising at least two electrodes to deliver electrical energy to the cornea;

FIG. 5E2 shows an applicator as in FIG. 5A comprising at least two electrodes to deliver electrical energy to the cornea with a first nasal portion of the applicator and a second temporal portion of the applicator.

FIGS. 5E3A and 5E3B show an applicator as in FIG. 5E2 positioned on a cornea so as to define treatment profile 120 with the electrode fields from the spacing of the electrodes and the profile of RF pulses.

FIG. 5E4 shows circuitry coupled to applicator so as to generate the profiled RF pulses and treatment profile.

FIG. 5E5 shows RF pulses of the circuitry;

FIGS. 6A to 6C show an applicator as in FIG. 5A comprising a metal to conduct heat from the cornea;

FIG. 7A shows an applicator as in FIG. 5A to deliver a substance to an outer portion of the cornea;

FIGS. 7A1 and 7A2 shows an applicator as in FIG. 5A comprising an annular ring with the substance disposed thereon to deliver the substance to the outer portion of the cornea;

FIG. 7A3 shows a substance coated on a support along an outer portion of the support to deliver the substance to the outer portion of the cornea;

FIG. 7A4 shows an applicator with a channel to deliver the substance to the outer portion of the cornea and a wall structure to inhibit release of the substance;

FIGS. 7A5 and 7A6 show top and side and views, respectively, of an applicator as in FIG. 7A in which the applicator comprises micro-needles to deliver the substance to outer portion of the cornea;

FIG. 7A7 shows an applicator as in FIG. 7A comprising a compartment with the substance disposed therein so as to deliver the substance to the outer portion of the cornea;

DETAILED DESCRIPTION OF THE INVENTION

Embodiments of the present invention can treat may types of pain of the eye, for example pain of the cornea, and can be used for treatment of pain corresponding to refractive surgery of the cornea. The embodiments described herein can be used to treat the eye following trauma of the eye, such as corneal abrasions, and can also be used to treat pain originating from pathology of the eye such as pseudophakic bullous keratopathy (hereinafter "PBK") or aphakic bullous keratopathy (hereinafter "ABK"). In many embodiments, the pain of the cornea corresponds to pain associated with an epithelial debridement of the cornea used in conjunction with refractive surgery. For example, with PRK, an inner portion of the cornea is defined for treatment over the pupil, and the epithelium removed from the region and the cornea ablated with a pulsed laser such as an excimer laser. The epithelium may take at least one day to heal, for example three days, and the embodiments described herein can be used to treat nerves of the cornea so as to inhibit pain experienced by the patient when the epithelium regenerates over the ablation.

Many embodiments described herein provide denervation that inhibits pain but does not significantly impact or inhibit epithelial healing.

Although previous studies on mammals and humans has indicated that corneal nerves that are injured or destroyed can regenerate, the destruction of corneal nerves such as stromal nerves may be linked to post-PRK haze, such that there may be a correlation between the development of post-PRK haze and the lack of stromal nerve regeneration. The treatment of pain control as described herein can be used to treat nerves such that the nerves can regenerate so as to restore substantially the neural function and decrease haze following PRK.

As used herein denervation of tissue encompasses deprivation of nerve activity of the tissue, for example with cutting of the nerve or blocking signals of the nerve.

Figure 1A:
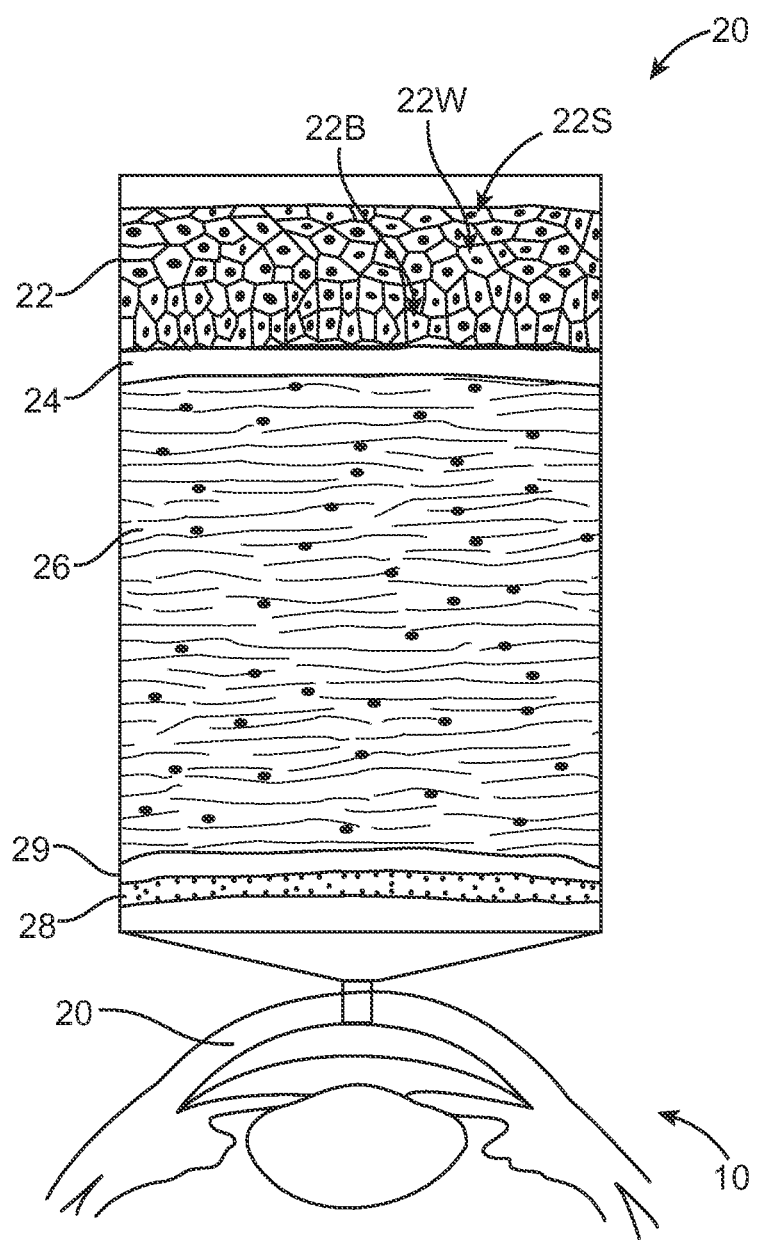
FIG. 1A shows an eye and layers of the cornea suitable for treatment in accordance with embodiments of the present invention.

FIG. 1A shows an eye, the cornea 20 and layers of the cornea suitable for treatment in accordance with embodiments. The eye comprises a cornea 22, an iris, a lens and a retina. The cornea and lens focus light on the retina. The iris defines a pupil that passes light rays, and the iris can open and close so as to adjust the pupil size in response to light so as to light to keep the amount of light striking the eye within tolerable amounts. The cornea comprises a transparent, dome-shaped structure covering the iris and pupil. The cornea refracts light that enters the eye, and can provide approximately two-thirds of the eye's refractive power.

Figure 1B:
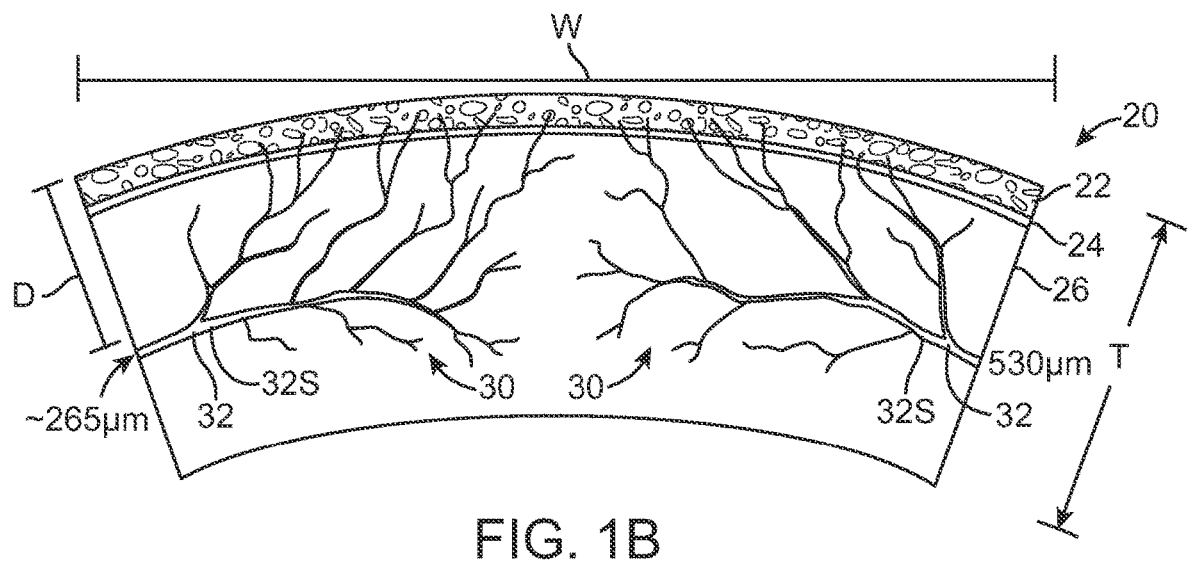
FIG. 1B shows a side view nerves of the cornea as in FIG. 1A suitable for treatment in accordance with embodiments of the present invention.
Figure 1C:
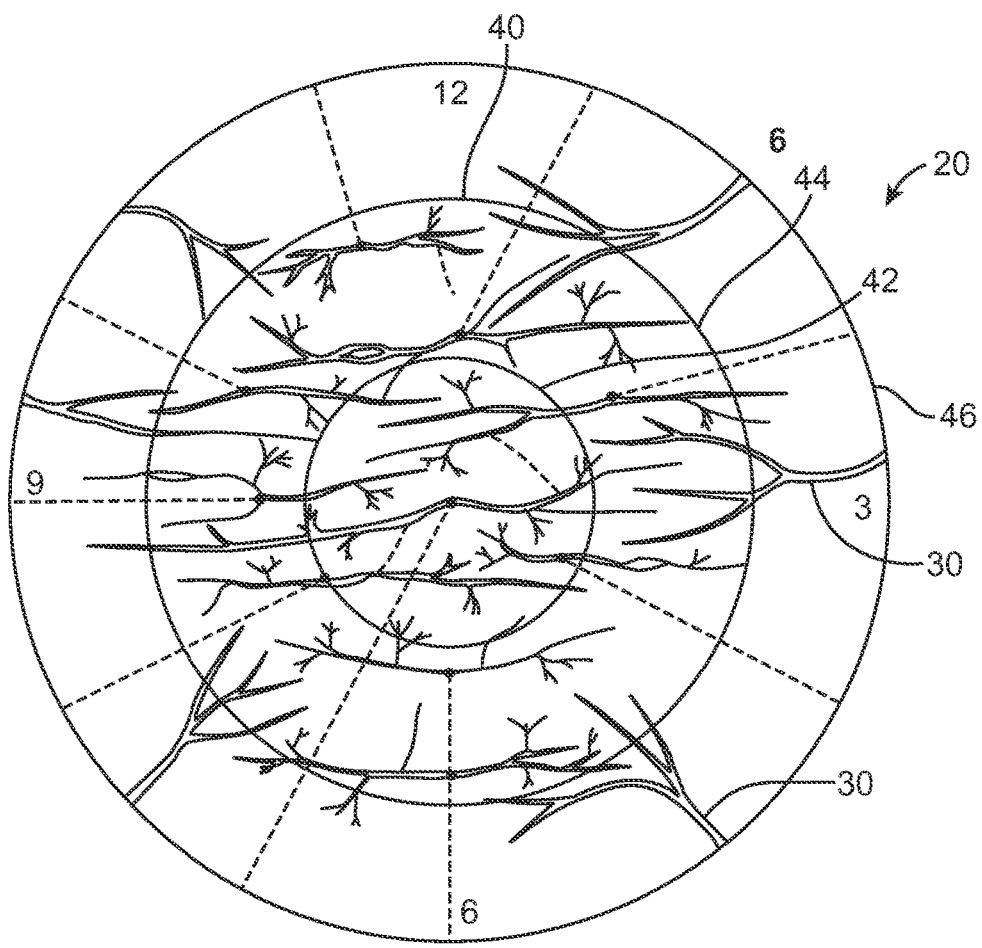
FIG. 1C shows a top view of view nerves of the cornea as in FIG. 1B suitable for treatment in accordance with embodiments of the present invention.

The cornea 20 may comprise up to five layers, depending on the species. Starting on the first tissue surface of the cornea, the epithelium 22 comprises the surface layer of cells which provide a barrier function and a smooth surface for the tear film. The epithelium 22 comprises basal columnar cells 22B, wing cells 22W disposed over the basal cells and an outer squamous protective layer 22S. Disposed under the epithelium, the second layer comprising Bowman's membrane 24 comprises a tough substantially collagenous layer disposed under the epithelium. The Bowman's membrane 24 is present in many species of primates, humans and at least some birds. The Bowman's membrane may push swelling of the cornea posteriorly towards the retina. The third layer comprising the stroma 26 comprises a substantially collagenous tissue layer composed of highly arranged collagen fibers. The stroma supports keratocytes, and forms the majority of the cornea. The fourth layer comprising Descemet's membrane 29 is an inner layer of basement membrane and plays an important role in the health of endothelial cells. The fifth layer comprises the endothelium 28, and the endothelium acts as a pump so as to regulate the liquid content of the cornea. The drying of the cornea provided by the epithelium can preserve clarity of the cornea, for example the clarity of the stroma. The endothelial pumping of water from the cornea to maintain the proper hydration and thickness of the eye is often referred to as deturgescence. A figure similar to FIG. 1A is a available on the world wide web at (http://www.aafp.org) Structure of the Cornea Corneal Innervation FIG. 1B shows a side view nerves 30 of the cornea as in FIG. 1A, and FIG. 1C shows a top view of view nerves of the cornea as in FIG. 1B. The cornea comprises a width across W of about 12 mm in the human, and a thickness T of about 550 um. The cornea is densely innervated, although the cornea is generally not vascularized. The nerves of the cornea can be located at a depth D within the cornea, for example a depth of about 265 um, although the depth can vary. The nerves 30 of the cornea bifurcate at bifurcations 32. The nerves of the stroma and Bowman's membrane comprise sheath 32S on each side of the bifurcation, and each of the nerves 30 comprises sheath 32S that extends along the nerve on each side of the bifurcation. The sheath 32S of each nerve can extend along the nerves throughout the stroma and Bowman's membrane, such that the sheath 32S can extend upward into the epithelium. Radially-oriented nerve bundles originating from the trigeminal nerve enter the cornea through the sclera. The cornea comprises nerve bundles. The nerve bundles are located substantially in the stroma and run parallel to the collagen bundles; the nerve bundles include nuclei of Schwann cells. The nerve bundles can be suitable for treatment so as to denervate the cornea and inhibit pain. As can be seen with reference to FIG. 1C, the large nerve fibers entering the cornea run substantial in the 9-3 hours direction. After the first bifurcation, they nerve fibers run in the 12-6 hours direction, and after the second bifurcation the nerves can run in the 9-3 hours direction again. A figure similar to FIG. 1C can be found in Muller-Architecture of Human Cornea p. 991 (Müller L J, Vrensen G F J M, et al. Architecture of human corneal nerves. (1997). Invest Ophthalmol Vis Sci. 38:985-994, 991.)

The cornea comprises regions that can be useful for treatment in accordance embodiments as described herein. For example the cornea may comprise a region 40 suitable for treatment, and the region 40 may comprise an inner portion 42 and an outer portion 44. A region outside region 40 may comprise an outer region 46 of the cornea that can extend to the limbus. Treatment of an outer region or portion can result in denervation of the corresponding inner region or portion of the cornea.

Figure 1D:
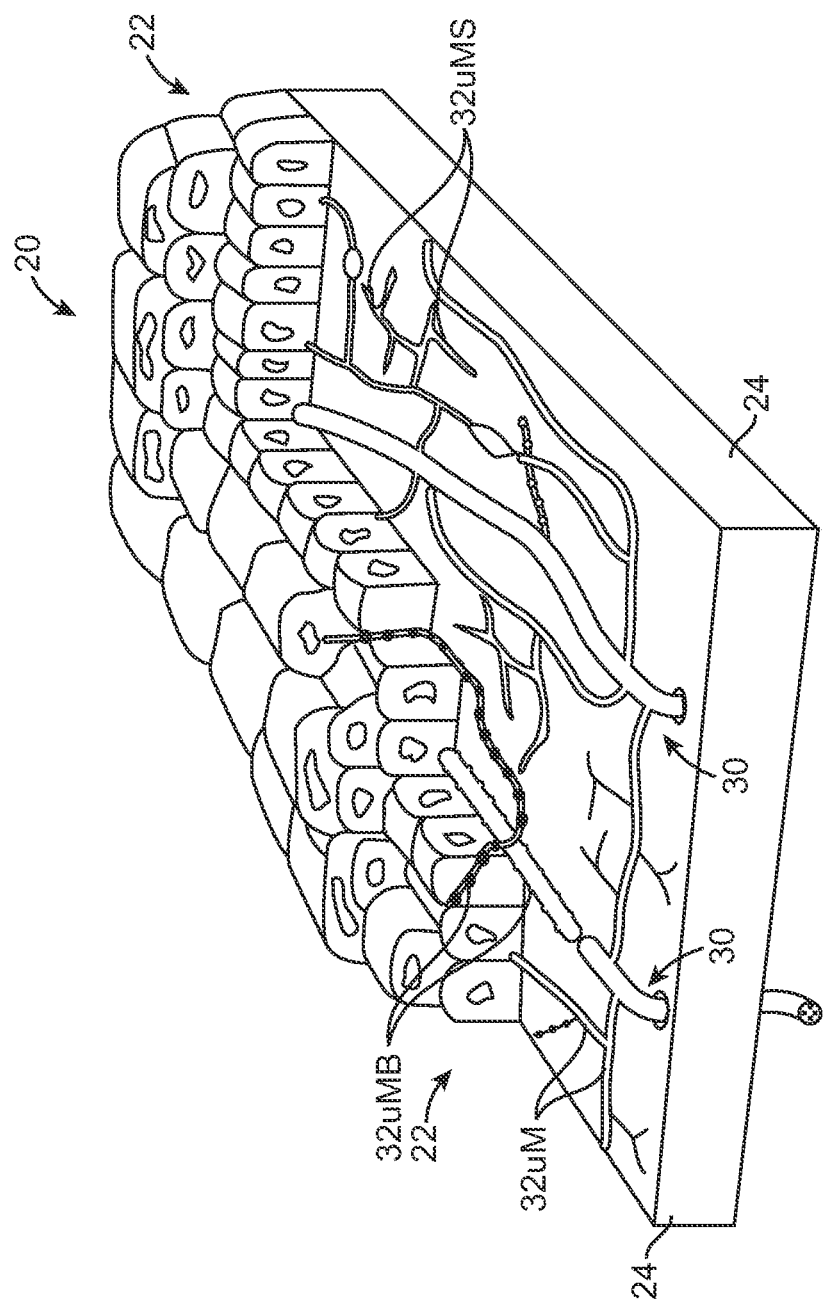
FIG. 1D shows a schematic illustration of nerves of the cornea as in FIG. 1C extending from the stroma through Bowman's layer into the epithelium and suitable for treatment in accordance with embodiments of the present invention.

FIG. 1D shows a schematic illustration of nerves 30 of the cornea as in FIG. 1C extending from the stroma through Bowman's layer into the epithelium. This 3D illustration shows penetration and the distribution of stromal bundles into the basal plexus. The nerves 30 comprise unmylenated nerve fibers 32UM, which can have bifurcations substantially at right angles. The unmylenated nerve fibers can comprise several straight 32UMS and beaded fibers 32UMB. The beaded fibers can bifurcate obliquely and turn upward between basal cells 22B to reach wing cells 22W of the epithelium 22. Upon passing through Bowman's layer and into basal lamina, the nerve bundles make a 90° turn and separate into smaller bundles separate and single nerve fibers with nerve endings in the epithelium. The nerve endings originate from myelinated A-δ and unmyelinated C-nerve fibers. The A-δ nerve fibers that reach the Bowman's layer spread out below the basal epithelial cells. The C-nerve fibers actually penetrate the epithelium layer. Due to their size, the majority of the nerve fibers in the cornea are classified as C-nerve fibers. Further, some of the nerve fibers are beaded, while others are not. The beaded nerve fibers can turn upward, for example make the 90° turn, so as to penetrate to the level of the wing cells. A figure similar to FIG. 1D is shown in Müller L J, Vrensen G F J M, et al. Architecture of human corneal nerves. (1997). Invest Ophthalmol Vis Sci. 38:985-994, 992.

Treatment of Corneal Pain

Figure 2A:
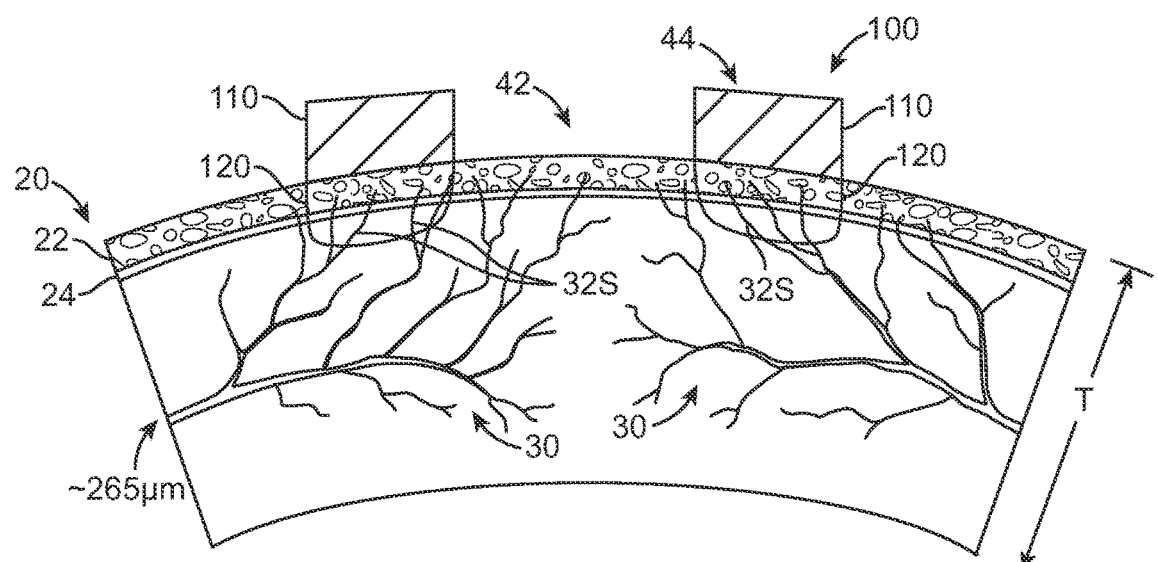
FIGS. 2A and 2B show treatment of an portion of a region of the cornea so as to denervate the cornea, in accordance with embodiments of the present invention.
Figure 2B:
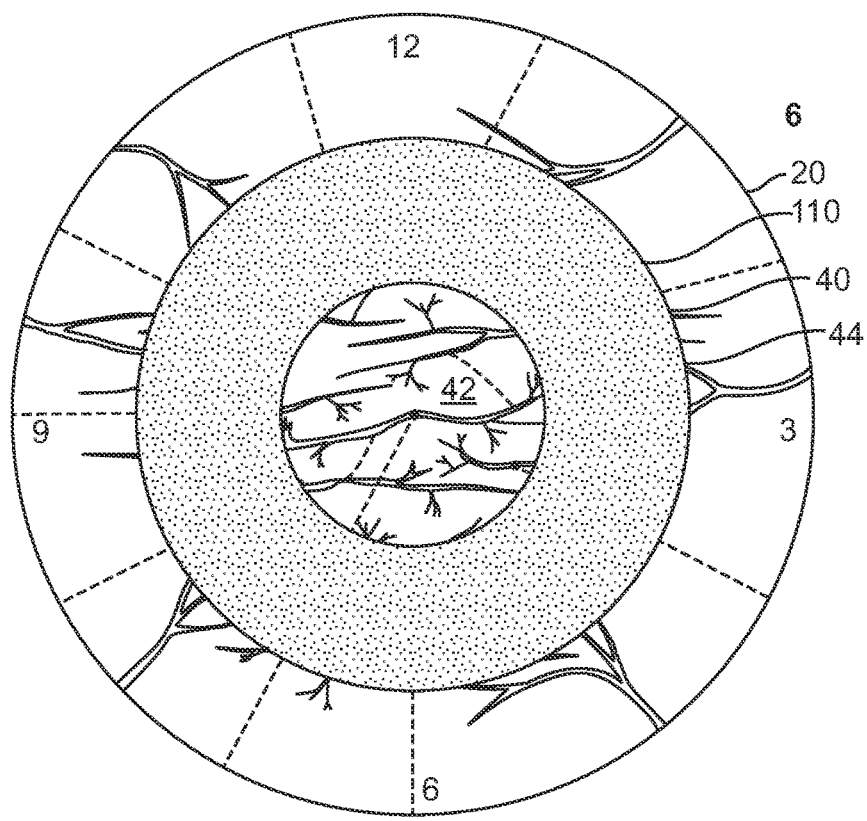

FIGS. 2A and 2B show treatment 100 of at least an outer portion 44 of a region 40 of the cornea so as to denervate the cornea. An applicator 110 can be coupled to the cornea, for example placed against the cornea or positioned so as to transmit to or receive energy from the cornea. The applicator 110 is configured to treat the cornea so as to denervate the cornea in accordance with a denervation treatment profile 120. The denervation treatment profile 120 may comprise an annular portion of the epithelium, Bowman's membrane and the underlying stroma to a depth of about 100 um. The profile 120 of denervated tissue can be determine in many ways, for example with at least one of an amount of treatment, an intensity of treatment or a duration of treatment. The denervation treatment profile 120 can decrease sensitivity of a receptor field of the nerves. The receptor field with decreased sensitivity comprises nerves of the treatment profile can extend inward from the treatment profile, for example extend centrally of the treatment profile 120.

The ability of a patient to determine the source of pain within a receptor field, for example pain from nociceptors, may not be sufficiently resolved so as to localize the pain spatially on the cornea, and the denervation of the pain receptor field sensed by the patient can extend beyond the portions of the nerves treated with treatment profile 120. For example, the treatment profile 120 can also denervate the pain receptor field sensed by the patient outward from the treatment profile, for example peripheral to the treatment profile 120.

FIGS. 2A1 and 2B1 shows denervation as in FIGS. 2A and 2B, with treatment 100 such substantially applied and localized to the epithelial layer of tissue, such that the denervation treatment profile 120 is localized substantially to the epithelial layer 22. As the nerves of the epithelium, as shown above, can extend inward, treatment of the outer portion 44 of region 40 can denervate at the inner portion 42 of the region 40.

FIGS. 2A2 and 2B2 shows treatment 100 as in FIGS. 2A and 2B, with the denervation treatment profile 120 substantially comprising the epithelial layer and extending substantially into the stroma so as to encompass nerve bundles extending along the layers of the stroma. The nerve bundles may comprise deep nerve bundles such that treatment of the outer portion 42 denervates the inner portion 44 of the region.

FIGS. 2A3 and 2B3 shows denervation as in FIGS. 2A and 2B, with the denervation treatment profile 120 localized substantially to the stroma so as to encompass nerve bundles. The denervation profile 120 can be obtained in many ways, for example with focused energy, such that the inner portion 42 of region 40 can be denervate with treatment to the outer portion 44 of region 40.

FIGS. 2A4 and 2B4 shows denervation as in FIGS. 2A and 2B, in which the an inner region is denervated with the outer region. The treatment 100 may comprise a disc shaped applicator 110, such that the denervation treatment profile 120 comprises a substantially circular portion of tissue that extends to along a cylindrical axis to maximum depth of the tissue near the center of the treatment;

FIGS. 2A5 and 2B5 shows denervation as in FIGS. 2A and 2B, in which the an inner region is denervated with the outer region comprising a first outer region and a second outer region. The treatment 100 may comprise an applicator 110 a first portion 110A and a second portion 110B, such that the denervation treatment profile 120 comprises a first outer portion of tissue and as second outer portion of tissue. Many of the nerves extending into the cornea extend substantially nasal to temporal and temporal to nasal, such that a first outer portion 110A located on a first nasally disposed portion of the cornea and a second outer portion 110B disposed on a temporally disposed portion of the cornea can treat the inner portion, for example the central portion.

FIG. 2C and shows an ablation 200 of cornea 20 having an epithelial defect 220. The ablation 200 comprises an ablation profile 210 that is shaped to correction vision of the patient. The cornea is denervated in accordance with a denervation treatment profile 120. The denervation treatment profile 120 may comprise an annular denervation treatment profile. Work in relation to embodiments as described herein related to PRK suggests that the periphery of the debrided area corresponds to pain of PRK patients, and treatment of the epithelium and cornea near the edge of the debrided area can attenuate pain in PRK patients. This suggests that perhaps little or no pain may emanates from the center of ablation profile 210 the debrided area, such that treatment of the outer portion 44 of region 40 can be sufficient to inhibit pain from the inner portion 42.

The temporary depravation of nerve supply in accordance with denervation profile 120 can be used to mitigate post-PRK and corneal pain, and may comprise the temporary deprivation of a nerve supply. The corneal denervation may last for a for a few days, and can include one or more of stunning the corneal nerves, increasing the threshold the corneal nerves, inhibiting the corneal nerve signals, or completely blocking the corneal nerve signals, so as to allow reduced pain when the epithelium regenerates and until the epithelium heals.

Work in relation to embodiments related to corneal pain suggests that it may be advantageous to cause a temporary denervation of nerves at the edge and/or the whole portion of the debrided area so as to reduce post-PRK pain. Similar denervation can be used with pain originating from other traumatic, surgical or other causes of corneal surface disruption. The pain may originate from nerve endings at the wound edge or from the area along the periphery of the debrided area.

In many embodiments as described herein, at least the sheath 32S of each nerve remains substantially intact along the portions of the nerve extending through the stroma and Bowman's membrane, such that the nerves can regenerate along the sheath so as to restore enervation.

FIG. 2C1 shows denervation as in FIG. 2C with the denervation treatment profile 120 comprising the epithelium extending to the debridement and wherein the denervation treatment profile is localized substantially to the epithelium 22. As noted above, the treatment of the outer portion 44 can inhibit pain of the inner portion 42.

FIG. 2C2 shows denervation as in FIG. 2C with the denervation treatment profile 120 extending to nerve bundles disposed within the stroma and peripheral to the ablation. The denervation treatment profile 120 may be localized to the stroma 26 in many ways, for example with focused energy, such that the inner portion 42 is denervated with treatment of the outer portion 44.

FIG. 2C3 shows denervation as in FIG. 2C with the denervation treatment profile 120 extending across the ablation 200.

The denervation treatment profile 120 can be used for denervation for mitigating pain after PRK, and the denervation profile 120 may comprise one or more of increasing nerve stimuli threshold, desensitizing the nerve with a desensitizing agent, stunning the nerve, substantially inhibiting the corneal nerve signals, completely blocking the corneal nerve signals, pruning the nerve or pruning the axons of the nerve without substantially pruning the sheath of the nerves.

Figure 3A:
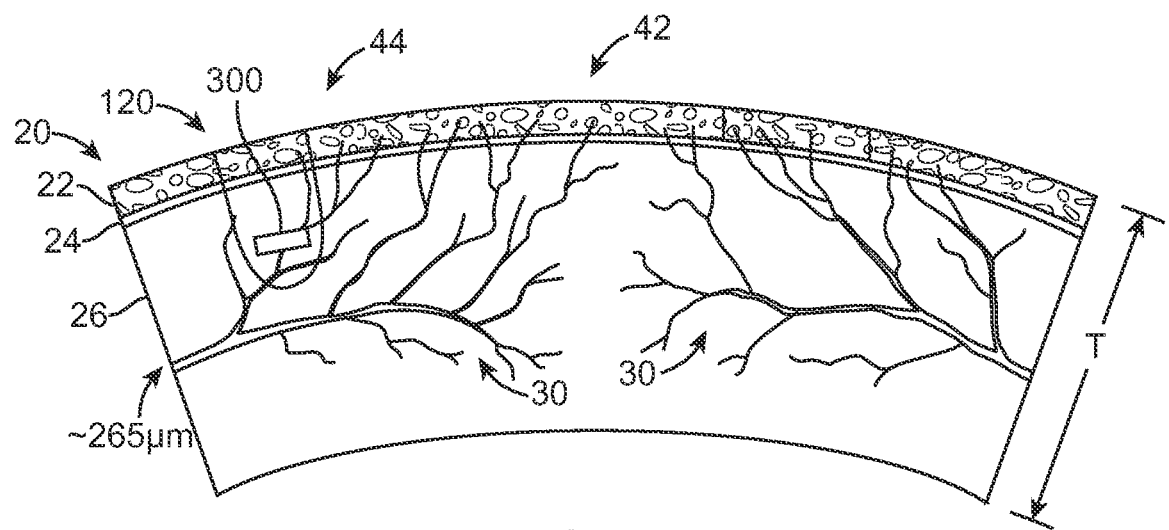
FIGS. 3A and 3B show the severing of axons disposed within a nerve such that sheath remains intact, in accordance with embodiments of the present invention.
Figure 3B:
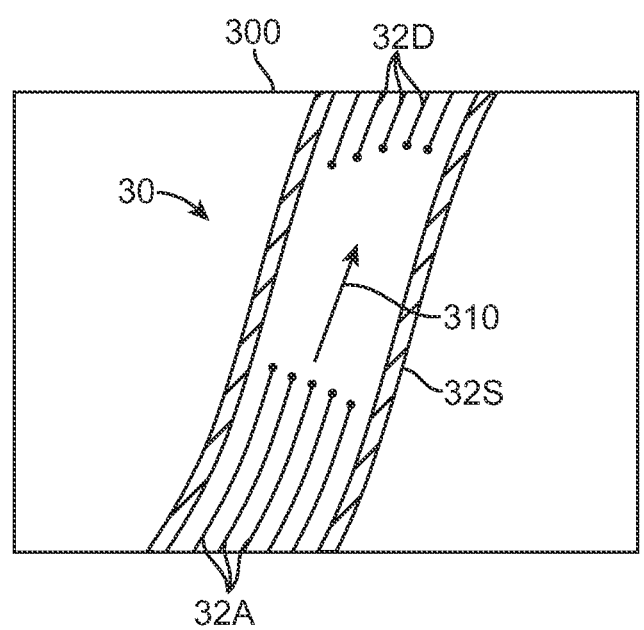

FIGS. 3A and 3B show the severing 300 of axons 32A disposed within a nerve such that sheath 32S remains intact. The denervation treatment profile 120 can be configured such that the nerve sheath remains intact when the axons are severed, as the threshold for severing the axons of the nerve can be lower than the threshold for severing the sheath. The severing 300 of axons 32A results in dead portions 32D of the axons that are replaced with regeneration of the axons 32A. The regeneration occurs along a path 310 defined by the nerve sheath. The severing of axons 32A may occur at many locations of the cornea, for example location 350.

Figure 3C:
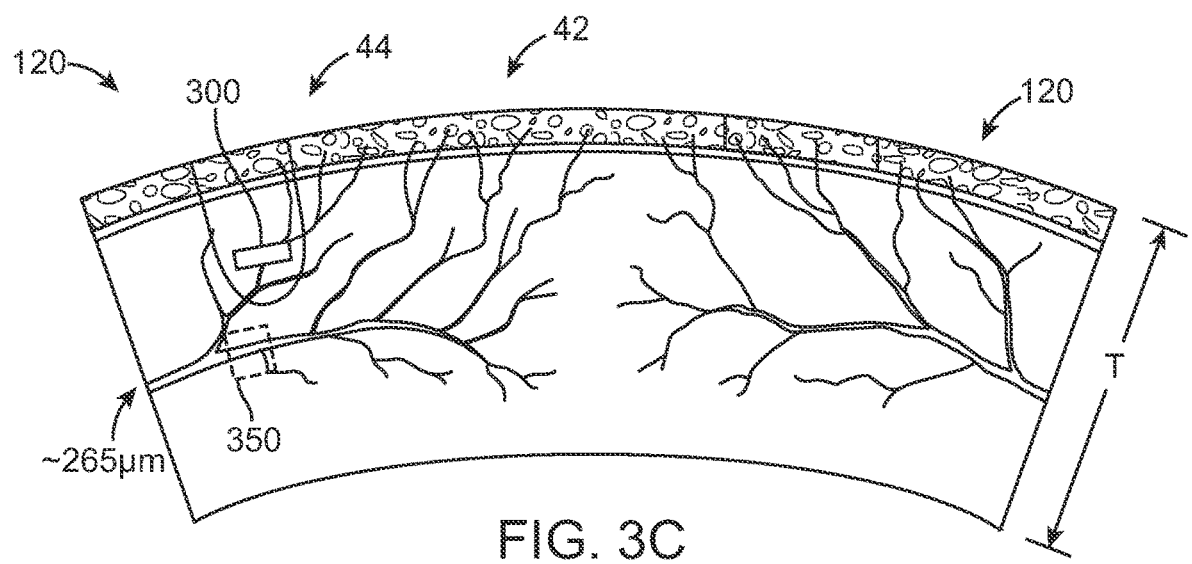
FIGS. 3C and 3D show regeneration of the axons along the sheaths subsequent to cleavage of the axons as in FIGS. 3A and 3B.
Figure 3D:
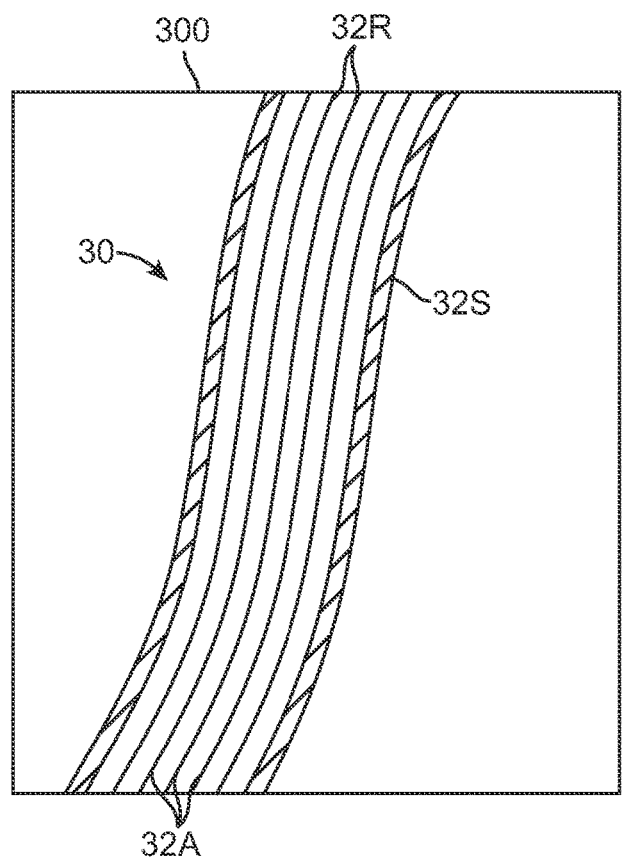

FIGS. 3C and 3D show regeneration of the axons along the sheaths subsequent to cleavage of the axons as in FIGS. 3A and 3B. The regeneration can occur along the nerve sheath upwards through the stroma to one or more of Bowman's membrane, the ablated surface, or the epithelium. As the regeneration can occur along the path of the nerve sheath, the regenerated nerve can correspond substantially to the nerve conduction path prior to severance of the axons.

Figure 4A:
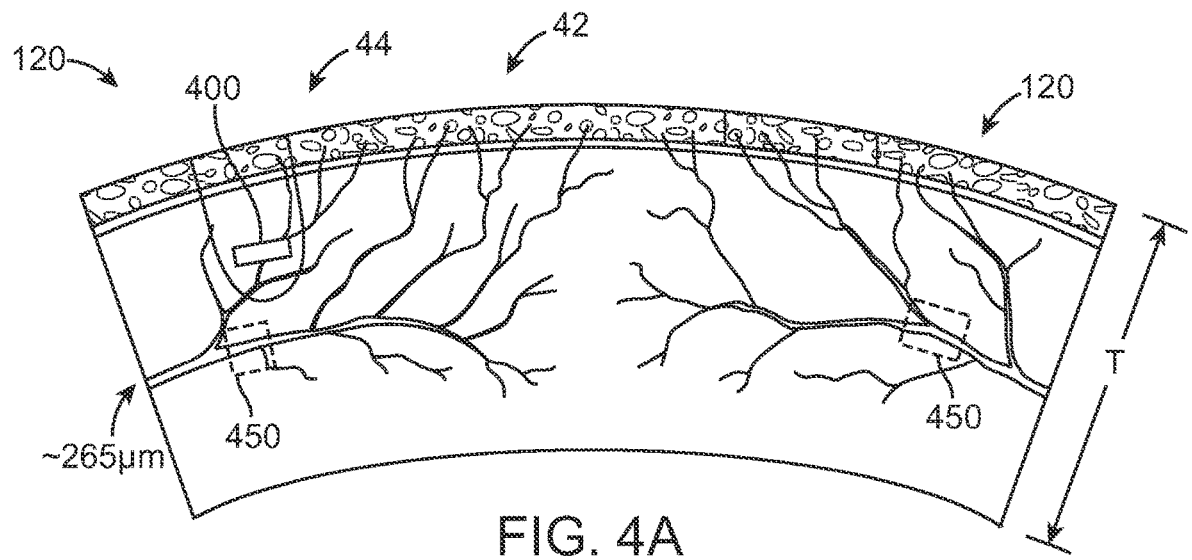
FIGS. 4A and 4B show the severing of the nerve into an inner portion of the nerve and an outer portion of the nerve, such that the sheath of the inner portion remains substantially aligned with the outer portion and axons regenerate from the outer portion along the sheath of the inner portion, in accordance with embodiments of the present invention.
Figure 4B:
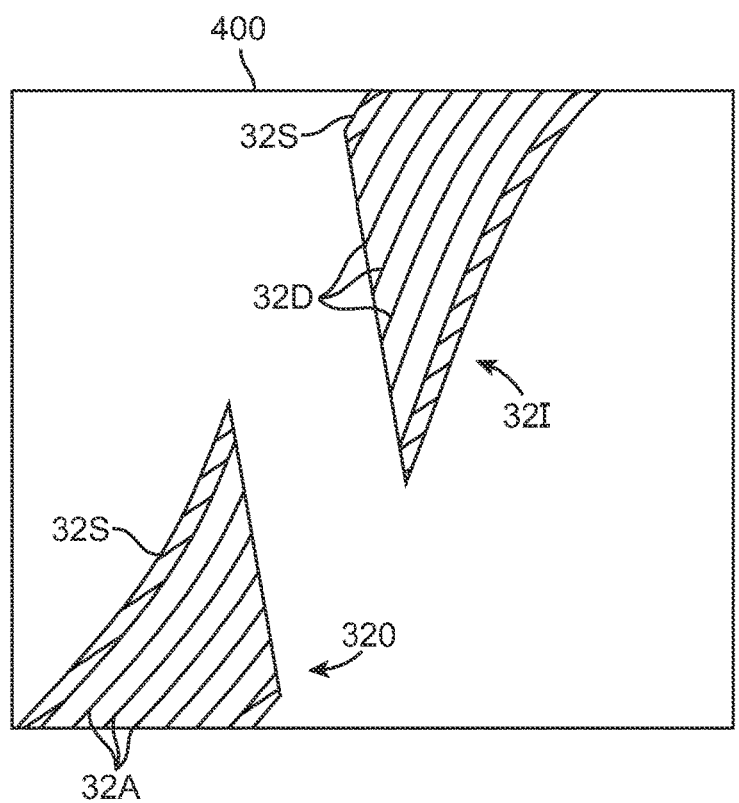

FIGS. 4A and 4B show the severing 400 of the nerve into an inner portion of the nerve 32I and an outer portion of the nerve 32O, such that the sheath of the inner portion 32I remains substantially aligned with the outer portion 32O so that axons regenerate from the outer portion along the sheath of the inner portion. When the nerve 30 is severed with sheath 32S, the axons 32A grow toward the outer portion of the sheath 32O. The dead portions 32D of the severed axons are replaced with regeneration of the axons 32A along the sheath 32S of the outer portion 32O.

Figure 4C:
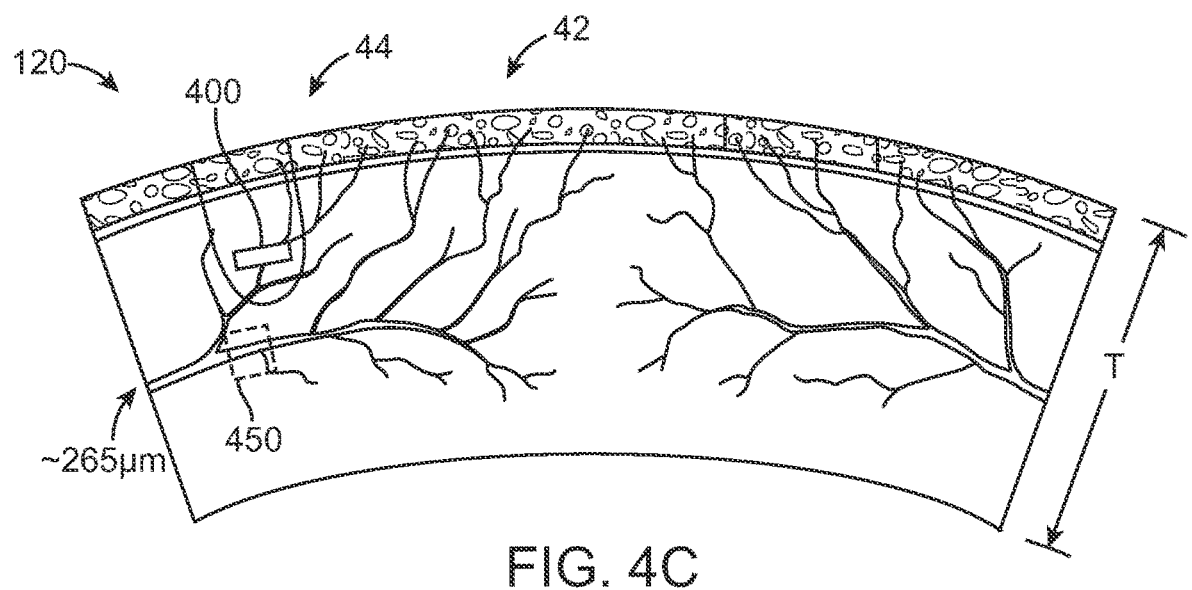
FIGS. 4C and 4D show regeneration of the axons along the inner sheaths subsequent to cleavage of the nerves as in FIGS. 4A and 4B.
Figure 4D:
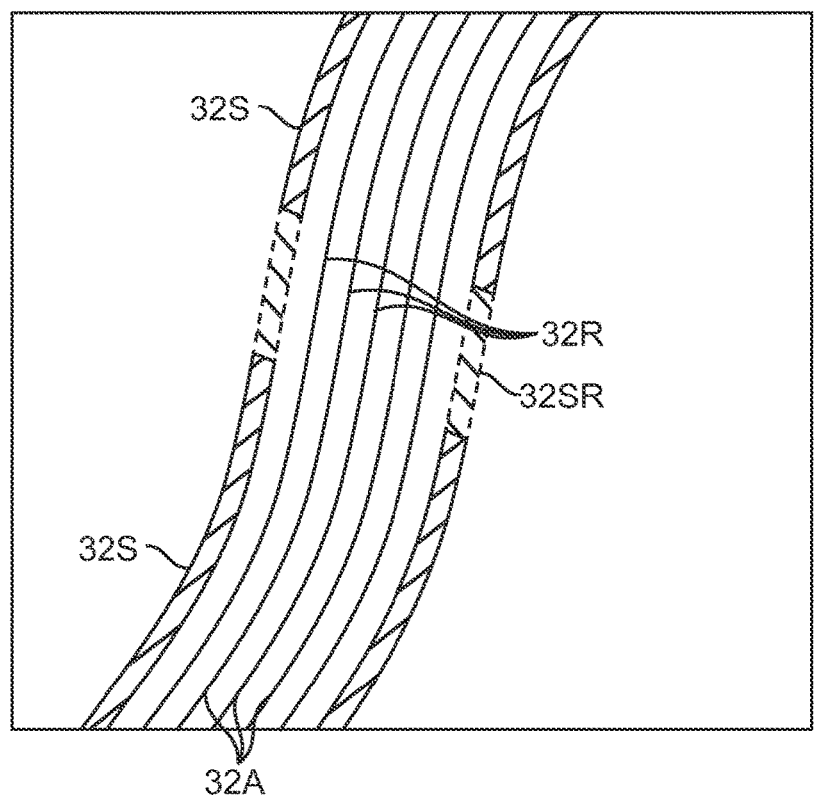

FIGS. 4C and 4D show regeneration of the axons along the inner sheaths subsequent to cleavage of the nerves as in FIGS. 4A and 4B. The axons 32A comprise a regenerated portion 32R that extends along the sheath. Work in relation to embodiments suggests that the sheath 32S may also regenerate.

Figure 5A:
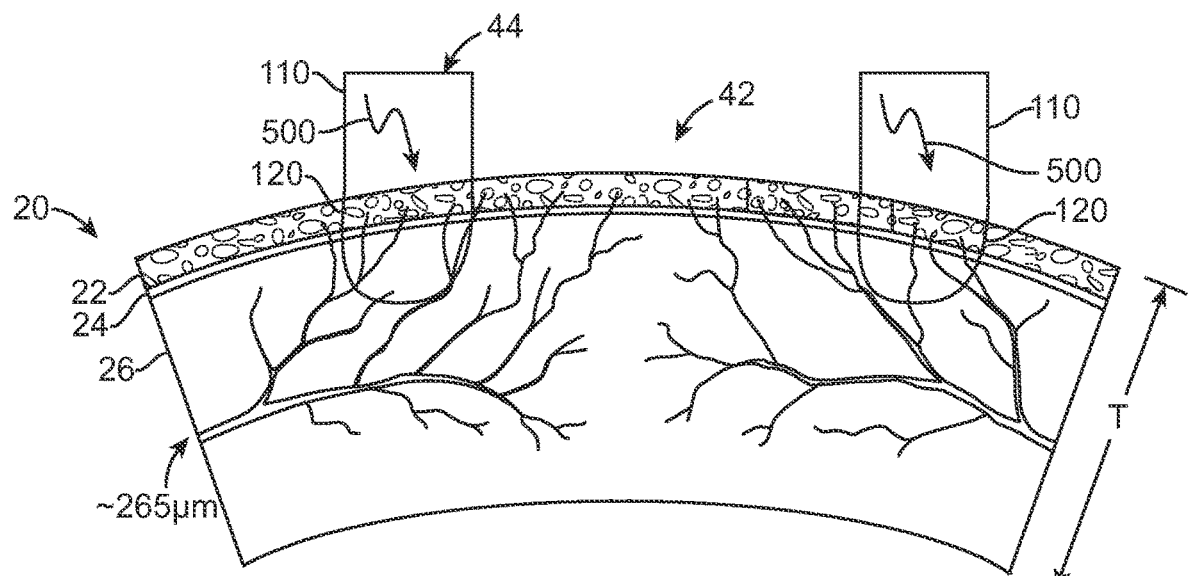
FIG. 5A shows an applicator coupled to the cornea to denervate the nerves, in accordance with embodiments of the present invention.

FIG. 5A shows an applicator 110 coupled to the cornea to treat the cornea with a denervation treatment profile 110. The applicator 110 can be used to threat the cornea before, during or after PRK, or combinations thereof. Denervation for mitigating pain after PRK may be achieved in many ways, and the denervation treatment profile 120 as described herein may encompass one or more of one or more of increasing nerve stimuli threshold, desensitizing the nerve with a desensitizing agent, stunning the nerve, destroying the nerve, pruning the nerve or pruning the axons of the nerve without substantially pruning the sheath of the nerves. The applicator 110 can be configured for interaction 500 with the cornea, so as to transmit energy to the cornea, receive energy from the cornea, or deliver at least one substance to the cornea, or combinations thereof. For example, applicator 110 can be configured to receive thermal energy from the cornea so as to cool the cornea to achieve denervation treatment profile 120. Applicator 110 can be configured to heat the cornea, for example with light or electrical current or heat conduction, so as to achieve derivation treatment profile 120. Applicator 110 can be configured to apply a substance to the cornea, for example a noxious substance such as capsaicin.

Stunning the Nerves:

Applicator 110 can be configured to stun the nerves in many ways. For example applicator 110 can be configured to stun the cornea with cooling. Applicator 110 may comprise an annular ring configuration which contacts the cornea at the outer portion 44 so as to cool the cornea to a desired temperature profile. For example an application for a given time can achieve a desired effect at desired depth within the cornea, so that nerves at different depths can be numbed selectively (depth wise). Alternatively, the applicator may comprise a disc shaped flat surface such as the end of a cylindrical rod or a cooled contact lens, such that a disc shaped portion of the cornea comprising the outer portion 44 and the inner portion 42 of the region 40 is treated.

Applicator 110 can be configured to treat the cornea with photodynamic treatment. For example, the nerves can be stained with nerve specific stains or dyes such as horseradish peroxidase. Such molecules can attach to a molecule of the nerve for photodynamic activation. The nerve and dye can be exposed to light so as to stun the nerve. The irradiation may comprise selective local, for example ring shaped, photo therapy which will stimulate the molecule to cause local damage to nerves with minimal effect on surrounding tissue. For example the ring may comprise outer region 44 stained and treated with light so as to denervate inner region 42 with minimal effect on inner region 42. The applicator 110 may comprise one or more optical elements, such as lenses, prisms, mirrors so as to form a ring of light on the cornea.

The nerves may be stunned with cooling, and applicator 110 can be configured to cool the cornea. For example, at least the peripheral portion of the region can be treated with a coolant, for example chilled BSS at 8° C. used for 3 minutes before ablation, and the cornea may be cooled a ring during the ablation. The cornea was also cooled post-PRK, to lessen pain. Work in relation to embodiments suggests that −4° C. is threshold temperature where damage to mammalian cells occurs, and cooling within a range from about −8 to about 5-6° C. for a duration can provide a transient interruption of nerve conduction, with full return of function within about 12 days. The cooling with treatment profile 120 can denervate the nerves without substantial damage to the endothelial layer of cells.

The nerves may be stunned so as to provide transient local desensitization. The stunning may comprise nerve damage in which there is no disruption of the nerve or its sheath. In this case there is an interruption in conduction of the impulse down the nerve fiber, and recovery takes place without true regeneration of the nerve fiber. This modified neurapraxia may comprise a mild form of nerve injury, for example a biochemical lesion caused by concussion or shock-like injuries to the fiber. The applicator 110 can be configured so as to provide compression or relatively mild, blunt blows, including some low-velocity missile injuries close to the nerve. The modified neurapraxia stunning may provide be a temporary loss of function which is reversible within hours to months of the injury (the average is 6-8 weeks).

Destroying of Portions of Nerves

The nerves may be pruned, such that the end portions of the nerves are destroyed, for example by pruning of the nerve at an intermediate location such that the distal portion of the nerve is killed. The killing of the distal portion of the nerve may comprise severing axons of the nerve, and the sheath may remain intact where the axons are cut or may also be severed, both of which are shown above.

The nerves may be pruned mechanically. For example, the nerve may be cut. The nerve may be cut in many ways. For example, applicator 110 may comprise a trephine to cut the cornea at the outer portion 44 to the desired depth. The trephination may comprise a peripheral cut to specific depth. The cut can be done as superficial as reaching Bowman's layer, or can be farther into the cornea. The mechanical pruning may comprise laser cutting of the cornea, for example with pulsed laser cutting such as a known commercially available femto second pulsed laser. The denervation treatment profile 120 may comprise laser cutting at with an interior cut at a specific depth, for example in the epithelium or the stroma or both, as described above.

The nerves may be pruned thermally, for example with thermal heating treatment. Applicator 110 can be configured to prune the nerves thermally. The thermal treatment may comprise heating the cornea to obtain the denervation treatment profile 120. The heating may comprise radiofrequency (hereinafter "RF") heating. The radiofrequency heating may comprise one or more of low voltage, high current, desiccation of corneal nerve tissue, denaturing of corneal nerve tissue, or destroying corneal nerve tissue. The RF heating may comprise one or more frequencies within a range from about 1 kHz to about 1 GHz, for example within a range from about 10 kHz to about 100 MHz. The heating may comprise high voltage with low current, for example so as to produce sparks. The nerves may also be pruned with plasma, for example plasma from sparks.

The nerves may be pruned with cooling. For example, applicator 110 may comprise a ring configuration which is cooled to a desired temperature. The ring at an intended temperature can be applied for a predetermined amount of time so as to achieve an effect at a specific depth with denervation treatment profile 120, so that nerves at different depths can be numbed selectively (depth wise). The applicator 110 may comprise a whole plate or a contact lens configuration.

The applicator 110 can be configured with cryogenic processing, for example −10° C. or below. The cooling induced degeneration can preserve nerve sheath when axons are severed, as described above, and thus allow restoration of nerve activity within days so to allow painless period during epithelium healing period. For example, the nerve can be frozen to a temperature which causes internal nerve damage while preserving the nerve sheath. This freezing can be done locally, for example ring shaped to the outer portion of the region 44, and the duration and the temperature of applicator can be determined prior to treatment with the applicator 110 so as to obtain the desired effect at specific areas and depths and to specific nerve layers with the denervation treatment profile 110.

The nerves may be pruned with photodynamic treatment, and applicator 110 can be configured to deliver a combination of photosensitizing dye and light energy to generate denervation treatment profile 110, and the profile can be selective to nerves when the dye is selectively attached to the axons, for example receptors of channels. Selective photodynamic injury, for example the uptake of specific dye by nerves and excitation at specific wavelength can severe at least the axons, and may sever the sheath, depending on the amount of dye and intensity of light treatment.

The nerves may be pruned with ultrasound, and applicator 110 can be configured to deliver the ultrasound energy so as to generate the denervation treatment profile 120. The ultrasound may comprise shock waves to the target tissue and applicator 110 may comprise lithotripsy circuitry and transducers modified for treatment of the cornea.

Based on the teachings described herein, a person of ordinary skill in the art can conduct experiments to determine empirically parameters of applicator 110, so as to denervate the cornea with treatment profile 120. Such as person will also recognize, applicator 110 and the use thereof can be adjusted so as to stun the nerves similar to the above configurations that can be used to prune the nerves. Similarly applicator 110 can be configured such that denervation treatment profile 120 comprises regions of stunned nerves and regions of pruned nerves, and a person of ordinary skill in the art will recognize such variations and combinations based on the teachings described herein.

Figure 5B:
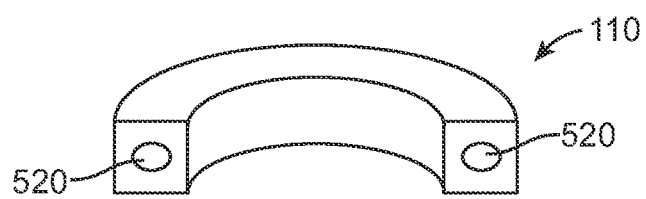
FIG. 5B shows an applicator as in FIG. 5A comprising a channel to receive a liquid to denervate the nerves.

FIG. 5B shows an applicator 110 as in FIG. 5A comprising a channel 520 to receive a liquid to denervate the nerves. The liquid may comprise a warm liquid to heat the cornea or a cool liquid to cool the cornea.

Figure 5C:
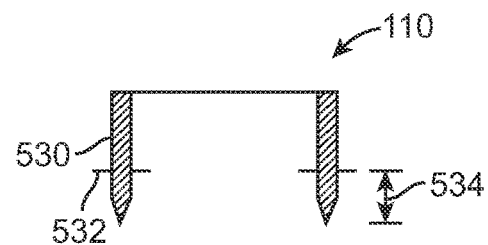
FIG. 5C shows an applicator as in FIG. 5A comprising a trephine configured with the flange to denervate the nerves.

FIG. 5C shows an applicator as in FIG. 5A comprising a trephine 530 configured with the flange 532 to denervate the nerves within a predetermined depth 534. The nerves may be stunned, the axons severed and the sheath intact, or the axons and sheath severed, as described above based on the target nerves and depth 534.

Figure 5D:
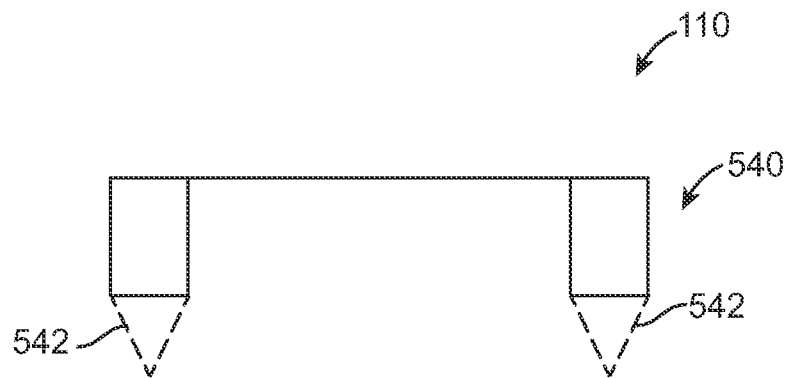
FIG. 5D shows an applicator as in FIG. 5A comprising an optical component to deliver light to the cornea.

FIG. 5D shows an applicator 110 as in FIG. 5A comprising an optical component 540 to deliver light 542 to the cornea. The light 542 can be focused to a desired treatment location and can be scanned to produce the denervation treatment profile 120.

Figure 5E:
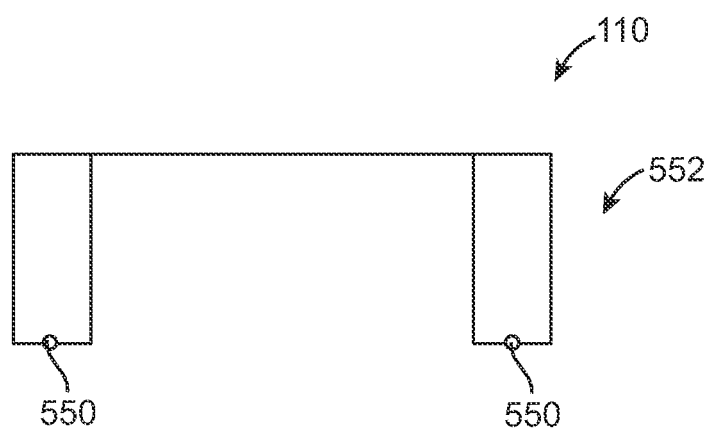
FIG. 5E shows an applicator as in FIG. 5A comprising at least one electrode to deliver electrical energy to the cornea.

FIG. 5E shows an applicator 110 as in FIG. 5A comprising an insulator 552 and at least one electrode 550 to deliver electrical energy to the cornea outer portion of the cornea disposed peripheral to the inner portion, for example central portion.

FIG. 5E1 shows an applicator as in FIG. 5A comprising at least two electrodes 556 to deliver electrical energy to the cornea. The applicator may comprise an electrode structure with the at least two electrodes shaped to define the treatment profile. For example, the electrode may comprise an arcuate shape with the electrodes spaced apart by a distance so as to define the treatment profile. The at least two electrodes can be arranged in many ways to deliver RF electrical energy in accordance with the treatment profile 120. The at least two electrodes may comprise bipolar electrodes, for example. The insulator 552, for example a dielectric material, can extend between the electrodes to define the treatment profile 120 with the spacing of the electrodes. The electrode spacing and energy to the electrodes can be configured such that there is no substantial damage to endothelial cells with treatment profile 120 to denervate the nerves.

FIG. 5E2 shows an applicator as in FIG. 5A comprising at least two electrodes 556 to deliver electrical energy to the cornea with a first nasal portion 550A of the applicator and a second temporal portion 550B of the applicator. When the first portion and second portion are substantially symmetrical, the applicator can be used on either eye, such that the nasal portion 550A can be used on the temporal portion of the opposite eye and the temporal portion 550B can be used on the nasal portion of the eye.

FIGS. 5E3A and 5E3B show an applicator as in FIG. 5E2 positioned on a cornea so as to define treatment profile 120 with the electrode fields 556E from the spacing of the at least two electrodes 556 and the profile of RF pulses. The electrodes can be spaced in many ways to achieve the desired depth penetration into tissue.

FIG. 5E4 shows circuitry 557 coupled to at least two electrodes 556 of applicator 110 so as to generate the profiled RF pulses and treatment profile. The electrodes can be coupled to the circuitry in many ways, for example with a flexible cable 558.

FIG. 5E5 shows RF pulses of the circuitry. The circuitry and RF pulses can be configured in many ways to denervate the nerve. For example, the RF energy can comprise continuous energy delivered for a period of seconds so as to heat the tissue. Alternatively or in combination, the circuitry can be configured to deliver short pulses of RF energy with a low duty cycle so as to inhibit heating of tissue. The RF energy may comprise many known frequencies and can be within a range from about 1 kHz to about 1 GHz, for example from about 10 kHz to about 100 MHz. Each pulse comprises a duration $\tau$, and the pulses can be separated by a delay $\Delta$, such the waveform comprises a period T. The frequency of the RF energy corresponds to many oscillations of the electric field per pulse. For example, the duration of the pulse can be from about 0.2 ms to about 200 ms, and the frequency can be from about 50 kHz to about 5 MHz. The duty cycle may be no more than about 10%, for example no more than about 5%, even 2% so as to inhibit heating of the tissue. For example, the pulse duration can be about 20 ms, and the delay between pulses about 48 ms, such that the pulses are delivered at about 2 Hz.

Work in relation to embodiments suggests that the electric field can produce sustained denervation without substantially heating of the nerve. A person of ordinary skill in the art can conduct experiments appropriate electrode spacing, pulse duration, frequency and duty cycle based on the teachings describe herein so as to denervate the nerve without substantial heating of the nerve with treatment profile 120. Alternatively, the nerve may be heated with the electric field and current so as to form a lesion, and a person of ordinary skill in the art can conduct similar experiments to determine appropriate parameters.

Figure 5F:
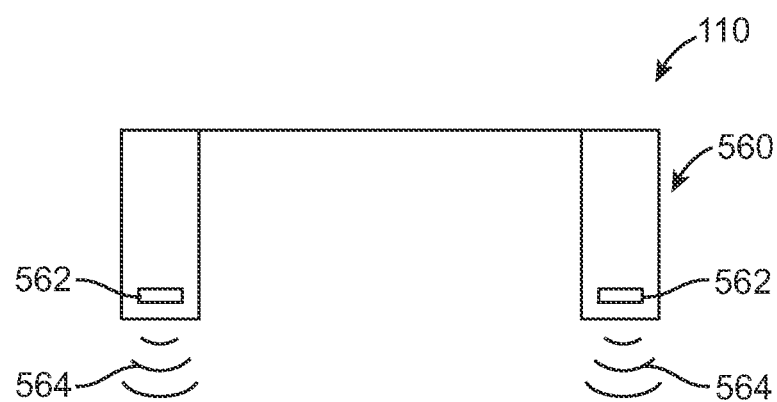
FIG. 5F shows an applicator as in FIG. 5A comprising at least one transducer to deliver energy to the cornea.

FIG. 5F shows an applicator as in FIG. 5A comprising at least one transducer to deliver energy to the cornea.

FIG. 5F shows an applicator 110 as in FIG. 5A comprising a housing 560 and at least one transducer 562 to deliver energy 564 to the cornea, for example ultrasound energy. For example, the transducer 562 may comprise ultrasound energy for sonoporation of one or more of the corneal nerves or the corneal epithelium so as to deliver the substance as described herein.

FIGS. 6A to 6C show an applicator 110 as in FIG. 5A comprising a heat conduction apparatus 600 to conduct heat to or from the cornea. For example, apparatus 600 can be heated prior to application so as to heat the cornea. Alternatively, apparatus 600 can be cooled prior to application so as to cool the cornea. Apparatus 600 comprises a handle 620 and an annular portion 620 to contact the cornea along an annular region of the cornea, such as outer portion 44. Apparatus 600 may comprise a metal with high heat capacity and conduction to cool the cornea. Apparatus 600 can be cooled to an intended temperature prior to placement, and can be placed on the cornea for an intended duration, such that the cornea is cooled with a targeted denervation treatment profile 120. The inner portion of the distal portion of the applicator can be shaped to inhibit contact with the cornea centrally when the end contacts the cornea at outer portion 42. The applicator 600 may be placed against a sphere having a radius of curvature corresponding to the cornea, for example a 7.94 mm radius of curvature.

Figure 6D:
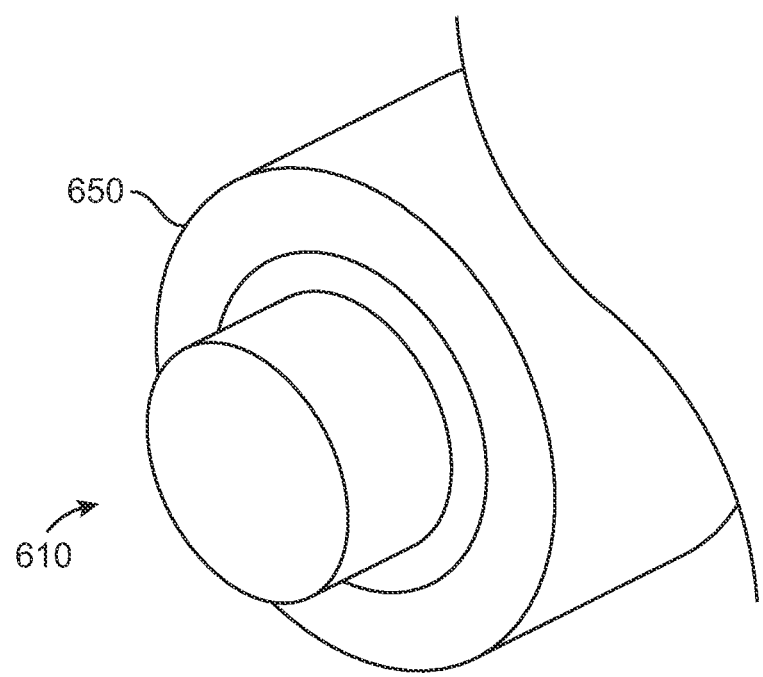
FIG. 6D shows an insulator disposed around an applicator as in FIGS. 6A to 6C.

FIG. 6D shows an insulator disposed around an applicator as in FIGS. 6A to 6C, with an insulator 650, for example silicone, disposed around an outer portion.

FIG. 7A shows an applicator 110 as in FIG. 5A comprising an apparatus 700 configured to deliver a substance 700S as described herein to an outer portion of the cornea. The apparatus 700 may comprise an outer portion 710 having the substance 700S disposed thereon and an inner portion 720, which inner portion may comprise an opening or a portion of a substrate substantially without the substance.

FIGS. 7A1 and 7A2 shows an applicator 110 as in FIG. 5A comprising apparatus 700 with outer portion 710 comprising an annular ring with the substance 700S disposed thereon to deliver the substance to the outer portion of the cornea. The outer portion 710 may define an inner aperture 710A, and a handle may extend from the outer portion.

FIG. 7A3 shows the substance coated on a support 702 along outer portion 710 so as to deliver the substance to the outer portion of the cornea.

FIG. 7A4 shows an applicator 110 with a channel 720 to deliver the substance 700S to the outer portion of the region cornea and a wall structure 722 to inhibit release of the substance. The applicator may comprise a foam portion 724 disposed therein to retain the liquid in the channel. Alternatively or in combination, a thin porous membrane can be disposed on the lower portion to the applicator to release the substance to the cornea. The apparatus may comprise a luer connector to connect the applicator to an injection apparatus 728.

FIGS. 7A5 and 7A6 show top and side and views, respectively, of applicator 700 in which the applicator comprises micro-needles 716 to deliver the substance 700S to outer portion of the cornea. The substance can be coated on the micro-needles, for example. Alternatively or in combination, the substance can be injected with the micro-needles. The micro-needles may comprise a length extending from a base located at the support to a tip, and the length can be sized to deliver the substance to a target location. For example, the length of the micro-needles may comprise no more than about 50 um to deliver the substance to the epithelium. Alternatively, the micro-needles may comprise a greater length to extend into the stroma.

FIG. 7A7 shows applicator 700 comprising a compartment 718 with the substance 700S disposed therein to deliver the substance to the outer portion of the cornea. The substance 700S can be contained in the compartment as a liquid, for example a liquid having a concentration of the substance. A porous membrane 719 can extend on toward the outer region of the cornea to deliver the substance. The compartment 718 may comprise an annular compartment. A wall can extend substantially around an inner perimeter of the compartment and an outer perimeter of the compartment. For example, the wall can extend around outer perimeter of an annulus and the inner perimeter of the with an annular portion extending therebetween along an upper surface, with the porous membrane 719 disposed along the lower surface.

Figure 7B:
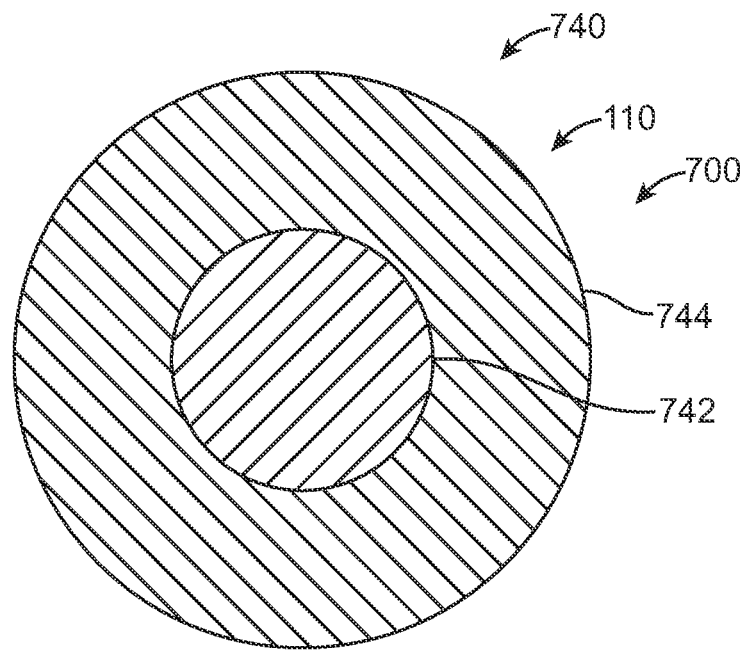
FIG. 7B shows an applicator as in FIG. 5A to deliver a substance to an inner portion of the cornea.

FIG. 7B shows an applicator as in FIG. 5A to deliver a substance to an inner portion of the cornea. The applicator 740 comprises an inner portion 742 having the substance disposed thereon. The applicator comprises an outer portion 744 substantially without the substance. The applicator 740 can be applied to the epithelium before PRK over the intended ablation zone. Alternatively, the applicator 740 can be applied to the ablated stroma after ablation with direct applicator to ablated nerve contact, for example with direct contact of a noxious substance such as comprising capsaicin to nerve comprising a cation channel which mediates stimuli.

Figure 7C:
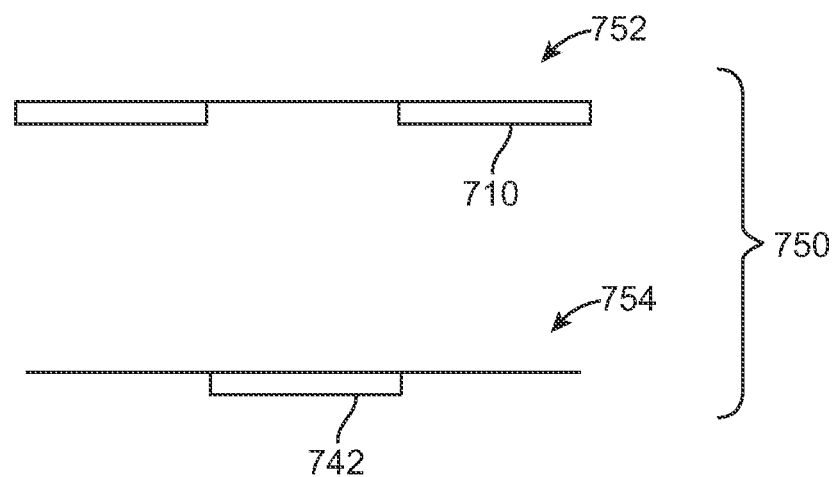
FIG. 7C shows an apparatus comprising applicators as in FIGS. 7A and 7B to deliver a first substance to the inner portion and a second substance to the outer portion of the region of the cornea to denervate the cornea, in accordance with embodiments of the present invention.

FIG. 7C shows an apparatus 750 comprising applicators as in FIGS. 7A and 7B to deliver an inner substance to the inner portion and an outer substance to the outer portion of the region of the cornea to denervate the cornea. The apparatus 750 comprises an inner applicator 752 to apply an inner substance to the inner region and an outer applicator 754 to apply an outer substance to the outer region. Work in relation to embodiments suggests that such combination of substances can be beneficial to obtain the denervation treatment profile as described herein. For example, the substance of the inner portion may comprise a noxious substance such as capsaicin or a capsaicin analog, and the outer portion may comprise an anesthetic such as a calcium channel blocker. Alternatively, the substance of the outer portion may comprise the noxious substance such as capsaicin or a capsaicin analog, and the inner portion may comprise the anesthetic such as a calcium channel blocker. This separation of the calcium channel agonist from the calcium channel blocker can allow the agonist to effect the nerves substantially without inhibition from the calcium channel blocker.

The inner applicator 752 may be applied to the cornea before the outer applicator 754. Alternatively, the outer applicator can be applied to the cornea before the inner applicator. For example the outer applicator 754 can be applied to cornea with an anesthetic comprising a calcium channel blocker before the inner applicator 752 is applied. The outer applicator 754 comprising the calcium channel blocker can be removed when a sufficient amount of calcium channel blocker has been delivered to the cornea. The inner applicator 752 comprising the noxious substance, for example a calcium channel agonist such as capsaicin, can be applied to cornea to release the agonist to the inner portion without substantial inhibition from the blocker that has been previously applied to the outer region. The inner applicator 752 can then be removed. The eye may then be ablated with PRK.

Figure 7D:
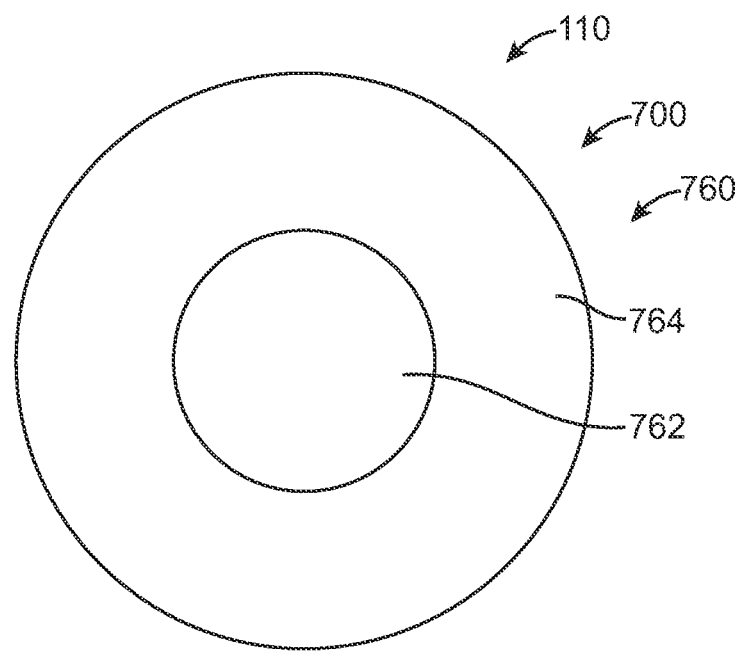
FIG. 7D shows an apparatus to deliver a first substance to the inner portion and the outer portion of the region of the cornea to denervate the cornea, in accordance with embodiments of the present invention.
Figure 7E:
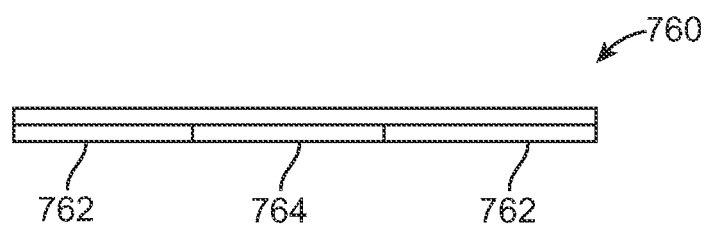
FIG. 7E shows a side view of an applicator as in FIG. 7A.
Figure 8A:
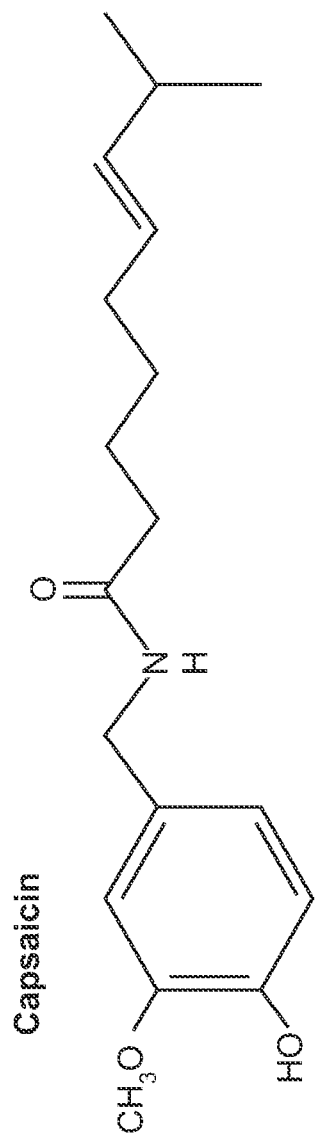
FIG. 8A shows the chemical structure of Capsaicin, in accordance with embodiments of the present invention.
Figure 8B:
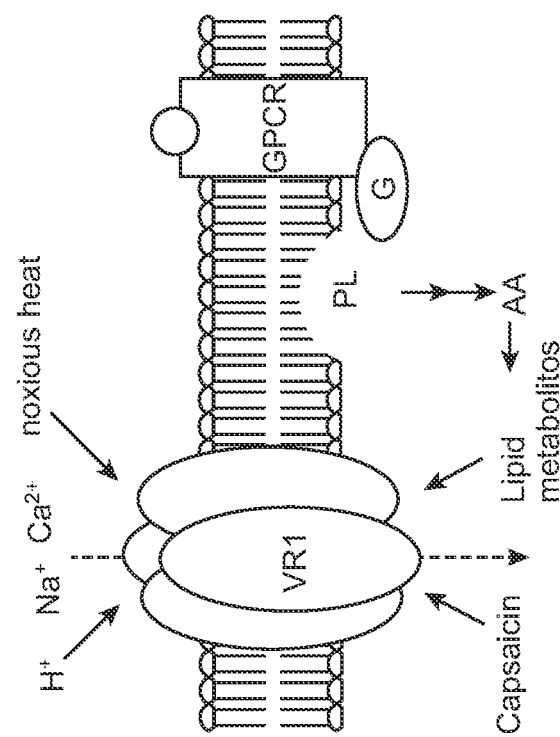
FIG. 8B shows Vanilloid Receptor 1 (VR1) receptor, which comprises a Capsaicin receptor suitable for use with a denervating substance, in accordance with embodiments of the present invention.
Figure 8B:
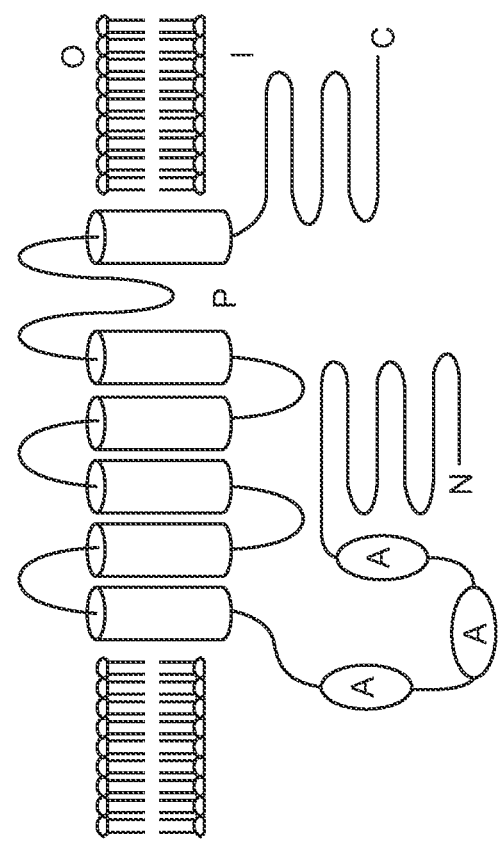
Figure 8C:
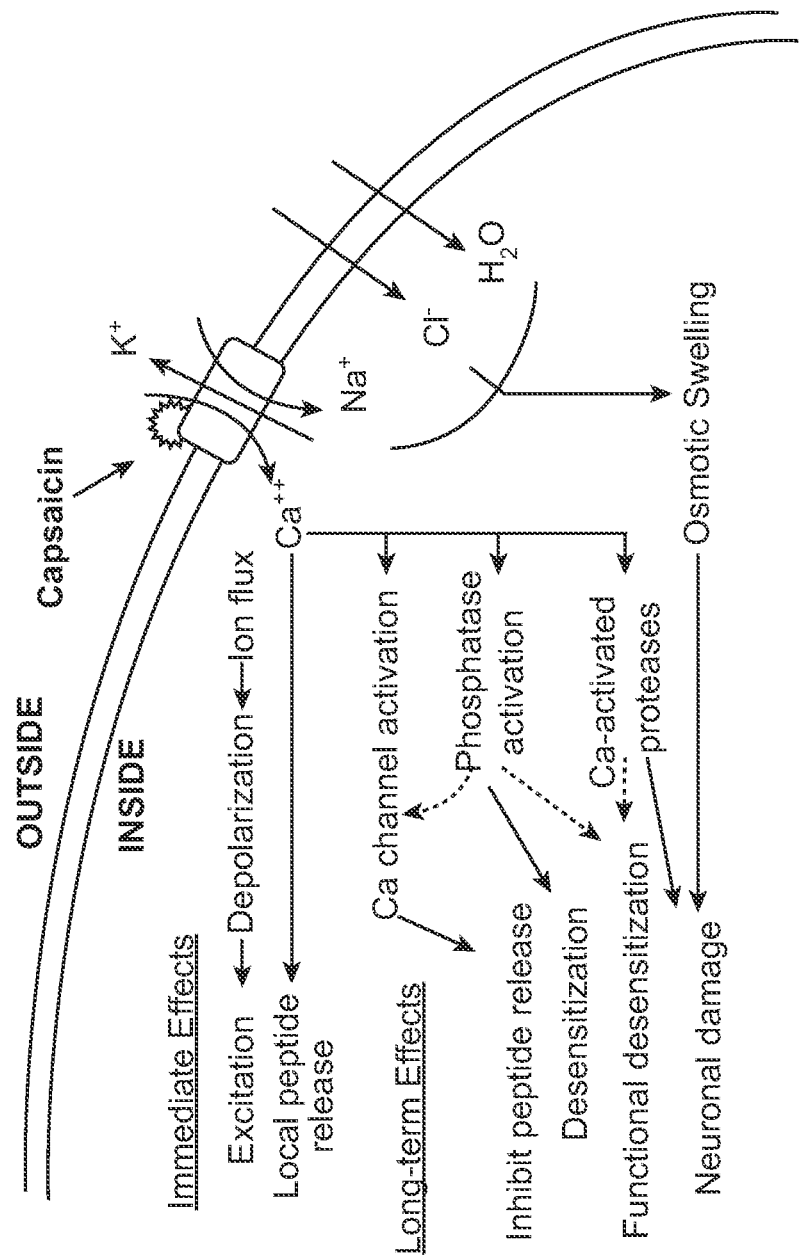
FIG. 8C desensitization with Capsaicin, in accordance with embodiments of the present invention.
Figure 8D:
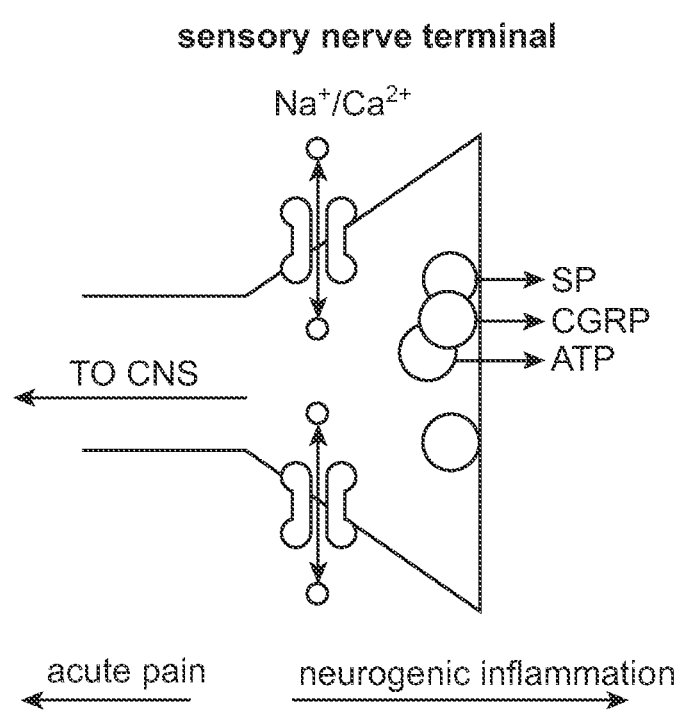
FIG. 8D shows neural channels sensitive to Capsaicin and afferent transmission of acute pain to the central nervous system and efferent transmission neurogenic inflammation to the cornea, in accordance with embodiments of the present invention.

FIG. 7D shows an apparatus 760 to deliver a first substance to the inner portion 42 and the outer portion 44 of the region of the cornea to denervate the cornea. FIG. 7E shows a side view of an applicator as in FIG. 7A. Apparatus 760 comprise an inner portion 762 with a first substance disposed thereon and an outer portion 764 with second substance disposed thereon. The first substance of inner portion 762 may comprise a noxious substances such as a calcium channel agonist such as a capsaicin and the second substance of the outer portion 764 may comprise a calcium channel blocker anesthetic. Alternatively, the first substance of inner portion 762 may comprise may comprise a calcium channel blocker anesthetic and the second substance of the outer portion 764 may comprise a noxious substances such as a calcium channel agonist such as a capsaicin.

A person of ordinary skill in the art can conduct experiments to determine empirically the inner or outer location of the noxious substance comprising the calcium channel agonist such as capsaicin and the inner or outer location of the anesthetic comprising the calcium channel blocker, and also the concentration of the first and second substances and duration of application.

The first and second substances may be coated on the inner and outer portions of the substrate with an amount per unit area.

Desensitizing Agents

The desensitizing agent as described herein can be delivered in accordance with treatment profile 120 so as to denervate the target tissue, for example the cornea, for a plurality of days. As the substance is delivered in accordance with the treatment profile 120, the amount of desensitizing agent delivered to the target tissue can be increased substantially to achieve the desired amount of desensitization. The desensitizing agent may comprise one or more of a noxious substance, a chemical, or a neurotoxin. The desensitizing agent may comprise Botulinum A toxin. The Botulinum A toxin may comprise one or more serotypes of Botulinum toxin such as Botulinum type A, Botulinum type B. For example, the substance may comprise Botulinum Toxin Type, commercially available as Botox®, delivered in accordance with the treatment profile 120 so as to treat the target tissue safely. The Botulinum toxin may comprise one or more of a heavy chain or a light chain of the toxin. The substance may act upon a receptor of the corneal nerves, such as one or more of a sodium channel blocking compound, or a potassium channel blocking compound. For example the substance may bind to and activate the transient potentially vanilloid receptor.

The substance may comprise a neurotoxin, such as a pharmaceutically acceptable composition of a long-acting sodium channel blocking compound, in which said compound binds to the extracellular mouth of the sodium channel, occluding the channel by a mechanism separate from that of local anesthetics, such as proparacaine. The substance may comprise a toxins or analogs thereof that specifically bind to a site formed in part by an extracellular region of the alpha subunit of a sodium channel. For example, the substance may comprise the class of toxins and analogs that specifically bind to a site formed by the SS1 and SS2 extracellular regions of the alpha subunit of a sodium channel. The substance may comprise on or more of tetrodotoxin, saxitoxin and analogs thereof.

The transient receptor potential vanilloid-1 (TRPV1) is a capsaicin-responsive ligand-gated cation channel selectively expressed on small, unmyelinated peripheral nerve fibers (cutaneous nociceptors). When TRPV1 is activated by agonists such as capsaicin and other factors such as heat and acidosis, calcium enters the cell and pain signals are initiated. After disease or injury, cutaneous nociceptors may become persistently hyperactive, spontaneously transmitting excessive pain signals to the spinal cord in the absence of painful stimuli, resulting in various types of pain. When TRPV1 is continuously activated through prolonged exposure to an agonist (e. g., capsaicin), excessive calcium enters the nerve fiber, initiating processes that result in long-term yet reversible impairment of nociceptor function. The application of capsaicin can provide relief from pain with this mechanism.

FIG. 8A shows the chemical structure of Capsaicin.

The substance comprising desensitization agent may comprise a substantially hydrophobic and lipophilic substance such as Capsaicin. When delivered to the surface of the epithelium as described above, the hydrophobic Capsaicin can be substantially localized to the epithelium, with treatment profile 120 as described above. For example, the elevated concentration of Capsaicin may be localized to the epithelium near the edge of a debridement of the epithelium.

Capsaicin may comprise a purified extract from chili peppers (Genus *Capsicum*). Capsaicin comprises an odorless, flavorless, lipophilic substance. Capsaicin is a capsaicinoid, a family of chemicals found in these peppers which can induce the feeling of heat upon ingestion.

FIG. 8B shows Vanilloid Receptor 1 (VR1) receptor, which comprises a Capsaicin receptor suitable for use with a denervating substance. VR1 receptors are found in the peripheral neurons in the skin and cornea, for example Aδ and C fibers. The primary receptors have somata in the dorsal root ganglion and the trigeminal ganglion. The VR1 receptor comprises a non selective cation channel which mediates stimuli from both chemical and physical triggers, including heat, low pH, capsaicin and some chemical biproducts from inflammation. As capsaicin is lipophilic, the binding site for capsaicin can be inside or outside of the cell membrane.

Capsaicin can induce a feeling of pain. Capsaicin binds to nociceptors, which stimulate afferent thinly-myelinated Aδ and un-myelinated C fibers. When the VR1 receptor is not activated, the VR1 receptor remains closed. Upon activation, for example with capsaicin binding, the VR1 channel opens. Since the VR1 receptor is a non-selective cation channel, when capsaicin binds, positive ions, for example calcium, can flow into the axons and dendrites of the neurons. The substantial effect of the opening of the channel of the VR1 receptor is an influx of calcium ions, resulting in a depolarization. This depolarization can eventually induce an action potential. When the neurons containing these receptors are stimulated, the neurons release a neurotransmitter, substance P. Substance P can communicate a message eventually perceived as an itch, burning sensation, or pain, for example with release of substance P (SP) into the cornea.

FIG. 8C desensitization with Capsaicin and mechanisms of desensitization. Desensitization with Capsaicin may comprise functional desensitization or pharmacological desensitization or both. Functional desensitization comprises the eventual reduction or loss of responsiveness of the neuron to other stimuli. Pharmacological desensitization comprises the progressive decline in the size of subsequent responses to capsaicin after prolonged or repeated exposures.

Capsaicin can cause desensitization via multiple mechanisms. At least one mechanism involves the calcium dependent activation of a protein phosphatase called calcineurin, which is mainly associated with activating the T cell immune response. Capsaicin activation of the VR1 receptor can induce an increase in the intracellular calcium concentration. This increase in calcium ions stimulates calcineurin, causing the calcium-dependent dephosphorylation of various proteins, ion channels, and enzymes. The dephosphorylation of one of calcineurin's protein targets can result in a functional desensitizing effect.

Capsaicin comprises a TRPV1 agonist, that can be administered locally to the site of pain, for example to the cornea. Two substantial types of pain sensing nerves are C-fiber neurons and A-delta neurons, for example of the cornea as described above. Long-lasting "noxious pain" can be transmitted in the body by C-fiber neurons and is associated with longer-term, dull, aching, throbbing pain. In contrast, A-fiber neurons can transmit immediate "adaptive pain," such as that experienced milliseconds after the slamming fingers in a door or after touching a hot surface. Capsaicin acts on TRPV-1 receptors expressed most densely in C-fiber neurons. These C-fiber neurons transmit long-term pain signal to the brain, and Capsaicin acts as a TRPV-1 agonist so as to bind these pain receptors and open the calcium ion channels as described above.

After initial stimulation with Capsaicin, desensitization of the TRPV-1 receptors blocks noxious pain. This desensitization leads to a prolonged, reversible and localized desensitization of the pain fibers.

The Capsaicin drug generally has a short half-life of 1 to 2 hours when absorbed into the blood stream, and is undetectable in the blood after 24 hours.

Capsaicin comprises a high safety profile suitable for use with refractive surgery such as PRK.

Because Capsaicin acts primarily on C-fiber neurons, Capsaicin may not to have an adverse effect on normal sensation such as temperature or touch, depending upon the dose based on the teachings as described herein.

FIG. 8D shows neural channels sensitive to Capsaicin and afferent transmission of acute pain to the central nervous system (hereinafter "CNS") and efferent transmission neurogenic inflammation to the cornea. The Capsaicin can trigger the release from the neuron of one or more of substance P (SP), adenosine triphosphate (ATP) or calcitonin gene-related peptide (CGRP). In at least some embodiments, the Capsaicin can be applied to the epithelium to trigger the release of one or more neuropeptides such as SP or CGRP and the epithelium removed, for example scraped away, so as to remove the neuropeptide with the epithelium.

Capsaicin can be used for PRK. For example, the release of Capsaicin can be controlled with an applicator as described above. The controlled release may comprise one or more of a quantity of release, a rate of release, region of release such as to an inner portion of the cornea or an outer portion of the cornea, or both the inner portion and the outer portion. The quantity of capsaicin may be determined with concentration of Capsaicin applied to the cornea for an amount of time. For example, the covering, or shield, as described herein can be provided with Capsaicin coated thereon for accelerated release and delivery of fixed amount of Capsaicin to a target location on the eye with the covering.

Inhibition of Pain with Post-Op Anesthetic

Figure 9:
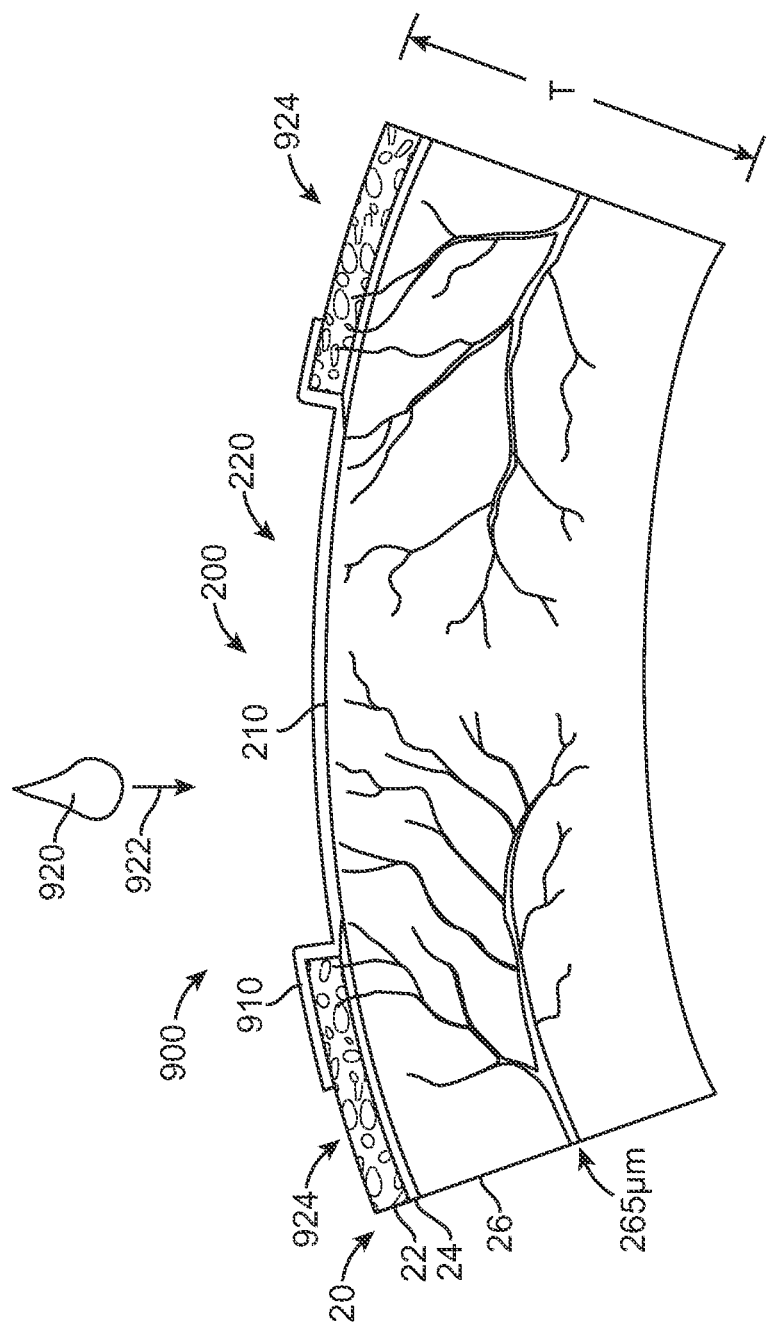
FIG. 9 shows a covering positioned on the eye over an epithelial defect so as to inhibit delivery of an anesthetic to the epithelial defect when the covering conforms to a boundary of the epithelium and the defect and seals the cornea, in accordance with embodiments of the present invention.

FIG. 9 shows a method of treatment 900 with a covering 910 positioned on the eye over an epithelial defect so as to inhibit delivery of an anesthetic to the epithelial defect when the covering conforms to a boundary of the epithelium and the defect and seals the cornea. The cornea 20 may ablated with PRK and the covering 910 positioned over the ablation. The covering may comprise a soft portion that conforms to the epithelium so as to seal the cornea. For example, the covering 910 may comprise a conformable covering as described in U.S. application Ser. No. 12/384,659 filed Apr. 6, 2009, entitled "Therapeutic Device for Pain Management and Vision," the entire disclosure of which is incorporated herein by reference and suitable for combination in accordance with some embodiments described herein. An anesthetic, for example that alters function of calcium release channels, can be applied 922 to the cornea with a drop 920. The drop of anesthetic spreads over the tear film of the eye. A the shield 920 conforms to the edge of the epithelium that defines the epithelial defect, the cornea is substantially sealed to inhibit swelling. The drop of anesthetic is absorbed preferentially by the epithelium away from the covering at location 924, as the covering 910 can inhibit penetration of the anesthetic to the cornea. The anesthetic can treat the nerves of the cornea peripheral to the epithelial defect to inhibit pain and so as to inhibit effect of the anesthetic on the regenerating epithelium near the defect, such that re-epithelialization is not delayed substantially with application of the anesthetic.

Figure 10:
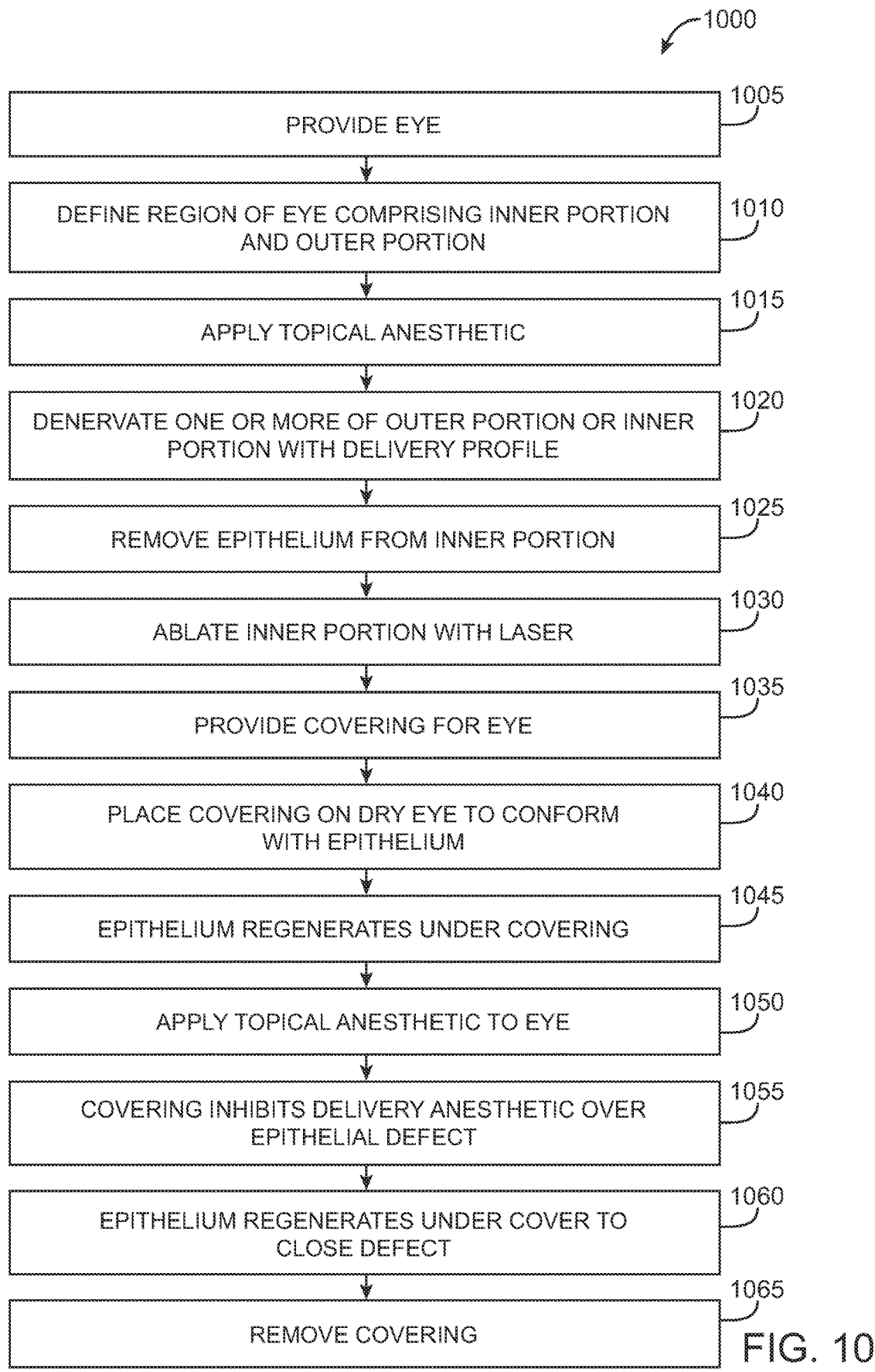
FIG. 10 shows a method of treating an eye of a patient in accordance with embodiments of the present invention.

FIG. 10 shows a method 1000 of treating an eye of a patient in accordance with embodiments of the present invention. A step 1005 provides an eye, for example as described above. A step 1010 defines a region of the eye comprising an inner portion and an outer portion, for example as described above. A step 1015 applies a topical anesthetic, for example as described above. A step 1020 denervates one or of the outer portion of the inner portion with a delivery profile, for example as described above. A step 1025 removes the epithelium from the inner portion, for example as described above. A step 1030 ablates the inner portion with a laser beam, for example an excimer laser PRK as described above. A step 1035 provides a covering for the eye, for example a silicone shield with a wettable upper coating as described above. A step 1040 places the covering on the eye, for example when the eye is dry, such that the covering conforms to the epithelium so as to seal the cornea. A step 1045 regenerates the epithelium under the covering. A step 1050 applies a topical anesthetic to the eye, for example with drops, when the covering is sealed to the epithelium so as to inhibit delivery of the anesthetic to the epithelial defect and the regenerating epithelium near the defect. A step 1055 inhibits the deliver of anesthetic over the defect, for example with the covering and the seal, such that the anesthetic penetrates the epithelium near the limbus and so as to denervate the nerve bundle disposed in the stroma and denervate the inner portion of the ablated region of the cornea. A step 1060 regenerates the epithelium under the covering to cover the ablated stromal tissue and close the epithelial defect. A step 1065 removes the covering.

EXPERIMENTAL

Based on the teachings described herein, a person of ordinary skill in the art can conduct experiments to determine empirically the parameters to denervate the cornea to decrease pain, for example pain following PRK.

Figure 11:
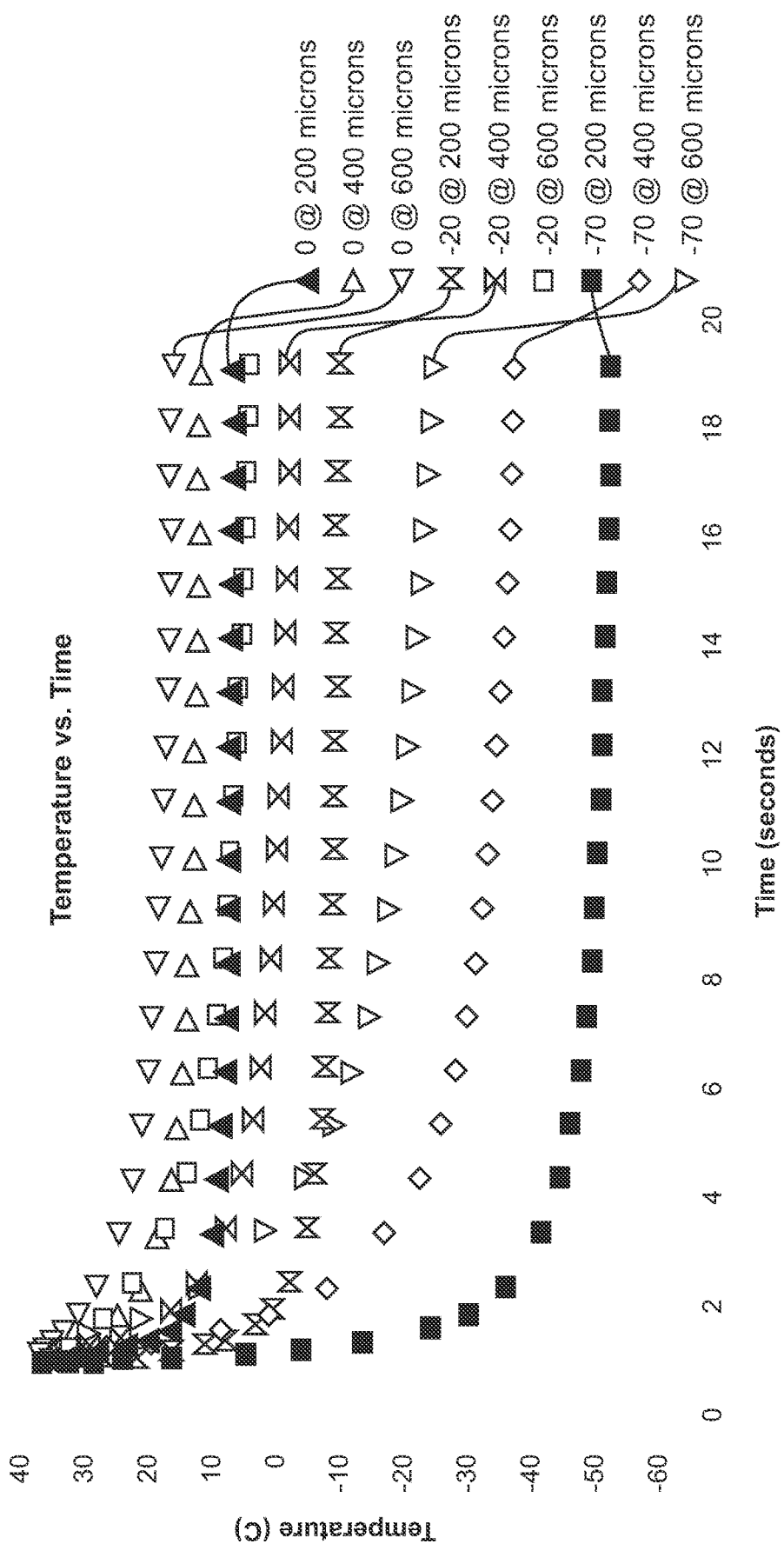
FIG. 11 shows experimental cooling data and profiles of corneal temperature at depths, in accordance with embodiments.

FIG. 11 shows experimental cooling data and profiles of corneal temperature at depths. For example, the cooling apparatus as described above can be chilled to a temperature such as 0 degrees C., or −70 degrees C. The apparatus can be contacted to the cornea to determine the temperature of the cornea as a function of time and depth. For example, a 0 degree C. probe can be placed on the cornea and the temperature of the eye determined over time at depths of 200, 400 and 600 microns. A −20 degree C. probe can be placed on the cornea and the temperature of the eye determined over time at depths of 200, 400 and 600 microns. A −70 degree C. probe can be placed on the cornea and the temperature of the eye determined over time at depths of 200, 400 and 600 microns. The temperature can be determined experimentally, or can be modeled with finite element analysis and non corneal heat transfer parameters, or a combination thereof. The denervation treatment profile can be determined, and the parameters adjusted such that pain is inhibited and also such that corneal innervation is restored after reepithelialization.

Similar studies can be conducted with heat, substances, ultrasound, light, photodynamic therapy and cutting as described herein.

While the exemplary embodiments have been described in some detail, by way of example and for clarity of understanding, those of skill in the art will recognize that a variety of modifications, adaptations, and changes may be employed. Hence, the scope of the present invention should be limited solely by the appended claims.

What is claimed is:

1. A method of treating a cornea of an eye, comprising:
    applying an apparatus to an anterior surface of a cornea, wherein the cornea comprises an epithelium, a stroma, an inner portion and an outer portion; and
    applying energy from the apparatus to denervate a region of the cornea corresponding to a denervation treatment profile,
    wherein denervating comprises severing axons in the region of the cornea.

2. The method of claim 1, wherein treating comprises denervating the inner portion of the cornea.

3. The method of claim 1, wherein the apparatus comprises an annular ring configured to contact the cornea.

4. The method of claim 1, wherein the energy comprises radiofrequency energy, heating, cooling, light, or ultrasound.

5. The method of claim 1, wherein applying energy comprises applying energy to the outer portion according to the denervation treatment profile.

6. The method of claim 1, wherein denervation comprises severing axons with the nerve sheath intact.

7. The method of claim 1, wherein the denervation treatment profile comprises an annular denervation treatment profile.

8. The method of claim 1, wherein the denervation treatment profile corresponds to a depth within the cornea.

9. The method of claim 1, wherein the denervation treatment profile is localized substantially to the stroma.

10. The method of claim 1, wherein the denervation treatment profile encompasses nerve bundles.

11. The method of claim 1, wherein the denervation treatment profile is determined by the intensity of the energy, the duration the energy is applied, or a combination thereof.

12. The method of claim 1, wherein the denervation treatment profile is localized substantially to the epithelial layer.

13. The method of claim 1, wherein the treatment profile is configured to denervate nerves at a predetermined depth within the cornea.

14. The method of claim 1, wherein the treatment profile is configured to denervate nerves of the epithelium without substantial penetration to nerves below a Bowman's membrane of the eye, or to denervate nerves extending along lamella of a stroma disposed between the epithelium and an endothelium of the outer portion.

15. The method of claim 1, wherein the treatment profile is configured to denervate nerves in the outer portion of the cornea without causing substantial damage to endothelial cells.

16. A method of treating a cornea of an eye, comprising:
applying an apparatus to an anterior surface of a cornea, wherein the cornea comprises an epithelium, a stroma, an inner portion and an outer portion; and
applying energy from the apparatus to denervate a region of the cornea corresponding to a
denervation treatment profile,
wherein denervation comprises stunning corneal nerves, increasing the threshold of the corneal nerves, inhibiting corneal nerve transmission, blocking the corneal nerve transmission, or a combination of any of the foregoing.

17. A method of treating a cornea of an eye, comprising:
applying an apparatus to an anterior surface of a cornea, wherein the cornea comprises an epithelium, a stroma, an inner portion and an outer portion; and
applying energy from the apparatus to denervate a region of the cornea corresponding to a
denervation treatment profile,
wherein denervation comprises denervating nerves without causing substantial damage to the endothelium.

* * * * *